(12) United States Patent
Koltin et al.

(10) Patent No.: US 6,514,715 B2
(45) Date of Patent: Feb. 4, 2003

(54) ESSENTIAL FUNGAL GENES AND THEIR USE

(75) Inventors: Yigal Koltin, Newton; Victoria Gavrias, Upton, both of MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/911,888

(22) Filed: Jul. 23, 2001

(65) Prior Publication Data

US 2002/0119509 A1 Aug. 29, 2002

Related U.S. Application Data

(62) Division of application No. 08/965,762, filed on Nov. 7, 1997, now Pat. No. 6,280,963.

(51) Int. Cl.⁷ .......................... C07H 21/04; C12Q 1/68; C12N 15/63
(52) U.S. Cl. ................ 435/7.31; 435/254.3; 435/320.1; 536/23.1; 536/24.5
(58) Field of Search ............................. 435/7.31, 254.3, 435/320.1; 576/23.1, 24.5

(56) References Cited

FOREIGN PATENT DOCUMENTS

| WO | WO 95/06132 | 3/1995 |
|----|-------------|--------|
| WO | WO 95/10625 | 4/1995 |
| WO | WO 97/42210 | 11/1997 |

OTHER PUBLICATIONS

Berendsen, A glimpse of the holy grail, Science, vol. 2828, pp. 642–643, 1998.
Doshi et al.; "Two α–tubulin genes of *Aspergillus nidulans* encode divergent proteins"; *Mol. Gen. Genet.*, vol. 225; pp. 129–141; 1991-XP002109954.
Du, database PIR2, Accession # S59791, Jan. 13, 1996.
New England Biolabs Catalog, pp. 60–62, 1986/87.
Savitt et al., database PIR2, Accession # I50712, Jan. 13, 1996.
Topczewski et al.; "Cloning and characterization of the *Aspergillus nidulans* cys B gene encoding cysteine Synthase"; *Current Genet.*, vol. 31; pp. 348–356; 1997— XP002109934.
Tuite; "Antifungal drug development the indentification of new targets"; *Trends in Biotechnology*, vol. 10, No. 7; pp. 219–220; Jul. 1, 1996– XP004035757.
Tuite; "Discovery and development of new systemic antifungals"; *TIBECH*, vol. 14; pp. 219–220; Jul. 1996.
Yanai et al.; "Isolation and Characterization of Two Chitin Synthase Genes from *Aspergillus nidulans*"*Biosc. Biotech. Biochem.*, vol. 58; pp. 1828–1835; 1994—XP002109955.

*Primary Examiner*—Andrew Wang
(74) *Attorney, Agent, or Firm*—Fish & Richardson, P.C.

(57) ABSTRACT

Disclosed are essential Aspergillus polypeptides and genes (AN97, AN17, AN80, and AN85), as well as homologs thereof, which can be used to identify antifungal agents for treating fungal infections such as aspergillosis.

24 Claims, 46 Drawing Sheets

(SEQ ID NO:1)
1   AGGGCTGCGCAGGGCAGCTGTGCAAATGCCGGACGCTTTGGCGAAACATCCTGTCTCCTGAAACAGAAAAGACAAGACGAAGT   100
    TCGGGACGCGTCCCGTCCCTGACACCGTTTAGCGGCCTGCGAAACCGCTTGTGTTAGGACACAGTTATAGTTACGACGAGACTTGTCTTTCTCTGTCTGCTTCA
(SEQ ID NO:3)

101 TCCCGGATTGTATCTCGAATGAGGGGACCGATTTCCGGCGTTAGTAAGAGGTCACGTGAAAGATGGCGTGCTAACTAGTAGTAAGGCTATGCAAGCATTCGGCTCA   200
    AGGGGCGTAACATAGAGCTTACTCCCCTGGCTAAAGGCCGTAAAGGCCTATCTCCAGTGACACTCTTCTACCGCACGATTGATCATACGTTCCGTAAGCCGAGT

201 GGCAAATACCCAGTCAACAATTTGTTGCCTGAGAGTGGAAATACGAGACCCTTGATTGTGCCGAGCAGTGTGATTAGGATAGCTGAGGCATTGTATTCAT   300
    CCGTTTATGGGTCAGTCAGTTGTTAAACAACGGACTCTCGGGAACTAACTCCTATCTGACTCCGTAACATAAGTA

301 GTATCAGGAACCTGATCGTCAAAGCGTTGCAGGCTGCTGGGACCCCGACCCTGCACGACCGTGCACGACGCGTCTGGACGTCCGACAAGCGTTCGCAGTGAGCTGCTTTATGCT   400
    CATAGTCCTTGACTAGCAGTCGTTGCCAATATATTGCTCATCAATAGATAGATAACCCCACAAACAAATACGA

401 CCGGCCCCGTGACTCTCAGCAACGAGTTGTATAACGAGTGGCAGCAGCCAACGAACTTCTTTGCTGCCAACAAAGCCTTTACTGGAAA   500
    GGCGGGACACTGAGAGTCGTTGCCAATATTGCTCATCAATAGATAGATAACCCCACAAACAAATACGA
    GGCGGGGCACTGAGAGTCGTTGCAATATTCATCGGTCGGTCGGTGGTTTGTTTCGGAAATGACCTTT

501 CAGGGCTGATCAGCAAATCAAGAGATATACTAGAGATGAGTTGATATTATCACCGGCCGACACCCTTACTGACCCGACAGATTACTGACCGCAGATTACTGACCCGACAGATC   600
    GTCCGACTAGTCGTTTAGTTCTATATGATCTCAACTATATAGTGGCCGGTCTAATGACTGGGGCTGTGGGAATGACCAGTAATGGGAGCTAG

FIG. 1A

```
601  AAGATGCCGAGTCGAGTTTCCGCCCGTTCAACATCCACCGCCTCGGCCAAGGCTCTACACAGACTGGACAAGCCTGGCGCTCAGGACCCAT  700
     TTCTACGGCTCAGTCAGCTCAAAGGCGGGCCAAGTTGTAGGTGGCAGCGCGGCGGTTTCCGAGCGTGTCGACGCGGCCGACGAGTCGCTGGGTA
1    M  P  S  R  V  S  A  R  S  T  S  T  A  S  R  K  G  S  T  Q  T  A  T  S  G  R  A  G  S  A  T  P  S    33
                                                                                              (SEQ ID NO:2)

701  CATTCGCCATCCCAGAGGAAACTGCATTACCCGAGGCTGTTCAACCCTTCGCCGGATGTATGCGCCATTTTCGCAGACGTTGCGACTGCCGG  800
     GTAAGCGGTAGGGTCTCCTTTGACGTAAGCTCCGACAAGTTGGGAAGCGGCCTACATACGCGGTTAAAGCGCCTGGTGCAAGCTGACGGCC
34   F  A  I  P  E  E  T  A  L  P  E  A  V  P  T  L  R  R  D  V  C  A  I  F  A  D  A  Q  R  S  T  A  G    66

801  TCATCGCAAACTTGTCGTCCGACTAAGGAAATCCAGGAGGTGTGCTGTGCTATACCCCAGAAGAACTCAACTCAGTTCAACTGAAGAGGATTG  900
     AGTAGCGTTTGAACAGCAGGCTGATTCCTTTAGGTCCTCCACACGACACGATATGGGGTCTTCTTGAGGTTTTTCTGTCAAGTTGACTTCTCGCTAAC
67   H  R  K  L  V  V  R  L  R  K  I  Q  E  V  C  C  A  I  P  Q  K  N  S  K  K  D  S  S  T  E  E  R  L    99

901  ATTCCCGGCGAAGAGACGGTTCAACGTGTACCAGATGCGTGTGTGGCGCATCTGTCTATTAAGAGAACAGAGCCTGTTGGCG  1000
     TAAGGGCCGCTTCTCTGCCAAGTTGCACATGGTCTACGCACACACCGCGTAGAACAGATAATTCTCTGTCTCGGACAACCGC
100  I  P  G  E  E  T  V  P  E  K  E  F  N  V  E  V  S  R  C  V  L  R  I  L  S  I  K  K  T  E  P  V  G  D    133

1001 ATGGAATCCTGCGGTTTCTCGGGAACTTCCTACTCATGCCTGAGATCTTCGGCTGAGAAAGAAGACGCTGAGACTCTGAAGAGATGCAGAATTC  1100
     TAGCTTAGGACGCCAAAGAGCCCTTGAAGGATGAGTACGGACTCTAGAAGCCGACTCTTCTGAGACTCTGTCTATACGTCTTAAG
134  R  I  L  R  F  L  G  N  F  L  T  H  A  S  E  K  D  A  E  I  F  G  S  E  E  D  D  M  Q  N  S            166
```

FIG. 1B

```
1101  GCACGAAAGACCGACTGCCCACTGACTTGTCTCCCTGTTAGTGCTTGTGCTTCCGTACCACGCAA  1200
      CGTGCTTTCTGGCTGACGGGTGAACTGGTGGTGCAGAACAACAGAGGACAATGACGTTTCGTTCCAACACGCAAGGCATGGTGCGTT
167   H  E  R  P  T  A  H  L  T  T  S  L  V  S  L  L  V  P  L  L  S  A  K  D  K  V  V  R  P  R  T  T  Q   199

1201  ATTATCGGCACATCGTCAATTCACTCGATACCGTAGACGAATTATACCACACTCTCCGGCAAGGCCTTCTAAAACGGATTCGGACAAAGAACCTT  1300
      TAATAGCCGTGTAGCAGTTAAGTGAGCTATGGCATCTGCTGCTTAATATGGTGTGAGAGGCCGTTCCGGAAGATTTTGCCTAAGGCCTGTTTCTTGGAA
200   I  I  A  H  I  V  N  S  L  D  T  V  D  D  E  L  Y  H  T  L  R  Q  G  L  L  K  R  I  R  D  K  E  P  S   233

1301  CGGTGCGGGTACAAGCAGTGATGGTCTCGGCCGTTGGCCCCGGAAATGAAGAGGACGATGACGAAAATGATACCAGTGGTCTTGTGAGAAGCTCGT  1400
      GCCACGCCCATGTTCGTCGTACTACCCAGAGCCGGCGAACCCGGCTTTACTTCTCCTGCTACTGCTTTATACTATGGTCACGGGAACACCCTTCGAGCA
234   V  R  V  Q  A  V  M  G  L  G  R  L  A  G  N  E  E  D  D  D  E  N  D  D  T  S  A  L  V  E  K  L  V   266

1401  GGACATAATGCAAATGACACGGCTGCAGAGGTTCGGAGGACATTACTCCTCAACCTCGTCTACCCTTCCATACCTCCTGATTCGTCGAACGCGCC  1500
      CCTGTATTACGTTTACTGTGCCGACGTCTCCAAGCCTCCTGTAATGAGGAGTTGGAGCAGATGGGTAACTAAGGAGTATGGAGGAGCTGCGCGG
267   D  I  M  Q  N  D  T  A  A  E  V  R  R  T  L  L  N  L  P  L  I  P  S  T  L  P  Y  L  L  E  R  A   299
```

FIG. 1C

```
1501 CGTGACCTCGATGCTCCCACGAAGGGCATTATATTCTCGTCTACTTCCGACACTGGGAGATTTCTCTCCATGAGAGAAAAGTTGC  1600
     GCACTGGAGCTACGAGGGGTGTCCCGTAAATATAAGACCAGATAAGGCTGTGACCCTCTAAAGGCTGTAAATAGAGAAGTACTCTCTTTACTG  333
300  R  D  L  D  A  P  T  R  R  A  L  Y  S  R  L  L  P  T  L  G  D  F  R  H  L  S  L  S  M  R  E  K  L  L

1601 TCAGATGGGCTCTCGTGATCGCGACAAAGTGTTCTATGACCGCTGATTGAGATATCGGCACGAACAATGAC  1700
     AGTCTACCCCGAGAGCACTAGCGCTGTTTTCACACTCCTCCGGTGACTTTCAACAGATACTGGCGACTAACTCTATAGCGACCGTGTTACTG  366
334  R  W  G  L  R  D  R  D  K  S  V  R  K  A  T  G  K  L  F  Y  D  R  W  I  E  I  S  L  A  R  T  M  T

1701 CCTGAGAATTCGGCAGCCTCGAACGAGAATTCCCGCTTTACTGAGTTGTTGGAGCGTATCGATGGTGAACTCAGGCATGGAATCGGCATAGCG  1800
     GGACTCTTAAGCCGTCGGAGCCTTGCTCTTAAGGGCGAAATGACTCAACAACCTCGCATAGCTACACCACTTGAGTCCGTACTTAGGCGTATCGC  399
367  L  R  I  R  A  A  L  G  T  R  I  P  A  L  L  E  L  E  L  L  E  R  I  D  V  V  N  S  G  M  E  S  G  I  A

1801 CACGAAGCTATGCGCAGTTTCTGGAAGGTCGACCAGAGTCGAGAGGCGGTACTATTCGACGAAGCCTTCTCGGGAGTCAATGACAGCAGAATCCGCTT  1900
     GTGCTTCGATACGCGTCAAAGACCCTTCCAGCTGGTCTCCGCCATGATAAGCTGCTTCGGAAGACCCTCAGTTACTGTCGTCTTAGGCGAA  433
400  H  E  A  M  R  S  F  W  E  G  R  P  D  Y  R  E  A  V  L  F  D  E  A  F  W  E  S  M  T  A  E  S  A  P

1901 TCCTCCTCCTCATTCAATGACTTTTGCCGGGTTGAAAACGAAGGTAAATATGACAGCCTGGCCGATGAGAATCCAGTCGTTACAGCCCTCGCAAT  2000
     AGGAGGAAGCGAGTAAGTTACTGAAAACGGCCCAACTTTGCTTCCATTTATACTGTCGGAGCGCTACTCTCTAGGGTCAGCAATGTCGGAGCGTTA  466
434  L  L  R  S  F  N  D  F  C  R  V  E  N  E  G  K  Y  D  S  L  A  D  E  K  I  P  V  V  T  A  L  A  M
```

FIG. 1D

```
2001  GTATCTTCATAAGTACACTGACCTTCTGCAGGCGCTTCTGAGAAGCTCACAAAGGATGCTACTGACGTAAACGACGACGATACCGTCGAAATATGGAATTTATC   2100
      CATAGAAGTATTCATGTGACTGGCTCGAAGACGTCGCGTTCTTCGAGTGTTCCTACGATGACTGCATTGCTGCTGCATGGCAGCTTTAGCTTAATAG

467   Y  L  H  K  Y  M  T  E  L  L  Q  R  K  K  L  T  K  D  A  T  D  V  N  D  D  D  T  V  E  I  E  F  I                                499

2101  GTCGAGCAACTGCTTCACATCGCAATGACACTAGACTACTCGGATGAAGTGGGCGTCGACGAAGTGTTTCTCTACTCCGTCTCGCTGAGCTCCAG              2200
      CAGCTGTTGACGAAGTGTAGCGCTACTGATGAGCCTACTTCAGCCCGGCGCTTCTACAAAGAGATGAGGACACTCGAGAGGACACGGTC

500   V  E  Q  L  L  H  I  A  M  T  L  D  Y  S  D  E  V  G  R  R  K  M  F  S  L  L  R  E  A  L  A  V  P  E                             533

2201  AGCTCCCTCAGGAATCGACCAAGTCCGGTTGAGACACTGAGATGTGTTGTGGGCCCGACGCGGCAGAGAGCGAATTCTGCAGTGTTGTTCTGA                2300
      TCGAGGGAGTCCTTAGCTGGTTCGAGCGGCCAACTCTGTGACTCTGTACAACACCCGGGCTGCGCCGTCTCGCTTAAGACGTCACAAGACCT

534   L  P  Q  E  S  T  K  L  A  V  E  T  L  R  C  V  C  G  P  D  A  A  A  E  S  E  F  C  S  V  V  L  E                                566

2301  AGCCATTGCTGAAGTTCATGACAATCAGACACCGAGGATAGTTCGTTTCTGCAAAGTCTGAGATTAGCGATGATGCCAGCGCCAACGATCCGAA              2400
      TCGGTAACGACTTCAAGTACTGTTAGTCGTGGTCCTATCAAGCAAAGACGTTTCAGACTGTTAATCGTACTACGGTCGTCGGCGTTGCTAGGCTT

```
2401  ACGCCGATGAGTGAAGATGACAAGCCATTCAACAAGGAGGAGGCAAAGGCTAAGGTCCTCAAGGAAATCGTTATTAATGAAGTGCTGCACATTGCCC  2500
                                                                                                          TGGGCTACTCACTTCGTTCGTTAAGTTGTTCCTCCCTCCGGAGTTCCTTAGGAGTTCCGATTCGTTCCAGGAGTTCCTTAGCAATATTATACTTCACAGACGTGTAACGGG
600   T  P  M  S  E  D  D  K  P  F  N  K  E  E  A  K  A  K  V  L  K  E  I  V  I  N  M  K  C  L  H  I  A  L  633

2501  TTTGCATGCTCTCCAGAATGTTGAAGGCAACCTGCAAGCAAATATGAATCTGGTGACCATGTTGAATAACTTGGTAGTACCTGCTGTTCGAGCCACGAAGC  2600
                                                                                                          AAACGTACGAGAGGTCTTACAACTTCCGTTGGACGTTCGTTTATACTTAGACCACTGGTACAACTTATTGAACCATCATGGACGACAAGCCTCGGTGCTTCG
634   C  M  L  Q  N  V  E  G  N  L  Q  A  N  M  N  L  V  T  M  L  N  N  L  V  V  P  A  V  R  S  H  E  A  666

2601  GCCAATTCGAGAGCGCGGTCTCGAATGTCTGGCCTGTGCTGGACAAGTAAGTTCCATCCTTACTAAATACATCTCTCTCTAACCTCTCT  2700
                                                                                                          CGGTTAAGCTCTCGCGCCAGAGCTTACAGAACCCGACTTACGAAGTTATTCATTCAAGTAGGAATGATTTATGTAGAAGAGATTGGAGAGA
667   P  I  R  E  R  G  L  E  C  L  G  L  C  C  L  L  D  K  684

2701  GTTAGACTCTCGCAGAAGAAATAATGACGCTGTTTATTCACTGTTACAGCAAGGCCACGAAAACCTACAGTTCACTGCTATTCATATCCTTTGGATAT  2800
                                                                                                          CAATCTGAGAGCGTCTTCTTTATTACTGCGACAAATAAGTGACATAAGTGACGATAAGTATTATGACGATAATAGTATAGGAAACGCTATA
685   T  L  A  E  E  N  M  T  L  F  I  H  C  Y  S  K  G  H  E  N  L  Q  V  T  A  I  H  I  L  C  D  M  716
(SEQ ID NO:29)

2801  GTTAATTAGCCATCCTTCGCTGGGTGGCCACCGGAGGAGACAGTTGCGCCACCGGCGTTGCGCCAGAAGCCACTGCTTAAGTCTTTTCC  2900
                                                                                                          CAATTAATCGGTAGGAAGCCACCGGGAGGGCAATGGGTCCGTGTCAACGGCGGTGGCCGCAAGGTTCGGTGACGAATTCCAGAAAGG
717   L  I  S  H  P  S  L  V  A  P  V  T  Q  A  D  K  E  T  V  A  P  P  A  F  Q  K  P  L  L  K  V  F  S  749
```

```
3401  CAATGTTTGTGGCATTATCCACTTGCAACTGATTAAGGACATACTGGAACGAGTGCTCGGGATCAGTGAAGCAGCAATCGCTGCTCTAAACAACAACGA  3500
      GTTACAAACACCGTTAATAGGTGAACGTTGACTAATTCCTGTATGACCTTGCTCACGAGCCCTAGTCACTTCCGTCGTTAGCGACGAGATTGTGTTGCT
917   N  V  C  G  I  I  H  L  Q  L  I  K  D  I  L  E  R  V  L  G  I  S  E  G  S  N  R  C  S  K  Q  Q  R       949

3501  AAACTCCTGTTTCACTCAGTCATGAGCAAGCTCTATATTGCGCCAACGGCACTTTCGCGTCGAGAGACGACTCGTTCCGTTCCA                    3600
      TTTGAGGACAAAAGTGAGTACTCGTTCGATATATAACGCGGTTGCCGTGAAAGCGCAGTCGCAGGTCCAGGTCCCGGGGCTTCGCTGAGCAAGGCAAGT
950   K  L  L  F  S  L  M  S  K  L  Y  I  A  P  P  T  A  L  S  R  S  A  S  Q  A  P  E  D  D  S  F  R  S  S    983

3601  GCGTGCGAAGCTCCATGGCACTCAATCCCGAACTCAATGCCTCCGCGGCCAGGAAGTCAAGGAGTCTACTTGACCAGACCATCGAAGAGAAGGTGTGGCGGC  3700
      CGCACGCTTCGAGGGTACCGTGAGTTAGGGCTTGAACGGAGCGCGTCCTTCAGTTCCTCGATGAACTGGTCTGGTAGCTTCTCCACACCGCCG
984   V  R  S  S  H  G  E  L  N  P  E  N  L  A  L  A  Q  E  V  K  E  L  L  D  Q  T  I  E  E  G  V  A  A       1016

3701  TGATGCTGCTAGCCGAAATGCCCTCGTCAAGGTGAAGAACGTGTGTCAAGCTACTGGGGCTCCCATGCGACCTTCTAGCCGACGAGC               3800
      ACTACGACGATCGGCTTTACGGGAGCAGTTCCACTTCTGCCACTTCTTGCACACAGTTCGATGACCCGAGGGTACGCTGGAAGATCGGCTGCGCGGGCCTCG
1017  D  A  A  S  R  N  A  L  V  K  N  V  V  L  K  L  L  A  A  P  M  R  P  S  S  A  R  G  R  E  S          1049

3801  AGTGTCGAAAGTGACATTGGCAGTGTTCGATCTTCCAGAAGTGTTCGGCCCGTCCGTAGAGCCTTGGGCGCCGCCGGGTATCCGTGAGCCCAGTA        3900
      TCACAGCTTTCACTGTAACCGTCAAGCTAGAAGGTCTTCACAAGCCGCAGCAATCGGACCGAAACCCGGCGGCCACATAGGCACCTCGGGTCAT
1050  S  V  E  S  D  I  G  S  V  R  S  S  R  S  V  R  P  S  V  E  P  G  F  G  R  R  G  V  S  V  E  P  S  I    1083
```

FIG. 1H

```
3901  TCATGGAGGAGGATGAGAATGACTGTTACTCTGACACAGTAGAATGCCACGCTATGAGGAATGATTTC  4000
      AGTACCTCCTCCTACTCTTACTGAGAATGAGACTGTCATCTTACTGACATAGTTCTCCTCCTTACTAAAG
1084  M  E  E  D  E  N  E  D  S  R  M  T  V  I  K  E  E  D  A  D  A  M  E  E  *  1113

4001  GGTCTCAAGATCTTTGCTGTCTTGTTCGGCGTTGGGAGGTTTCCGGCAGGGCTAATGCTATATTTATGGTTAGGTTGCGATGTAATTATTCGATTCT  4100
      CCAGAGTCTAGAAACGACAGACCAAGCCGCAACCCCTCCAAAGGGCCGTCCCGATTACCAGTATAAATACCAATCCAACGTACATTAATAAGCTAAGA

4101  TGGTTATGCTTGAACATGCTCTATATGTTACAAATAATTCACTCCAAACGTTCATGTATGAGTATGGATATGTGTTTTATATTGGCCTTACCAGGATAGCTC  4200
      ACCAATACGAACTTGTACGAGATATACAATGTTATTAAGTGAGGTTTGCAAGTACATACTCATACCTAGACAAATATAACCGGAATGGTCCTATGCAG

4201  AGTTCTTGGCGAAGTTATCCCAGACTGACAGCTGCCTCCCAGGCCAGGAATTGGCTAGTCTTAGTCTTAGTAGCATCTTAGTTCTTAGTAGCATCGTGTATCAACAG  4300
      TCAAGAACCGCTTCAATAGGGTCTGACTGTCGACGAGGTCCGGTCCTTAACCGATCAGAATCAGAATCGTAGACTCCATCGTAGCACCATAGTGTC

4301  TGATCAGTGTGAAGGGCCATCGATCTGTTTGATCTTACCAGAACGTGTTACAACAATTCAACCACCACCATATATATGGTATCTGTCAATGTGAATGA  4400
      ACTAGTCACACCTTCCCGGTAGGCTAGACAAACTAGAATGCTTGCACAATGTTGTTAAGTTGGTGTATATATACCATAGCAGTTACACTTACT
```

FIG. 11

```
4401  ATCTGCTTGGGCAGCCTTATGACTCTGGTGACGCGACTCGGGGCTTGATTCAATGGGGACTCGAAGACCGCATGTGAGACTCCTAGCATGTGAGATGTGAGGCT
      TAGACGAACCCGTCCGTTGAGACTACTGAATACTAAGTTAGGCCCGTCGAGCCTGCGCTGAGCCCCGTTCTGGCGTACACCCTGGTACACCTCTGAGGATCGTAGCCTACACTCCGA                    4500

4501  TCCGTTTTAATTTCTTCCCTCCAAATCGTCTGCCTGCTCGCTGCTCCTGCGCTCGCCGCCTTTGAAATACTCCGAGGTACCAAAGTAAAGATAAAGTGACTCTGAGAGACTG
      AGGCAAAATTAAGAAGAGGTTTAGCAGACAGACGGAGCGACGAGCGACGAGCGAGGACGACGAAACTTTCATTTCTATTTACCAACTGAGACTCTGAC                                      4600

4601  CTTTGACCTCCTGACCAAGTCGTGCCTAGCCAGAAGGGAGTGTTTCAATGGCTTTGTGAGGCTACTAAGGCCGCACGATACACCCGAGATGCAAAGAA
      GAAACTGGAGGACCCTGGTTTCAGCAGACCTGTCTCCCTGCCGAAACACTACCGATGATTCCGAAAACACTACTCCGAAATTACTAACGACTCTGCTT                                      4700

4701  GTCCGATACGGTCGTCCATATCTCGAGCACCTTTATTGGCGCTTTGCAGTTATATGGAGGCGTTTAATGATTGCGTGTTCGAATCGATGAATAA
      CAGGCTATGCCAGCAGCTCGTAGAGACTAATAGAGTCTGTGAAAATGACCGTCAATGTCAATATAATACCCTCCGCAAATTACTACTAACGACTTAGGCTACTTATT                              4800

4801  TATCTCATTAGTCGACTAAACGGGATGAGGATGATGAGCTGCTGGTATCTGGTCTCAAACTGTAATAAGCGCTCTCCGCAACACCGTACGGTTGACAAT
      ATAGAGTAATCAGCTGATTGCCCTACTACTGACGACCATAGAACCAGAGTTTGACATTATTGCGAGAGCCGTTGTGGCATGCAACTGTTA                                              4900

4901  CCTGGGCAGATGCAGCACCTGTAGAATCCAAGAAGACGCAGCTGGACTCATTGAGACTATAATGACAGACTAATAATACAAAA
      GGACCCGTCTACGGTCGTGGACATCTTAGGTTCTTCGCGTCGACCTGAGTAACTCTGTCAACTTAAGGAAATTGATATTACTCTGTCTGATTATTATGTTTT                                  5000
```

FIG. 1J

FIG. 1K (SEQ ID NO:4)

1   CAAAGTCTTGATCACAGGGGCACAAGGCGCATGCTTACGGACGGCATGAAGGGGTCAAGGAGAAAGTCTTTGTGCTCGTGACGGTG
    GTTTTCAGAACTGTCACTTTGGGACGGAGGGATACGCCAGGCAATCACCAAGTAGAGTTGACAATGGGAACACCCAAAGTGCCAA 100
    (SEQ ID NO:6)

101 CCAACAGTACAGTGAAACCCTGAAACCCCTGGCGCTCGTCTCCTATCTCATGCGGTCTCGTGTTAGTGGTTTATGTTCTAACTGTTACCCCTTGTGGTTTTCACCGTTT 200
         M  F  L  T  V  T  P  C  G  F  S  P  F
         (SEQ ID NO:5)                                                                       13

201 AGCGGACTAGGATACTCAAGCTGTGTTGCCGTCTGCAGATGAATTCCTGGCGTCTCTGCAGATGAATTCCTGGCGTCTCATGACAATCATCTTCACTACCCGA
    TCGCCTGATCCTATGAGTTCGACGTTCGACAACGGACGTCTACTTAAGGACCGCAGAGTCTACTTAAGTAGAGTAAGTGATGGGCCT 300
 1  S  G  L  G  Y  S  K  L  C  P  V  C  R  L  A  D  E  F  L  A  S  H  R  N  D  H  R  S  L  T  I  I  F  T  T  R  S   47

301 GCACAAGAAAGGAAGGACACACCCTTCGCAACTACAGAATCACCTCCCGACCCTCGAGTGACCTTGTTCCTGA
    CGTGTTCTTTCCCTTCCTGTGTGGGAAGCGTTGATGTCTAGTGGAGGACTCCACTGGAACCAAGGACT 400
 48 T  R  K  G  S  D  T  L  R  N  L  Q  N  H  L  R  T  S  T  F  G  A  S  A  T  A  R  V  T  P  V  P  E   80

401 AAATGTCGACCTCTGCAACCTCCTCTCGGTCCGTCGCGCGCTATCCGTCGCTGAACAAGACCTTCCCAAAACTCGACGCGATTGTGTTAATGCCGGATA
    TTTACAGCTGGAGACGTTGGAGGAGAGCTTGGAGGAGCCAGGCGCGCGATAGGCAGCCGCGATAGGCCAGCTGTCTGGAAGGGTTTTGAGCTGCCTAACACGATTACGGCCCTAT 500
 81 N  V  D  L  C  N  L  L  S  V  R  A  L  S  R  R  L  N  K  T  F  P  K  L  D  A  I  V  L  N  A  G  I   113

FIG. 2A

```
501  GGGGGTTGGTCTGGCCTCTGCGTATGGAGGCGTTTGCACCGACGACGTGGCCAAATTGGCGCTGTAG    600
     CCCCCAACCAGACCGGAGTTAACCGGCATACCTCCGCAAAGTGGCTGTGCTGCACCGGTTTCATGTTTTAAGCGGACATC
114  G  G  W  S  G  L  N  W  P  L  A  V  W  S  V  C  T  D  I  I  H  A  T  T  W  P  K  Y  K  I  A  P  V  G  147

601  GTCTCAATACGGACAACCAGACAATTACTGTGACGACAAGGAGCCCCGCTCTTCGGCGAACCGTCTTCGGCCACTACATGCTCGCGCA    700
     CAGAGTATTGCCTGTTGGTCTGTTAATGACACTGGCTGTTCCTGGCGAGAAGACGCGGTTGCAGAAGCCGGTGATGTACGAGCGCGT
148  L  I  T  D  N  Q  T  I  T  V  T  D  K  E  P  R  L  G  T  V  F  C  A  N  V  F  G  H  Y  M  L  A  H  180

701  TAATGTCATGCCTCTTCTGCACCGATCCGATATGGCTCTCCAGCACTGAAGCCACGATCAACTTCTTCGATGTT    800
     ATTACAGTACGGAGAAGACGTGGCTAGGCTAGGCCGAGAGGTCGTGACTTCGTGCTAGTTGAAGAAGCTACAA
181  N  V  M  P  L  L  H  R  S  G  S  P  N  G  P  G  R  V  I  W  L  S  S  T  E  A  T  I  N  F  F  D  V  213

801  GATGATTTTCAGGCGCTCCGGTCCAAAGCTCCGTCATCGAGTCTACGAGTCATCAAAAGCGCTAACAGACCTTCACCTCAGACCTTCCAGTACTGCTCCCT    900
     CTACTAAAAGTCCGCGAGGCCAGGTTTCGAGGCAGTAGTCAGCATAGTTCGCGATTGTCTGGAGGATAGGGAGTGGAAGGTCATGACGAGGGA
214  D  D  P  Q  A  L  R  S  K  A  P  Y  E  S  S  K  A  L  T  D  L  L  S  L  T  S  D  L  P  S  T  A  P  W  247
```

1401 TTGGAGGCAGATGGAGGAGCTGAGGATCCTGTGGGATAACTTACTTGATGAAGAGAAGGGGGACTGGTGTGACGGGCGCTAGGTGGCTTGTCCTGGGAGTG
     AACCTCCGGTCTACCTCCTCGACTCCTAGGGACACACCCTATTGAATGAACTACTCTCTCTCCCTGACCACACTGCCGCATCCACGAACAGGACCCTCAC

1501 AGATCTCTTACATTTCGGCCTTGTCCCCTAAATCCTTTCTCCCCTCCGTTTATTATACGATGTCGGCGGTTTTATGTTCAATACAGGACACATCTACGG
     TCTAGAGAATGTAAAGCCGGAACAGGAGGATTTAGGAAAAGAGGAAGCAAATAATGCTACAGCCGCCAAAATACAAGTTATGTCGTGTAGATGCC

1601 TACAAAGACAACATATAGCTAATATATATAGTAATAATCAAGCACAAAAGCTCGATTCTGCAAGATCTCAATATCTTTATTCCAGTTTT
     ATGTTTCGTGTATATCGATTATATTATAGTATCTATATTAGTTCGTGTTTCGAGCTAAGACGTTCTAGAAGTTATAGAAATAAGGTCAAA

1701 CACTGCTCTTGTCTTCCATATTTACATTCCACGTCCACGTGCATCCTTTAAAAACAGT 1758
     GTGACGAGAACAGAAGGTATAAATGTAAGGTGCAGGTGCACGTAGGAAATTTTTGTCA

FIG. 2D (SEQ ID NO:7)
1   GAATTCCTGTGATGAGCAGAACCTCGGAGTATGCTCCGATGTCAGTACATTAAATTTTGTAGGCATCCACGTGATTCTATTTGGTCCGCAATAGGT
    CTTAAGGACACTACCTCGTCTTGAGCCTCATACGAGGCTACAGTCATGTCATGTAATTTAAAACATCGCTAGTGCACTAAGATAAAACGCAGGGGTATCCA (SEQ ID NO:9)
101 CTTCTGATACGGGCTGAAGAATATAGTACGTGGTCCAGTGCCTCAGGAAGTATTTTCGTACGGTTGGCTCCCAAGGCAATAGGTCAACCTCGCAT
    GAAGACTATGCCGACTTCTTATATCATGCACCAGGTCACGGATATCTGCCTTTCATAAAAGCATGCCAACCGAGGGTTCCGTTATCCAGTTGGAGGGTA

201 ACGGAGAATAACGGTACGGTCCTGAAGGAATGAGGGGATGTATTCTCCTTCCGAGGGCCAAGGGAACAGGCCCGACTGATCCGGCGAAAATTTC
    TGCCTCTTATTGCCATGCCAGGACTTCCTTACTCCCCTACATAAGAGGAAGAGGCTCCCGGTCTTCGTCCCCTTGTCCGGGCTAGGCCGCTTTAAAG

M  R  G  C  I  L  L  L  R  G  P  E  G  E  Q  A  R  T  D  P  A  K  I  S
1                                                                                                   24
                                                                                             (SEQ ID NO:8)

301 CCCTCTCGAGTCTTTCGCTCTCCCCCACACGGCTGACTAACCCTCCATTCTTGCCGATCCAGCCAGCCTTTTGTCGCCGCCCTTGGTTCCGG
    GGGAGAGCTCAGAAGCGAGAGGGGGTGTGCCGACTGATTGGGAAGGTAAGGTCGTCGGAAACAGGCGGCGGGAACCAAGCCC

25  P  L  D                                  (SEQ ID NO:30) L L S P P L V R A         36

FIG. 3A

```
401  CTACTGTCATCTTCCCTTCTTCATCTTCTGCCTCTGACTGAAATATTCAGTCGCCTCTGCATTACAGTTACTACGGCGCAGACCACGCTGCACAT   500
     GATGACAGTAGAAGGGAAGGAAGAGAAGTAGAAGTACGGCGAAGAGCTGACTTTATAAGTCAAGAGACTAAATGTCAATGATGCCGTCTGTGGACGTGTA
  37  T  V  I  F  P  S  S  S  C  R  S  R  L  K  Y  S  V  S  C  S  D  L  Q  L  L  R  A  D  T  L  H  I    69

501  CTCCGGATCATGACCGAATCACTCAGCAGGACCCGAATGCCAGCAACGATGGCCAGCGAATGCCCCCCGCCGACCCCGTTGAGGATTACGTCTCCCTGAA   600
     GAGGGCTAGTACTGGCTAGTGAGTTCTTGTCCCGTGCGCTAGGGCAAGCCCTACCCGGTCGCGCTTGGGCGACCAACTCCTAATGCAGAAGGGACTT
  70  S  A  I  M  T  E  S  T  Q  E  Q  G  N  D  G  Q  R  M  P  P  A  P  A  T  P  V  E  D  Y  V  F  P  E  102

601  TATCGCCTGAAGCGTGTGATGATGACCCGGAAAAGGACTCCTATTGCTTGGGTTCATTCTCACTTATTAGCTGTTCCTGACCTGCGCAATGT   700
     ATAGCGGACTTCGCACACTACTACGGCCCTTTCTGCGGCGATAACGAACGAATATGCAACCAAGTAAGAGTGGATAATGCAAGGACGTGGACGCGTACA
 103  Y  R  L  K  R  V  M  D  D  P  E  K  T  P  L  L  I  A  C  G  S  F  S  P  I  T  F  L  H  L  R  M  F  136

701  TCGAAATGGCCGCCGATTACGTCAAACTGAGCACAGATTTCGAAATAATTGGAGGTTATCTTCGCCCGTCTCGGACGCCTACGCCAAGGCAGTCTTGC   800
     AGCTTTACCGGCGGCTAATGCAGTTTGACTCGTGTCTAAAGCTTTATTAACCTCCAATAAAGCGGGCAGAGCCTCCGGATGGCGTTCCGTCCAGAACG
 137  E  M  A  A  D  Y  V  K  L  S  T  D  F  E  I  I  G  G  Y  L  S  P  V  S  D  A  Y  R  K  A  G  L  A  169

801  GAGTGCCAATCACAGTAGTTACTTTAACACACTTCTTCCATAGTTACTATCCAGGACTGATCTGGCCGGCTTTAGAATGCAATGCCAACGAGCCGTG   900
     CTCACGGTTAGTGTCATCAATGAAATGTGTGAAGAAGTATCAATGATAGGTCCTGACTAGAGTCCGCGAAATCTTAACGTTACGGTTGCTCGGCAC
 170  S  A  N  H  R                                                 I  A  M  C  Q  R  A  V                 182
```

(SEQ ID NO:31)

FIG. 3B

```
901  GACCAAACGTCAGACTGGATGATGGTGGATACATGGGAGCCGATGCACAAGGAGTACCAGCCAACTGCCATCGTACTGGATCATTTTGACTACGAGATCA  1000
     CTGGTTTGCAGTCTGACTACTACCACCTAGCTGTACCCTCGGTGTCCTCATGCATGATGCGTACGGTGACGACTAGTAGTAAAACTGATGCTCTAGT
183   D  Q  T  S  D  W  M  M  V  D  T  W  E  P  M  H  K  E  Y  Q  P  T  A  I  V  L  D  H  F  D  Y  E  I  N   216

1001 ACACTGTCCGCAAAGTGTATCGATACCGGAAAAGGACTCGAAGTGCTCGTCCGAAAGCGAGTGCAAGTTGGTCCATACCATGTCTACGCC  1100
     TGTGACAGGCGTTTCCATAGCTATGGCCTTTCGCTCAGCGTTCGCTCACGTTCAGAGCTTCGCTTCGAGCGCTCTAAACCAGGTATGTACAGATGCGG
217   T  V  R  K  G  I  D  T  G  K  G  T  R  K  R  V  Q  V  V  L  L  A  G  A  D  L  V  H  T  M  S  T  P   249

1101 CGGAGTATGGAGTGAGAAGGATCTCGATCATATTCTTGGACAGTACGGGTATGTTATGTGTATCTATCCTAACTTCGGCGAAGCTAACTGGTCTAGA  1200
     GCCTCATACCTCACTCTTCCTAGAGCTAGTAGTATAAGAACCTGTCATGCCCATACAATACAACATAGATAGGATTGAAGCCGTTCGATTGACCAGATCT    (SEQ ID NO:32) T
250   G  V  W  S  E  K  D  L  D  H  I  L  G  Q  Y  G                                                       266

1201 CTTTCATCGTCGAGCGAAGCGGGACAGATATTGACGAGGCGCTCGCGGCCATTGCAGCGCGCCGAGCCTTCGCGCTCGTCTATAACTGCCT  1300
     GAAAGTAGCAGCTCGCTTCGCCCTGTCTATAACTGCTCAGCCGCCGTAACGTCGGTACCTTTTCTTATAGGTACAATTGTTGAATAAGTTT
267   F  I  V  E  R  S  G  T  D  I  D  E  A  L  A  A  L  Q  P  W  K  K  N  I  H  V  I  Q  Q  L  I  Q  N   299

1301 TGACGTTAGCAGCACTAAGATTCGTCTTATTCCTCAGGCAGATATGAGCGTACTTGATCCCTGACCGGTGATGAGTACATCTATGAGAATAAC  1400
     ACTGCAATCGTCGTGATTCTAAGCAGTAATAAGGAGTCCGCTCTATACTCGATGAACTAGGAGACTGGGCCACTACTCATGATACTCTTATTG
300   D  V  S  S  T  K  I  R  L  F  L  R  R  D  M  S  V  R  Y  L  I  P  D  P  V  I  E  Y  I  Y  E  N  N   332
```

FIG. 3C

```
1401  CTCTACATGGATGACGGTACGACACAACCGACGGGCCGACGAGGACAAGGGCAAGACACGAGAGGAGCCCGGCCTTCAAATTAGCATTGCTCAAAAGCCAGATAA  1500
      GAGATGTACCTGCTGCCATGCTGTTGGCTGCGTTGGCCTGCCAGCCCGGCCCCGCCCGGGCCGGAAGTTTAATCGTAACGAGTTTTCGTCTATT
333     L   Y   M   D   D   G   T   T   Q   P   T   A   D   K   G   K   T   R   E   E   P   A   P   S   N   *   357

1501  GGCCACGCGACGACGTCATGACGACCATTGCTGGTTTCACGAAGATATCAAACCGCCGGAATGCAATCTCTGCGCTGATCTGAGCAAGCACTGATTC  1600
      CCGGTGCGCTGCTGCAGTAGCTGGTAACGACCAAAGTGCTCTATAGTTTGGCGGCCCGCCTTACGTTAGAGACGGACTCGTTCGTGACTAAG

1601  CGGTAAGCCGCAAGTTGGGGAGGATTTAATGAGCCCAACCGTATGGGTTTGTTCCGGTCAAGTCACTGGATTGACACGACGCCTTATGACTGTCATAT  1700
      GCCATTCGGGCGTTCAACCCCTCCTAAATTACTCGGGTTGGCATACCCAAACAAGGCCAGTTCAGTTCTGTGCGAATACTGACAGTATA

1701  CGACAGGTCCCCTCTCAGAGACCGGCCTACACAACAGTGATGCTGGCGTTCTTCTATTCCAAGCCCTCAACATCTAAGTGCAGGCGGCGAATTC  1792
      GCTGTCCAGGGAGAGGTCTCGGCCGGATGTGTTGTCACTACGACCGCAAGAAGATAAGGTTCGGGAGTTCGTAGATTCACGTCGCCGCTTAAG
```

FIG. 3D

(SEQ ID NO:10)

1   TTGCCTTCTTAGACTTGATATCTGAAGGAAGAGATCATCTGGTTGATGTACTGTATTAGGGGAGCACGTGATTATTCCCTCGATA   100
    AACGGAAGAATCTGAACTATAGACTTCCTCTTATTGCCTCTCGTAGACCAAACTACCATGACATAATGCCCTCGTGCACTAATAAGGGAGGCTAT
(SEQ ID NO:12)

101 GGCCAGTGGCTATGTCATAAGGAAGACTGACGCCTGAGGGGAAACACCTCCCGCCGAGTTCCATCTATACACTTCACGCTCGATCTCTCCAAG   200
    CCGGTCACCGGCATACAGTATTCCTTCTGACTGCCGGACTCCCCTTTGTGAGGGAGCTCAAGGTAGAATAGTGAAAGTGCGAGCTAGAGAGTTC

201 TTTCTGGCTTCATTGACTGAGTCGCGCCTTGCCTAGTGGTAGATTTAGATCTAGTGCAAATCACTTGCCTACATTCTGAACTGTTGTTCAGC   300
    AAAGACCGAAGTAACTGACTCAGCGGATCACCCATCTAAATCTAGATCAGCGTTTAGTGTTGAACGGATTAAGAGCTTGAACACAAGTCGG

301 TTGGCGGTTCCCCTGACTACTTATCTCTTCTTACCGTTTCGAAAACACTTCCTCCTGCGGGGAGACTAGTATCTATCGCCTGTCGCCCACTTTC   400
    AACGCCAAGGGAGAAGTGATGAATAGAAGAATGAAGATGCAAAGCTTTTGTGAAGGAGGCGACAGCCGGTGAAAG

401 ACCACCGTGTTTCACTAGGAGAATAGTGAAAGACTCAAGTCGTCTACCAAATGTGGTCATGTTCCGGTGCCGCAGAAGCGCAAGGAAGC   500
    TGGTGGCACAAAGTGATCCCTCTTATCACTTTCTGAGTTCAGCAGAATGGTTTTACACCAGTACCAAGGCCACCACCGGGCGGTCTTCCGTTCCTTCG

1   M  W  S  W  F  R  W  C  G  R  A  E  A  Q  G  S   16
(SEQ ID NO:11)

FIG. 4A

```
501  GCCGAAAACGCAATCCTCCAGTTCTCGAAGCCACCTTGACACTTGACATGCTGTACAGAAGGCGAGAAAGCACTTAGAAACCAATGAACGAACAGAGGCCATGCTA    600
     CGGCTTTTGCGTTAGGAGGTCGAAGCTCGGTGAACTCGTACGATGTCTTCGCGATCTTTTGGTTACTTGTTCTCCGGTA                              
17   A  E  N  A  I  L  Q  L  R  S  H  L  D  M  L  Q  K  R  E  K  H  L  E  N  Q  M  N  E  Q  E  A  I  A  K       50

601  AAAGAACGGTGACCACGAATAAGACGGTTCGTGTGTATATTATGGACCTTTATACAAGTCCCATGCTGATTGACCACCGCAGCCGCCAAAGCCGCC              700
     TTTCTTGCCACTGGTGCTTATTCTGCCAAGCACATATAATACCCTGGAAATATGTTCAGGGTACGACTAACTGGTGGTGGCGTCGGCGGTTCGGCGG
51   K  N  V  T  T  N  K  N  A          (SEQ ID NO:33) A  K  A  A  L                                              64

701  TCCGACGGAAAAGGTGCACGAGAAGAACTTAGAACAGACGCAGGCTCGAGATTGTACAGTCGAGCAGCAGATATACTCTATTGAGCGCCAATATTAA              800
     AGGCTGCCTTTTCCACGTGCTCTTCTTGAATCTTGTCTGCGTCCGAGCTCTAACATGTCAGCTCGTCGTCTATATGAGATAACTCGGCGGTTATAATT
65   R  R  K  K  V  H  E  K  N  L  E  Q  T  Q  A  Q  I  V  Q  L  E  Q  Q  I  Y  S  I  E  A  A  N  I  N         97

801  CCACGAGACCCTGGCCGCCATGAAGGCCGCCGGTGCAGCTATGAGAAGATTCACAACGGCATGACCGTCGAACAGGTCGACGAGACAATGTAGTCCCT             900
     GGTGCTCTGGGACCGGCGGTACTTCCGGCGGCCACGTCGATACTCTTCTAAGTGTTGCCGTACTGGCAGCTTGTCCAGCTGCTCTGTACATGACAGGA
98   H  E  T  L  A  A  M  K  A  A  G  A  A  M  E  K  I  H  N  G  M  T  V  E  Q  V  D  E  T  M            127

901  TACTGTACCGCTGGTGACATACCGGAATTGGCACTGTAACAGACTCAGGAGGACAAACTGCGGGAACAACAAGCCATCAACGACGAAATCGGATTGCCATC            1000
     ATGACATGGCGACCACTGTATGGCCTTAACCGTGACATTGTCTGAGTCCTCCTGTTTGACGCCCTGTTGTTCGGTAGTGCTGTTTAGCGCTAACGGTAG
128  Y  C  V  D  I  P  E  L  A  L  N  R  L  R  R  T  P  V  P  D  K  L  R  E  Q  Q  A  I  N  D  E  I  A  I  A  I   144
                                                        (SEQ ID NO:34)
```

FIG. 4B

1001 ACAAACCCGGGGTTCGGCGAGCAGGTGGACGAAGAGATCTGAGGCGGAACTGAGGCAGGAGGCTATGACGAGGCATGACGAGCTCCACACAG   1100
     TGTTTGGGCCCCAAGCGGCTCGTTCCACCTGCTTCTTCTAGACTCCGCCTTGAGCTCCGCCTCCGATACCTGCTCCGTACGAGGTGTGTC

145  T N P G F G E Q V D E E D L E A E L E G M E Q E A M D E R M L H T G   178

1101 GCACAGTACCAGTTGCAGATCAGCTCAATCGGCTACCTGCGCCAGCAATGCAGAACGTAAGGCTCTCCCTTTCCCACCTCAAAGCGAACTCCGACTGA  1200
     CGTGTCATGGTCAACGTCTAGTCGAGTTAGCCGATGACGCGGTCGCTTACGTCGAGTCATTCCGAGAGGGAAAGGGGTGGAGTTTTCGCTTGAGGCTGACT

179  T V P V A D Q L N R L P A P A N A E P   197

1201 CAGCCTTCCAGCCGCCGCCAAAGCCAAAACAGAAGGAAGAAGAAGAAGCAGGAGGTTGGAGAAGTTACGGCCGAAATGGCCGAAATGTGAGAGTGGTCC  1300
     GTCCGGAAGGTCGGCGGCGGTTTCGGTTTTGTCTTCCTTCTTCTTCGTCCTCCAACCCTCTCGGCTCAACCTCATGCCGGCCTTTACGGCTACACTCTCCAGG

198  A K A K Q K A E E E D E E A E L E K L R A E M A M *   222
(SEQ ID NO:35)

1301 TGGTGCTTTGGTCTCTTGGTCTAACTTTAATCTTTAATCTTTCTCCCCTACACATATGAATGAACAGGAATCGTTATCATGACGCACTAGGATTAGCCAAG  1400
     ACCACGAAACCAGAGAACCAGATTGAAATTAGAAAAAAGAGGGGATGTGTATACTACTGTCCTTAGCAATAGTACTGCCGTGATGCTAATCGGTTC

1401 CACTGTGTTCTTTTTCCGTCGGCTCGTTGCGCATCCTTCCTCTCGGCGTAATTACTTATCTAGTTGTACAACTACCCCGCGGAGCTTCTGTTGAGG  1500
     GTGACACGAAAAAGGCAGCCGAGCAACCGTTAGGAAGAAGAGGCGCCGCATTAATGAATCAACATGGTTGATGGGCGCCTCCGAAGACAACTCC

FIG. 4C

1501 CGAGAGCGAAAGCCCAGACGTGTCGCCCTTGCCCTGATTACTGGCCACTCCCGTCCGAGCACGCTACCTCCGTTCTGTCCACGCTGTATCCACTCTG 1600
     GCTCTCGCTTTCGGGTCTCTGCACAGCGGGAAACGGGACTAATGACCGGTGAGGCAGGCTCGTGCATGGAGGCAAGACAGTGCGACACTAGGGTGAGAC

1601 TAATAATCTACCAAGTGAATACTTTCTGGATGATTTGAAGGGCCTATGTTTCCTACGGCATCATGTCATTAGATATATGTTTTGTGGATCATGTTTCCCA 1700
     ATTATTAGATGGTTCACTTATGAAAGACCTACTAAACTTCCCGGATACAAAGATGCGGTAGTACAAACACCTAGTACAAGGGGT

1701 GCGCAATTGATGCCCATTTGCAGTTCACACTCGTCTCATATGAACCTCAGATAATATGAAAGCCGCTTCTCACCCAGCAAAACGTCACTGAGGATTAAAT 1800
     CGCGTTAACTACGGGTAAACGTCAAGTGTGAGCACAGTATACTTTCGGAAGAGTTGGGTCGTTTTGCAGTGACTCCTAATTTTA

1801 TGAGTAATTGAGTAAAACTAAATTAGTAGCTAGATAACTCCACCAGACCTAACACCGTCCAAACAGATAATCAACAAGGAAAAGAAGAAA 1899
     ACTCATTAACTCATTTTGATTAATCATGGATCTATTGAGGGGCAAGGGTCGATGTGGCAAGGTTTGTCTATTAGTTGTTCCTTTCTTTCTTT

```
22801  ATTGGAAAGACTTACCGTAGAATTGCCTTCCTCTTCGGGCTAGTATTATTGTACTGTTTGGATATATATAACGAAATGCTGAAGAACTTTC   22900
       TAACCTTTCTGAAATGGCATCGTAACGGAAGGAGAAGGAAGCCCGATAAATAACATGACAAACCGATATTAATAATATATATGTCTTTACGACTTGAAAGC
366    I  N  K  D  F  T  V  E  I  A  F  L  F  R  A  I  Y  L  Y  C  L  D  N  N  I  T  E  M  L  E  E  N  F  P   399

22901  CAGAAGCCTCAAAATTATCCGAGCATTTAAACCATTTATCTCTCAGATATCATCACAACGACATTCTAATGACTCCAGTTTGATTATAA    23000
       GTCTTCGGAGTTTTAATAGGCTCGTAAATTGGTAATAGAGAGTCTATAGTAGTTGCTGTAAGATTACTGAGAGTCAGGTCAAACTAATATT
400    E  A  S  K  L  S  E  H  L  N  H  Y  I  L  L  R  Y  H  H  N  D  I  S  N  D  S  Q  S  H  F  D  Y  N   432

23001  CACTTTAGAGTTTATTATTGAGCAACTATGCCGCCGAAGGTATAGCGATATGATGGTTGGAAGGAGATCGATGCTTACAGTGTACGAAAT    23100
       GTGAAATCTCAAATAATAACTCGTTGATACGGCGGCTTCCATATCGCTATACTACTACCAACCTTCCTCTAGCTACGAATGTCACATGCTTTA
433    T  L  E  F  I  E  Q  L  S  I  A  A  E  R  Y  D  Y  S  D  E  V  G  R  R  S  M  L  T  V  V  R  N   465

23101  ATGCTGGCCTTACTACACTCTCCGAACCTCTTATTAAAATTGGTATTCGTGTAATGAAAAGATTTGTAACAATGGCAA                23200
       TACGACCGGAATGATGTGAGAGGCTTGGAGAATAATTTTAACCATAAGCACATTACTTACTTTTCTAAACATTGTACCGTT
466    M  L  A  L  T  T  L  S  E  P  L  I  K  I  G  I  R  V  M  K  S  L  S  I  N  E  K  D  F  V  T  M  A  I   499

23201  TAGAAATCATTAATGATATTAGAGACGACGATATTGAAAAACAAGAAGAAGAAAATAAAAGCAAGAAGATTAATCCAGAAATGACTTCCGT   23300
       ATCTTTAGTAATTACTATAATCTCTGCTGCTATAACTTTTTGTTCTTCTTCTTTATTTTTCGTTCTTCTAATAGGTTGTCTTACTGAGGCA
500    E  I  N  D  I  R  D  D  D  I  E  K  Q  E  E  E  N  K  S  K  K  I  N  R  R  N  E  T  S  V   532
```

FIG. 5D

```
23301  CGATGAAGAGGACGAAACGGCACACATAATGACGAAGTTAACGAGGATGAAGAGAAGTTAACGAGGATGAAGAAGACGACAATATTTCATCTTCCATTCTCTGTAGAAACTTAGTG  23400
       GCTACTTCCTCCTGCTTTGCCGTGTGTATTACTGCTTCTCGTGTTATAAGTAGGAAGTAAGACATCTTTGAATCAC
533    D  E  E  D  E  N  G  T  H  N  D  E  V  N  E  D  D  N  I  S  S  F  H  S  A  V  E  N  L  V          565

23401  CAGGGAAAACGGCAACGTATCTGAGAGTACACATAAATAATATCTCCCACCGAAAAGGAAGGTCCTCAGCAACAATTGTTCTGTCTTACAACGTCAT                              23500
       GTCCCTTTGCCGTTGCATAGACTCTCATGTGTATTATTATAGAGAGGGCTTTTCCTTCCAGAGAGTCGTTGTTAACAAGAGACAGAATGTTCCAGTA
566    Q  G  N  G  N  V  S  E  S  D  I  I  N  N  L  P  P  E  K  E  A  G  S  A  T  I  V  L  C  L  T  R  S  S    599

23501  CATATATGCTAGAACTAGTAACACACCGTTAACAGAAAACATTTAATTGCGTGTCGTTGATGACACTTGATCACCAGCGGTTAGAAATACCGCGCC                              23600
       GTATATACGATCTTGATCATTGTGGCAATTGTCTTTTGTAAATTAACGCACAGCAACAAATGCTGTGAAACTAGTGGTCGCCAATCTTATGGCGGG
600    Y  M  L  E  L  V  N  T  P  L  T  E  N  I  L  I  A  S  L  N  D  T  L  I  T  P  A  V  R  N  T  A  P       632

23601  AAATATTAGGGAGCTTGGTGTCAAGAACCTTGGTTATGTTGTCTCCTTGGATGTGAAGTTGGCTATTCATAACATGTACATCTAGTATCTCCGTTCG                              23700
       TTTATAATCCCTCGAACCACACAGTTCTTGGAACCAATACAACAGAGAACCTACACTTCAACGATACATATGTACATGTACATAGTAGATCATGACGCCAAGC
633    N  I  R  E  L  G  V  K  N  L  G  L  C  C  L  L  D  V  K  L  A  I  D  N  M  Y  I  L  G  M  C  V  S       665
```

FIG. 5H (SEQ ID NO:16)

1   TCTTTGGTGTCAATGGTGTATTAATTCCGAGTTACTCCGAGTTACTCCAGGTCTAGGTTCCAAGAATGTACTTTATTTATTACACCGGAGCAAGTCATAT
    AGAAACCACAGTTACCACATAATTAAGGCTCAATGAGGTCCAATCCAAGTCCTCATGGTTCTTACATGAAATAAATAAATATGTGGCCTCGTTCAGTATA 100

(SEQ ID NO:18)

101 AATTACGCAAACGATTCGAAATTGTTAAAACAATTTCGTCTAAGCTTTAACAATTTCGTCCTAGTGCATAGAGTAAGAAAACTTTCTGCCCATTAGTCGAGTCGCACCCACATG
    TTAATGCGTTTGCTAAGCTTTAACAATTTCGTCTAAGCTTTAACAATTTCTGCCCATTAAGAAAACTTTCTGCCCATTAGTCGAGTCGCGGGGTGTAC 200

201 GATATCGTACTATTCGTATATGGAATGTAAATACTCGCAATACGATTYTATTTAGCTTCACAATCTCTCAAACTTATGTCTTGATCAATCTTTACGTT
    CTATAGCATGATAAGCATTACCTTACATTTTATGAGCGTTATGCTAAATATTTATGAGCGTTATGCTAAATAATCAGAACTAGTTAGAAATGCAA 300

301 TTACCAAATAATCGCCTGTTTCTGGCCATTTTTGCTTATACCATCTACCATACTCGCTGTCATGTGACGGTCATGGTCCATATGTGACGGTCTCAAGAAAAATAACAATG
    AATGGTTTATTAGCGGACAAAGACTGGAACAATGAGCGAGAATATATGACGACAGGTATACACTGCCACAGGTATACACTGCCACAGGTTCTTTTATTGTTAC 400

401 TAAATTGACCCAGCGGTGACGACAGTAGACTGTAAGTTATATGTACAATCATATCTTTCCTAGTCACTGTTAAGTAGGAGGAGGAGAGA
    ATTTAACTGGTCGGACTGCCACTGCTGTCATCTGACATCATGTTAGTATGAGATGGAATCGAATGTAGTATGAGATGGAAATCGACATTCATCTCTCTCT 500

501 GTTTAAGTGGAGAAGGCAAGAAAAAGTGCACTTATTACGTAATGGATCCACCAAGCACCGATTTTAAAGCCGCCACAGCCAAATGAAGAACTACAAC
    CAAATTTCACCTCTTCCGTCTTCTTTCACGTGAATAATGCATTACCTAGGGTGGTTCTGTGGGCTAAATTGGCGGTCGGTTTACTTGATGTTG 600

M D P T K A P D F K P P Q P N E E L Q P   20
    (SEQ ID NO:17)

FIG. 6A

```
601  CACCGCCAGATCCAACACATACGATATCCAAATCTGGACCTGATATCCTCATATGTTTTTAGCTGATTATTATATTCTTCGATGATGTCTCTTCGATCTCGA     700
     GTGGCGGTCTAGGTTGTGTATGCTATAGGTTTAGACCTGGACTATACAAATCGACTAATATTCTTCGAGAAGCTACGAGGAAGTTAGAGCT
21   P  P  D  P  T  H  T  I  P  K  S  G  P  I  V  P  Y  V  L  A  D  Y  N  S  S  I  D  A  P  P  N  L  D       53

701  CATTTACAAAACCCTGTCGTCAAGGAAAAAAAACGCCAACTCAAGGACCATATTCCATTAATACTAGTGACTTCCAGCCACTACTCTCGG               800
     GTAAATGTTTTGGGACAGCAGTTCCTTTTTTTTGCGGTTGAGTTCCTGGTATAAGGTAGTCATGATCACTGAAGGTCGGTGATAGAGCC
54   I  Y  K  T  L  S  S  R  K  K  N  A  N  S  S  N  R  M  D  H  I  P  L  N  T  S  D  F  Q  P  L  S  R       86

801  GATGTATCATCGGAGGAGAAAGTGAAGGCAATGAATTGAGCGTACTACTACAGGATGACTGGATGATTTGCGGGTACTGAAGAGCC                    900
     CTACATAGTAGCCTCCTCTTTCACTTCCGTTACTTAACTCGCATGATGTCCTACTACAATGCCTACTACTAGCCTTAAACCCCATGACTTCTCG
87   D  V  S  S  E  E  E  S  E  G  Q  S  N  G  I  D  A  T  L  Q  D  V  T  M  T  G  N  L  G  V  L  K  S  Q    120

901  AAATGCTGATTTGGAAGAAGTTCCTCACACAATTGTAAGACAAGCCAGAACTATTGAAGATTACGAATTCCTGTACACAGATTGACGAAAAGTTACA       1000
     TTTAACGACTAAACCTTCTTCAAGGAGTGTTAACATTCTGTTCGGTCGGTCTTGATAACTTGATGCTTAAGGACATGTGTCTAACTGCTTTTTCAATGT
121  I  A  D  L  E  E  V  P  H  T  I  V  R  Q  A  R  T  I  E  D  Y  E  F  P  V  H  R  L  T  K  K  L  Q       153
```

FIG. 6B

```
1001  AGATCCTGAAAACTGCCTCTGATCATTGTTGCTTGTGCATAACATACCTACATTTGAGAATGTTTGAAATGGCTTTAGATGATATC   1100
      TCTAGGACTTTTGACGGAGACTAGTAGCAACGAACACTAGTAAAAGAGGGTATTGTATGGATGTAAACTTACAACTTTACGAAATCTACTATAG
154   D  P  E  K  L  P  L  I  I  V  A  C  G  S  F  S  P  I  T  Y  L  H  L  R  M  F  E  M  A  L  D  D  I     186

1101  AATGAGCAAACGCGTTTGAAGTGGTTGGTGGTTATTTTCTCCAGTAAGTGATAACTATCAAAAGCGAGGGTTAGCCCCAGCTTATCATCGTGTCCGCA   1200
      TTACTCGTTTGCGCAAACTTCACCAACCACCAATAAAAGAGGTCATTCACTATTGATAGTTTTCGCTCCCAATCGGGGTCGAATAGTAGACAGGCGT
187   N  E  Q  T  R  P  E  V  V  G  G  Y  F  S  P  V  S  D  N  Y  Q  K  R  G  L  A  P  A  Y  H  R  V  R  M  220

1201  TGTGAATTAGCATGCGAGCGGACATCATCTGGTTAATGGTTGATGCCTGGGAAATCTTTACAATCAAGTATACAAGGACAGCAAAGTCTTGGACCA   1300
      ACACGCTTAATCGTACGCTCGCCTGTAGTAGACCAATTACCAACTACGGACATATAGTTCAATAAATGTTAGTTCCTGTCGTTTCAGAACCTGGT
221   C  E  L  A  C  E  R  T  S  S  W  L  H  V  D  A  W  E  S  L  Q  S  S  Y  T  R  T  A  K  V  L  D  H     253

1301  TTTCAATCATGAAATAAATATCAAGAGAGGTGAATCATGACTGTAGATGGTGAAAAATCATGTTATTGGCAGGCGGTGATCTTATC   1400
      AAAGTTAGTACTTTATTTAGTTCTCTCCACTTAGTACTGACATCTACCACTTTTTACCGCCATTTTAGTACAATAACCGTCCGCCACTAGAATAG
254   F  N  H  E  I  N  I  K  R  G  G  I  M  T  V  D  G  E  K  M  G  V  K  I  M  L  L  A  G  G  D  L  I     286

1401  GAATCCATGGGCGAGCCTCATGTGTGGGCTGATTCAGACCTGCACCATATTTTGGGTAATTATGAGTGTTGATCGTGAAAGAACTGGTTCTGATGTTA   1500
      CTTAGGTACCCGCTCGGAGTACACACCCGACTAAGTCTGGACGTGGTATAAAACCATTAATACTACAAACTAGCACCTTTCCTGACAAGACTACAAT
287   E  S  M  G  E  P  H  V  W  A  D  S  D  L  H  H  I  L  G  N  Y  G  C  L  I  V  E  R  T  G  S  D  V  R  320
```

FIG. 6C

```
1501  GGTCCTTCTTGCTTTCCCATGATATCATGTATGAACACAGAAGAGAAATATCCTTATTATCAACAACTATTACAATGATATTCCTCAGAAGTGCG  1600
      CCAGGAAGAACGAAAGGGTACTATACATGTGTCTTCTTTATAGGAATAATAGTTTGTTGAATAAATGTTACTATAAGGAGATGTCTTCAGGC
321    S  P  L  L  S  H  D  I  M  Y  E  H  R  R  N  I  L  I  I  K  Q  L  I  Y  N  D  I  S  S  T  K  V  R     353

1601  GCTTTTCATCAGACGTGGAATGTCAGTTGTTAGTACCTTACAGTCAAGTTATAGAAGAAGGTTTGAGACAGTTCTCATATTAGATATGTTTCACTTGGC  1700
      CGAAAAGTAGTCTGCACCTTACAGTCAACTATCTCTTCCAAACTCTGTCATCCGTTACATCCAAGAGTATAATCTATACATTAATCAAGTGAACCG
354    L  F  I  R  R  G  M  S  V  Q  Y  L  L  P  N  S  V  I  R  Y  I  Q  E  Y  N  L  Y  I  N  Q  S  E  P     386

1701  GTCAAGCAGGTCTTGGATAGCAAAGAGTAGTTATTACAACTCTGATACTGCAGCAGTTCAAATTACCACTTCCTCTTCAAGGTGCATAGAAAAAA  1800
      CAGTTCGTCCAGAACCTATCGTTTCTCACTCAATAATGTTGAGACTATGACGTCGTCAAGTTTAAATGGTGAAAGGAGAAGTTCCAGTATCTTTTTT
387    V  K  Q  V  L  D  S  K  E  *                                                                      395

1801  GTTCCTGGATGCACGAGTTAAATGTTTACAGCAGAGCAACAATCATGTGAACAATGTCAAACATTTATTTTAACACTTAATAATTATATATAACCACA  1900
      CAAGGACCTACGTGCTCAATTTACAAATGTCGTCTCGTTGTTAGTACACTTGTTACAGTTTGTAAATAAATGTGAATTATTAATATTATATATTGGTGT

1901  CCAGGCGGTAAGTTTCATAAGGAAAAACCTTTCAGTGAAGTCTGTTTAATCAGCAACAAATTAGCTTATAAATACAGAATCCGAAGA  2000
      GGTCGCCATTCAAAGTATTCCTTTTGGAAAGTCACTTGTTTAATCGAATCTTAATTGAGCAATATTTATGTCTTAGGCTTCT

2001  TACTGATCCTACTCGGCGTTACTATTAATGCGGGTAATGATCTATAGTAACTTAAAAGTCTTGTATAATATTGAATTTGCACGTCTATAGTAACAA  2100
      ATGAACTAGATATTATGACGTTATATCGGGATAGTTAGCCCATTACTAGATATCATGCAGATATCATTAAAACTTAAACTTCATTGTT

2101  TGCCGTATAATAACTGCATAATAGCCCTATCAATCGGAATATACCAAAACATCCTTT  2156
      ACGGCATATTATGACGTATTATCGGGATAGTTAGCCTTATAATATGGTTTTGTAGGAAA
```

FIG. 6D

(SEQ ID NO:19)
28401 GTTTGAATGTGTTTGTGTTAGAAATTTGTGTGCTTTAATGTTATGTTATAATGAAATCTTATTAGATTTATTAACGTTTTGCTGTGCTTATATATAA 28500
CAAACTTAACACAAACACAATCTTAAACACACGAAATTACAATACAATATTACTTTAGAATAATCTAAATAAATTCCAAAAACGACACGAATATATTT (SEQ ID NO:21)
28501 CATTACATAATAAAAGGAGTAGAGAGGAGTACAAATCTACCTGCCAGAACTCTCTCCTATATATATATATTTCCAGTGGTGTCTGATTA 28600
GTAATGTATTATTTCCTACCATCTCTTCACCATCTCTTCACCATCTTAGATGGACGGTCTTGAGAGAGGAATATATAAATAAGTCACACAGACCTAAT

28601 CCTACCTCAAGCCATCCATATCCATATCCATATAACGCCTACAAAATTTCTACCCAATCAGCAGCTTCTATCACTATTCTGTATACCACCATA 28700
GGATGGAGTTCGGTTCGTATGGTAATGGTATAGGGTATATGGTATATAGGTATATAGGTATATAGGTATGGGTCGAAAGATAGTGATAGGACCATATGGTAT

28701 GGCACCACCACTGTTTGTGTAAATTTACTCCTGAGGGGGGGGTGGCTCAACACGGTGTAGCCCTTCTCCCGCACAACCCGATGAAACCCACAATCGCC 28800
CCGTGGTGGTGACAAACATTTAAATGAAGGACTCCCCCCCACCGAGTGTGCCACATGTGCCACATCCGGAAGAGGGCGTGTTAGCTACTTGGCGTGTTAGCGG

28801 TCCGTCTCTTCCACTGTGCACGGCGCTAGCTCAACATCTTCCCCGCCACATTTACTGTGTGGCAAGAAGTGCATAATCTAAAAAACATACGTATGAGAA 28900
AGGCAGAGAAGGTGACACGTGCCGCGATCGAGTTGTAGAGTGTAAATGACACCGTTCTTCCACGTATTAGATTTTTTTGTATGCATACTCTT

28901 TGGAAAGGGCAAGATAATATCGGACCGTAGTGAGTCACTTGCTTTTGTATTGCAACCAACTGCCGCCCCCTCTTCCCGCTCTTGCACCAAAAACGCTAAAT 29000
ACCTTTCCCGTTCTATTATAGCCTGGCATTCACTCAGTGAACGAAAACATTAACGTTGGTTGACGGCGGGAGAAGGCGAGAACGTGGTTTTGCGATTA

FIG. 7A

```
29001  GCCCATTGTGATGGCTCATCACCCTCACGACGAAGTAAGACCCGGGGCACAAGAAATACGAGATCATAACAGTTCGAGTCCGTTTATTGTGTGCGGTT   29100
       CGGGTAACACTACCGAGTAGGTGGGAGTGCTGCTTCATTCTGGGCCCCGTGTTCTTTATGCTCAGTATGTCAAGCTCAAGCTCCAAATAACACAGCCAA

29101  TTGGTACGCTTTTCGTGAGGTGTACTACCATTCATGAGAGTCGTTTAGGAGCTGTCATGAAAGATATGTATCTGTTGATGAACTGTAAAATTTGCA   29200
       AACCATGCGAAAAGCACTCCACATGATGGTAAGTACTCCTCGACAGTACTTTCTACACATAGAACAACTACTACTTGACATTTTTAAACGT

29201  GAAATTGCGCTATTCCGTTTATTTCATTGTCGATTCGGTCGTGTTAATATTAGGGGTACAAAATATACTAGAGAGTTCTCCCTGAGGATATGGAATGCGCAA   29300
       CTTTAAGCGGATAACTACACTGTGTTTAAACCTGTTATATTGCTAAGTAATAAATCGTTTATATTGCTAAGTTAATGCTGCGAATCCTATATCCTTACGCGTT

29301  ATGGGCATTTGATGTGACACACAAATTTGGACAATATAACGATTCATTTTTAGATCGTGTGTCAACCGTCCAGTGGCCAGTGGCCAGCCTCCCAGTGGCCGAGTGGTTAAGGCGATGCCTGC   29400
       TACCCGTAAACTACACTGTGTTAAACCTGTATATTGCTAAGTAATAAATCGTTTATATTGCTAAGCAACAAGTTGGCAGGGTCACCGGCTCACCAATTCCGCTACGGACG

29401  TATTTCCTCAGAAAAGCAATTAGGCATTGGGTTTACCTGCGCAGGTTCGAATCCGTCTGTGACGCTTTTTTAATTCTTTACTCCATGACAAAGCCG   29500
       ATAAAGGAGTCTTTTCGTTAATCCGTAACCCAAAATGACGGCGTCCAAGCTTAGGACAGACACTGCGAAAAATTAAGAAATGAGTACTGTTTTCGC
```

FIG. 7B

```
29501  GATAAAAATTCCCGCATTCCGGGGTAAAAAATCCGGTTTTTTTTAGCACTCGCTGTTTTGCCCTCTACCGGGTGAAAATGACGATGAAGACGCTCG
       CTATTTTTAAGGGCGTAAGCCGCATTTTTTAGGCCAATAAAAAAAATCGTGAGCGACAAAAACGGAGATGGCCACTCTTTTACTGCTACTCTGCCGACC    29600

29601  AATTGGCGTGCATCCGCTTACGTAGGATAGAACACCTTAGCGAACTTTATTGCTCGAAGATTCGCTATCCATATCTTTTAGTTTCCCCCCA
       TTAACCGCGACGTAGGCGAATGCCATCCTATCCTGTGGATGTTTCTAAATGCTTGAAATAACGAGCTTCTAAGCGATAGGTATAGAAAATCAAGGGGGT     29700

29701  TTTCACAATGGGATACCGTTGTTTTTTCTGTAGTACGCTTTCTCATAGTGTAATAGAGTCAGTAATTCATTTTTTGCAGAAAGGAATTCTTCAC
       AAAGTGTTACCCTATGGCAACAAAAAGACATCCATGCGAAAGAGTATCAATTATCTCAGTCATTAAGTAAAAACGTCTTTCCTTAAGGAAGTG         29800

29801  CTAATTTTAGAATTTCATCAACATTTATTGTATCTGCATGTATAACAAATTAGAAAAATTTGGAAGGAAAAAAAACTGTTGCGTCAATTACTTATACC
       GATTAAAATCTTAAGTAGTTGTAAATAACATAGACGTACCATATGTTTAAATCTTTTTAAACCTTGTTTTTTTTGACAACGCAGTTAATGAATATGG     29900

29901  AGGGATAGAAAAAAAAGGAAACATGGAAACATGGATCTCCGGATTCAAACCGCCATCTGCAGACGAGGAATTGATTCCTCACCGACCCGAA
       TCCCTATCTTTTTTTTCCTTTGTACCTTAGGGTGTTCTCGAGGCCTAAAGTTTGGGCGGTACTAAGGAGGTGGGCTGGGCTT                   30000

1    M  D  P  T  R  A  P  D  F  K  P  P  S  A  D  E  E  L  I  P  P  P  D  P  E    25

(SEQ ID NO:20)

```
30501  CTCTGAACAACAAGGTTTGAAGTCATAGAGTCATATTACTCCCCGTGTAGTGATAACTATCAAAGCAAGGCTTGGCCCCATCCTACCATAGAGTACGT  30600
       GAGACTTGTTGTTCCAACTTCAGTATCTCAGTTCTCAGTAGAAGTCAGTAGTAGAGGGACAATCACTATTGATAGTTTCGTTCCGAACGGGGTATCTCATGCA
193    S  E  Q  T  R  P  E  V  I  G  G  Y  Y  S  P  V  S  D  N  Y  Q  K  Q  G  L  A  P  S  Y  H  R  V  R    225

30601  ATGTGTGAATTGGCTGCTGCGAAAGAACTCATCTGGTTGATGGTGTAGTTGATGGAGTCATTGCAACCTTCATACACAAGAACTGCCAAGGTCTTGATC  30700
       TACACACTTAACGGACGACGCTTTCTTGAGTAGACCAACTACCACCATCAATGAAGTAGGACGTTGGAAGTATGTTCTTGACGGTTCCAGAACTAG
226    M  C  E  L  A  C  E  R  T  S  S  W  L  M  V  D  A  W  E  S  L  Q  P  S  Y  T  R  T  A  K  V  L  D  H  259

30701  ATTTCAATCACGAAATCAATATTAAGAGAGGTGGTAGCTACTGTGTTGGAGAAAAATTGGTGCTGGCTGGTGGTGACCTAAT  30800
       TAAAGTTAGTGCTTTAGTTATATATTCTCCACCATCGATGACAATGACCTCTTTTTTAACCACGACCGACCACTGGATTA
260    F  N  H  E  I  N  I  K  R  G  G  V  A  T  V  T  G  E  K  I  G  V  K  I  M  L  L  A  G  G  D  L  I    292

30801  AGAGTCAATGGGTGAACCAACGTTTGGGCCGGACGCCGATTTACATCACATTCTCGGTAATTCGGTTGTTTGATTGTGAACGTACTGGTTCTGATGTA  30900
       TCTCAGTTACCCACTTGGTTTGCAAACCCGGCCTGCGGCTAAATGTAGTGTAAGAGCCATTAATGCCAACAACTAACAGCTTGCATGACCAAGACTACAT
293    E  S  M  G  E  P  N  V  W  A  D  L  H  H  I  L  G  N  Y  G  C  L  I  V  E  R  T  G  S  D  V    325
```

31501 GCGCTGTAAATAATGATGAGGCAGGAAAATGTTATCTGCTTGGACTTCAACCGACTCTAATTCATTATATAT 31600
      CGGGACACATTTATTACTACTCCGTCCTTTTAACAATAGACGAACCTGAAGTTGGCATGCGTAACTCCCTGGCCTTAGTTGGCTGAGATTAAGTAATATATA

31601 TCCACTGCTACCACCTGGAATGTTGAAAGTATGTTTCTCCTAGCAAAATTAAAACCCATCCGTGAATGAAGCGTTACTACTAATAACTGGTAGCTTT 31700
      AGGTGACGATGGTGGACCTTACAACTTTCATACAAAGAGGATCGTTTAATTTGGGTAGGCACTTACTTCGCAATGATTATATTGACCATCGAAA

31701 GTCACTCGTACCAGGAAAAGTGAAGATTAAACTGAATTTTAAA 31743
      CAGTGAGCATGGTCCTTTTCACTTCTAATTTGACTTAAAATTT

FIG. 7G (SEQ ID NO:22)
15901 TTCTACTACTCAGTACAAAAAGCACGCTGCTTATTATAACTTTGTGCCACAGAATATCAACATCAAATATCAA 16000
      AAGATGATGAGGTCATGTTTTTCTGGTGACAGAATAAATAAATGAAAACAGGTGTTCTTACTAGTTGTATTTATAGTTGAATCATAGACGTTC (SEQ ID NO:24)
16001 CACATCTGCTCACGGAACTAAACCCGTTGAGCAGTGCCCCGACGCCAAAACAGCCAAGCAAGATT 16100
      GTGTAGACGAGGTGCCTTGCATTGGCAATCTGTCACGGCCACTCTGCAAGGTTAAGCCTAATTGATAGGGTTTGTTGGTCGTTTGTTCTAA

16101 CACGAACCGGCCCTCGTTTGACCCAAGCCCGTTAACGACAAGATCGGAGCAAGCATGGGAACCACTCCCAGCAAT 16200
      GTGCTTGGCCGGGCGGCAACAAACCTGGGCTTCCCCGGGTAAATTGCCCGGGGTCGTGGTTCTAGCGTGGTGGTCGTTGGTGTCGTGTA

16201 CACTGCACGGAGAACAATAACTAGAAACATGCGAGATACCGAGGATAACCGGGCATCACGACACAATCAACAGCGTGGAAG 16300
      GTGACGTGCTGTGTTATTGAATCTTGTACCGTCTATGCCGTAGGACGTCCTAGAGAGCACTAGCTAGTGTGTAGTTGGTGTCCCGAGCCTTC

16301 AAGATGGTTACCTCAGGACGACAGTCACTGACGAGCTCAATGGGAAGAGTCGGTGCAACAGTTGAACAAGCTGCT 16400
      TTCTAACAATGAGTCGTCTGCTGCAGCCCAAGTTACCGTTGTCCAGTTACCGTTGCCAGTTACCGTGGCCAGTCTTCAGGACGTGTCAACTTGTTCGACGA

16401 CAACTGGGTCCTCCTGCCCCTGCTGGGCAAGTATATAGGTAGGAGAATGCCCAAGACTCTATGGAGGTCATTGAACACTTTGTATAAGTGTTTGTT 16500
      GTTGACCCAGAGACGAACCGGGAACCACCGGTTACCGGTTCTGAGATACCTTCATCATCTTCTTCAAGTAACTTTGTGAAACATATTCACAAACAA

```
16901  GGATTTGGAAATAGACTTTGATTATCTGATTGGTGGACTTCACCAACTAGTGTGAGTGTTTGAACGGCATATTACGACATCAACATGGTGAGGGCGATA   17000
       CCTAAACCTTTTATCTGAACTAATAGACTAACCACCACCTGAAGTGGTTGTACCACTGACAGAACTTGCTATAATGCTGTAGTGTTTTCATGTCCGGCTAT

64     D  L  E  I  D  F  D  Y  L  L  V  D  F  T  N  K  V  S  V  L  N  A  Y  Y  D  I  N  K  K  Y  R  A  I      96

17001  AACTACCTTTTCGTGAATGCTGCGCAAGGTATCTTTGACGGTATAGATTGGATCGGAGCGGGTCAAGGAGGTTTTCACCAATCCATTGGAGCCAGTGACAA   17100
       TTGATGGAAAAGCACTTACGACGCGTTCCATAGAAACTGCCATATCTAACCTAGCCCTCCAAAGTGGTTAGTAAACTCCGTCACTGTT

97     N  Y  L  F  V  N  A  A  Q  G  I  F  D  G  I  D  W  I  G  A  V  K  E  V  F  T  N  P  L  E  A  V  T  N     130

17101  ATCCGACATACAACTGGTGGGCGTCAAGTCTAAAGATGACATGGGGCTTATTTTCCAGGCCAATGTGTTGGTCCGTACTTATCAGTAA   17200
       TAGGCTGTATGTTCTATGTTGACCACCCGCAGTTCAGATTCTGAATTTCTACTGTTACTCGAATAAAGGTCCGGTTACACAACGGGCATGAATGTAGTCATT

131    P  T  Y  K  I  Q  L  V  G  V  K  S  K  D  D  H  G  L  I  F  Q  A  N  V  F  G  P  Y  Y  F  I  S  K     163

17201  AATTCTGCCTCAATTGACCAGGCGAAAGGTCTATATTGTTTGGATTTCGAGTATTATGTCCGATCCGATCTTAGTATCTTTCGTGAACGATATTGACTACTA  17300
       TTAAGACGGAGTAACTGGTCCGCTTTCCAGATATAACAACCTAAAGCTCATAATACAGGCTAGAATTCATAGAAGCACTTGCTATAACTGATGAT

FIG. 8D

US 6,514,715 B2

ESSENTIAL FUNGAL GENES AND THEIR USE

RELATED APPLICATION INFORMATION

This application is a divisional of application Ser. No. 08/965,762 filed on Nov. 7, 1997 now U.S. Pat. No. 6,280,863, which is incorporated herein by reference in its entirety.

BACKGROUND OF THE INVENTION

The invention relates to essential fungal genes and their use in identifying antifungal agents.

Fungal infections (mycoses) may be cutaneous, subcutaneous, or systemic. Superficial mycoses include tinea capitis, tinea corporis, tinea pedis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections can also contribute to meningitis and pulmonary or respiratory tract diseases. Opportunistic fungal infections proliferate, especially in patients afflicted with AIDS or other diseases that compromise the immune system.

Examples of pathogenic fungi include dermatophytes (e.g., *Microsporum canis* and other M. spp.; and Trichophyton spp. such as *T. rubrum*, and *T. mentagrophytes*), yeasts (e.g., *Candida albicans, C. Tropicalis,* or other Candida species), *Torulopsis glabrata, Epidermophyton floccosum, Malassezia furfur* (*Pityropsporon orbiculare,* or *P. ovale*), *Cryptococcus neoformans, Aspergillus fumigatus,* and other Aspergillus sp., Zygomycetes (e.g., Rhizopus, Mucor), *Paracoccidioides brasiliensis, Blastomyces dermatitides, Histoplasma capsulatum, Coccidioides immitis,* and *Sporothrix schenckii*.

Various strains of the fungus Aspergillus sp. cause aspergillosis, a potentially life-threatening disease in humans and other mammals. The clinical manifestations of aspergillosis in humans are very similar to those observed in rodents and cows. For example, necrosis, angioinvasion, and hematogenous dissemination are common features of aspergillosis in rodent and bovine model systems and in humans. In humans, aspergillosis typically is caused by inhalation of conidia (i.e., asexual spores produced by the fungus). In cattle, pathogenic Aspergillus typically enter the animal through the forestomach and then disseminate through the blood of the animal. Putative virulence factors produced by pathogenic species of Aspergillus include hydroxymate siderophores (i.e., compounds that compete with human iron-binding proteins to acquire iron to support fungal growth), lipids having the ability to inhibit complement and phagocytosis, and proteinases that can degrade elastin and other substrates.

SUMMARY OF THE INVENTION

The invention is based on the discovery of four new genes in the fungus Aspergillus nidulans that are essential for survival. These genes are referred to herein as AN97, AN80, AN17, and AN85; for convenience, the polypeptides encoded by these genes are referred to herein as "AN polypeptides." The genes encoding the AN polypeptides are useful molecular tools for identifying similar genes in pathogenic microorganisms, such as pathogenic strains of Aspergillus (e.g. *Aspergillus fumigatus* and *Aspergillus flavus*). In addition, the AN polypeptides and the essential genes encoding them are useful targets for identifying compounds that are inhibitors of the pathogens in which the AN polypeptides are expressed. Such inhibitors inhibit fungal growth by being fungistatic (e.g., inhibiting reproduction or cell division) or by being fungicidal (i.e., by causing cell death).

The invention, therefore, features an isolated AN97 polypeptide having the amino acid sequence set forth as partial sequences in SEQ ID NOs 2 and 29, or conservative variations thereof. Nucleic acids encoding AN97 also are included within the invention. In particular, the invention includes an isolated nucleic acid of (a) SEQ ID NO:1, as depicted in FIG. 1, or degenerate variants thereof; (b) SEQ ID NO:1, or degenerate variants thereof, wherein T is replaced by U; (c) nucleic acids complementary to (a) and (b); and (d) fragments of (a), (b), and (c) that are at least 15 base pairs in length and that hybridize under stringent conditions to genomic DNA encoding the polypeptide as partial sequences in SEQ ID NOs 2 and 29.

The invention also features an isolated AN80 polypeptide having the amino acid sequence set forth in SEQ ID NO:5, or conservative variations thereof. Nucleic acids encoding AN80 also are included. In particular, the invention includes an isolated nucleic acid of: (a) SEQ ID NO:4, as depicted in FIG. 2, or degenerate variants thereof; (b) SEQ ID NO:4, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO:5.

The invention also includes an isolated AN85 polypeptide having the amino acid sequence set forth as partial sequences in SEQ ID NOs:8, 30, 31, and 32, or conservative variations thereof. Nucleic acids encoding AN85 also are included. In particular, the invention includes an isolated nucleic acid of: (a) SEQ ID NO:7, as depicted in FIG. 3, or degenerate variants thereof; (b) SEQ ID NO:7, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs:8, 30, 31, and 32.

The invention also features an isolated AN17 polypeptide having the amino acid sequence set forth as partial sequences in SEQ ID NOs:11, 33, 34, and 35, or conservative variations thereof. Nucleic acids encoding AN17 also are included. In particular, the invention includes an isolated nucleic acid of: (a) SEQ ID NO:10, as depicted in FIG. 4, or degenerate variants thereof; (b) SEQ ID NO:10, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs:11, 33, 34, and 35.

The invention also includes isolated nucleic acids that are at least 15 base pairs in length and which hybridize under stringent conditions to a nucleotide sequence selected from the group consisting of SEQ ID NO:1, SEQ ID NO:4, SEQ ID NO:7, and SEQ ID NO:10. In addition, the invention includes allelic variants (i.e., genes encoding isozymes) of the genes encoding AN97, AN17, AN80, and AN85. For example, the invention includes genes that encode an AN polypeptide but which gene includes point mutation, deletion, promoter variant, or splice site variant, provided that the resulting AN polypeptide functions as an AN polypeptide (e.g., as determined in a complementation assay, as described herein and elsewhere). Also included within the invention are isolated nucleic acid molecules containing the cDNA sequences contained with ATCC accession numbers 209473, 209472, 209484, and 209471(deposited with the American Type Culture Collection, 10801 University Boulevard, Manasses, Va. 20110-2209 on Nov. 19, 1997), as well as polypeptides encoded by the cDNA sequences of these nucleic acid molecules. encoded by the cDNA sequences of these nucleic acid molecules.

Identification of the AN97, AN17, AN80, and AN85 genes and the determination that they are essential allows homologs of these genes to be found in other organisms (e.g., fungi, such as yeast like *S. cerevisiae*; mammalian cells, such as human or murine cells; or plant cells). Thus, the AN polypeptides used not only can be as a model for identifying similar essential genes in other Aspergillus strains, but also to identify homologous essential genes in other organisms, e.g., *S. cerevisiae*. Because such genes are homologs, they can be expected to be essential for survival without the need for extensive characterization of the homologous gene or polypeptide. Even though some such homologous genes may have previously been identified, the invention allows one to determine that such genes are essential for survival. Having identified such homologous genes as essential, these genes and the polypeptides encoded by these genes can be used to identify compounds that inhibit the growth of the host organism (e.g., compounds that are fungicidal or fungistatic against pathogenic strains of the organism).

As used herein, the term "yeast" refers to organisms of the order Saccharomycetales, which includes yeast such as Saccharomyces and Candida. As described below, several homologs of the AN polypeptides have been identified in the yeast *S. cerevisiae* and are essential for survival. Given the identification of such genes as essential in *S. cerevisiae*, homologs of these essential yeast genes can also be found in pathogenic yeast strains (e.g., *Candida albicans*). The *S. cerevisiae* polypeptide and gene termed D9798.4 are homologs of the AN97 polypeptide and gene. The D9798.4 polypeptide and nucleic acid are depicted in FIG. 5, and are set forth in SEQ ID NOs:14 and 13, respectively (GenBank Accession No. U32517). As described herein, various methods of the invention can utilize the D9798.4 polypeptide or conservative variations thereof. Also useful are isolated nucleic acids of (a) SEQ ID NO:13, as depicted in FIG. 5, or degenerate variants thereof; (b) SEQ ID NO:13, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO:14.

Yeast homologs of the AN85 and AN80 polypeptides and genes also have been identified as being essential for survival, and these homologs can be used in the methods described herein. As described above for AN97, conservative variations, degenerate variants, complementary sequences, fragments, and nucleic acids in which T is replaced by U also can be used in various methods of the invention. Two homologs of AN85 have been identified. The amino acid and nucleic acid sequences of the AN85 homolog termed YGR010W are depicted in FIG. 6 (GenBank Accession No. Z72795); these sequences are set forth as SEQ ID NOs:17 and 16, respectively. The amino acid and nucleic acid sequences of the AN85 homolog termed L8543.16 are depicted in FIG. 7 (GenBank Accession No. U20618); these sequences are set forth as SEQ ID NOs:20 and 19, respectively. The AN80 polypeptide and gene have a homolog in yeast, termed L8004.2, the amino acid and nucleic acid sequences of which are depicted in FIG. 8 (GenBank Accession No. U53876). These sequences are set forth as SEQ ID NOs:23 and 22, respectively.

The term AN97 polypeptide or gene as used herein is intended to include the polypeptide and gene set forth in FIG. 1 herein, as well as homologs of the sequences set forth in FIG. 1. For example, encompassed by the term AN97 gene are degenerate variants of the nucleic acid sequence set forth in FIG. 1. (SEQ ID NO:1). Degenerate variants of a nucleic acid sequence exist because of the degeneracy of the amino acid code; thus, those sequences that vary from the sequence represented by SEQ ID NO:1, but which nonetheless encode an AN97 polypeptide are included within the invention. Likewise, because of the similarity in the structures of amino acids, conservative variations can be made in the amino acid sequence of the AN97 polypeptide while retaining the function of the polypeptide (e.g., as determined in a complementation assay, as described herein and elsewhere). AN97 polypeptides and genes identified in additional Aspergillus strains may be such conservative variations or degenerate variants of the particular AN97 polypeptide and nucleic acid set forth in FIG. 1 (SEQ ID NOs:2 and 29; and 1, respectively). The AN97 polypeptide and gene share at least 80%, e.g., 90%, sequence identity with SEQ ID NOs:2 and 29; and 1, respectively. Regardless of the percent sequence identity between the AN97 sequence and the sequence represented by SEQ ID NOs:1 and 2, the AN97 genes and polypeptides encompassed by the invention are able to complement for the lack of AN97 function (e.g., in a temperature-sensitive mutant) in a standard complementation assay. AN97 genes that are identified and cloned from additional Aspergillus strains, and pathogenic strains in particular, can be used to produce AN97 polypeptides for use in the various methods described herein, e.g., for identifying antifungal agents. Likewise, the term AN80 encompasses homologues and conservative and degenerate variants of the sequences depicted in FIG. 2. Such homologues, conservative variations, and degenerate variants of AN17, AN85, and AN80 also are included within the invention. Excluded from the invention are the naturally-occurring homologs of AN polypeptides and nucleic acids found in *S. cerevisiae* (D9798.4, L8543.16, YGR010W, and L8004.2), although methods employing such polypeptides and nucleic acids are encompassed by the invention.

The AN97, AN17, AN80, and AN85 genes have been identified and shown to be essential for survival, these AN polypeptides and their yeast homologs (e.g., D9798.4, L8543.16, YGR010W, and L8004.2) can be used to identify antifungal agents. More specifically, these AN polypeptides and their yeast homologs can be used, separately or together, in assays to identify test compounds which bind these polypeptides. Such test compounds are expected to be antifungal agents, in contrast to compounds that do not bind AN97, AN17, AN80, AN85, D9798.4, L8543.16, YGR010W, and/or L8004.2. As described herein, any of a variety of art-known methods can be used to assay for binding of test compounds to the polypeptides. The invention includes, for example, a method for identifying an antifungal or anti-yeast agent where the method entails: (a) contacting an AN polypeptide, or homolog thereof, with a test compound; (b) detecting binding of the test compound to the AN polypeptide or homolog; and (c) determining whether a test compound that binds the AN polypeptide or homolog inhibits growth of fungi or yeast, relative to growth of fungi or yeast cultured in the absence of the test compound that binds the AN polypeptide or homolog, as an indication that the test compound is an antifungal or anti-yeast agent.

In various embodiments, the AN polypeptide is derived from a non-pathogenic or pathogenic Aspergillus strain, such as *Aspergillus nidulans, Aspergillus fumigatus, Aspergillus flavus*, and *Aspergillus niger*. Preferably, homologs thereof are derived from the yeast *Saccharomyces cerevisiae*. The test compound can be immobilized on a substrate, and binding of the test compound to the AN polypeptide or homolog can be detected as immobilization of the AN polypeptide or homolog on the immobilized test compound, e.g., in an immunoassay with an antibody that specifically binds AN97.

If desired, the test compound can be a test polypeptide (e.g., a polypeptide having a random or predetermined amino acid sequence; or a naturally-occurring or synthetic polypeptide). Alternatively, the test compound can be a nucleic acid, such as a DNA or RNA molecule. In addition, small organic molecules can be tested. The test compound can be a naturally-occurring compound or it can be synthetically produced, if desired. Synthetic libraries, chemical libraries, and the like can be screened to identify compounds that bind the AN polypeptides. More generally, binding of test compound to the AN polypeptide or homolog can be detected either in vitro or in vivo. Regardless of the source of the test compound, the AN polypeptides described herein can be used to identify compounds that are fungicidal or fungistatic to a variety of pathogenic or non-pathogenic strains.

In an exemplary method, binding of a test compound to an AN polypeptide can be detected in a conventional two-hybrid system for detecting protein/protein interactions (e.g., in yeast or mammalian cells). Generally, in such a method, (a) the AN polypeptide is provided as a fusion protein that includes the AN polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the AN polypeptide polypeptide is detected as reconstitution of a transcription factor. The yeast homologs can be used in similar methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an AN polypeptides is used to identify a compound that decreases the expression of the AN polypeptide in vivo. Such compounds can be used as antifungal agents. To discover such compounds, cells that express an AN polypeptide are cultured, exposed to a test compound (or a mixture of test compounds), and the level of expression or activity is compared with the level of AN polypeptide expression or activity in cells that are otherwise identical but that have not been exposed to the test compound(s). Many standard quantitative assays of gene expression can be utilized in this aspect of the invention.

In order to identify compounds that modulate expression of an AN polypeptide (or homologous sequence), the test compound(s) can be added at varying concentrations to the culture medium of cells that express an AN polypeptide (or homolog), as described above. Such test compounds can include small molecules (typically, non-protein, non-polysaccharide chemical entities), polypeptides, and nucleic acids. The expression of the AN polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the AN polypeptide. Because the AN polypeptides are essential for survival, test compounds that inhibit the expression and/or function of the AN polypeptide will inhibit growth of the cells or kill the cells.

Compounds that modulate the expression of the polypeptides of the invention can be identified by carrying out the assay described above and then measuring the levels of the AN polypeptides expressed in the cells, e.g., by performing a Western blot analysis using antibodies that bind an AN polypeptide.

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of anti-fungal therapeutic agents. These antifungal agents reduce the action of the gene product in a wild type strain, and therefore are useful in treating a subject with that type, or a similarly susceptible type of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic fungus of the same genus or similar species), and the absence or divergence of the sequence in host cells can be determined, if desired. Therapeutic agents directed toward genes or gene products that are not present in the host have several advantages, including fewer side effects, and lower overall dosage.

The invention includes pharmaceutical formulations that include a pharmaceutically acceptable excipient and an antifungal agent identified using the methods described herein. In particular, the invention includes pharmaceutical formulations that contain antifungal agents that inhibit the growth of, or kill, pathogenic Aspergillus strains. Such pharmaceutical formulations can be used for treating an Aspergillus infection in an organism. Such a method entails administering to the organism a therapeutically effective amount of the pharmaceutical formulation. In particular, such pharmaceutical formulations can be used to treat aspergillosis in mammals such as humans and domesticated mammals (e.g., cows and pigs). The efficacy of such antifungal agents in humans can be estimated in an animal model system well known to those of skill in the art (e.g., bovine and rodent (e.g., mouse) model systems). These formulations also can be used to treat fungal infections in plants, e.g., by topically applying the antifungal agent to the plant. Alternatively, where the antifungal agent is a polypeptide or an antisense RNA, a gene encoding the polypeptide or expressing the antisense RNA can be transfected into the plant, using conventional techniques, and the polypeptide or antisense RNA can be expressed in the plant.

Also included within the invention are polyclonal and monoclonal antibodies that specifically bind AN97, AN17, AN80, or AN85 polypeptide. Such antibodies can facilitate detection of AN polypeptides in various Aspergillus strains. These antibodies also are useful for detecting binding of a test compound to AN97, AN17, AN80, or AN85 polypeptides (e.g., using the assays described herein). In addition, monoclonal antibodies that bind AN97, AN17, AN80, or AN85 polypeptide are themselves adequate antifungal agents when administered to a mammal, as such monoclonal antibodies are expected to impede one or more functions of AN97, AN17, AN80, or AN85 polypeptide.

As used herein, "nucleic acids" encompass both RNA and DNA, including cDNA, genomic DNA, and synthetic (e.g., chemically synthesized) DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered basepairing abilities or increased resistance to nucleases.

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

A nucleic acid sequence that is "substantially identical" to an AN97, AN17, AN80, or AN85 nucleotide sequence is at least 80% or 85% identical to the nucleotide sequence of the Aspergillus AN97, AN80, AN85, and AN17 nucleic acids of SEQ ID NO:1, NO:4, NO:7, and NO:10, respectively, as depicted in FIGS. 1, 2, 3, and 4, respectively. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

The AN polypeptides of the invention include, but are not limited to, recombinant polypeptides and natural polypeptides. The invention also encompasses nucleic acid sequences that encode forms of AN97, AN17, AN80, or AN85 polypeptides in which naturally occurring amino acid sequences are altered or deleted. Preferred nucleic acids encode polypeptides that are soluble under normal physiological conditions. Also within the invention are nucleic acids encoding fusion proteins in which a portion of AN97, AN17, AN80, or AN85 is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes isolated, for example, polypeptides (and the nucleic acids that encode these polypeptides) that include a first portion and a second portion; the first portion includes, e.g., an AN polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode AN97, AN17, AN80, or AN85 fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequence of SEQ ID NO:1, NO:4, NO:7, or NO:10, or their complements. The hybridizing portion of the hybridizing nucleic acids is typically at least 15 (e.g., 20, 30, or 50) nucleotides in length. The hybridizing portion of the hybridizing nucleic acid is at least 80%, e.g., at least 95%, or at least 98%, identical to the sequence of a portion or all of a nucleic acid encoding an AN97, AN17, AN80, or AN85 polypeptide. Hybridizing nucleic acids of the type described herein can be used as a cloning probe, a primer (e.g., a PCR primer), or a diagnostic probe. Nucleic acids that hybridize to the nucleotide sequences of SEQ ID NO:1, NO:4, NO:7, or NO:10 are considered "antisense oligonucleotides." Also included within the invention are ribozymes that inhibit the function of AN97, AN17, AN80, or AN85, as determined, for example, in a complementation assay.

In another embodiment, the invention features cells, e.g., transformed host cells, that contain a nucleic acid is encompassed by the invention. A "transformed cell" is a cell into which (or into an ancestor of which) has been introduced, by means of recombinant DNA techniques, a nucleic acid encoding an AN polypeptide. Both prokaryotic and eukaryotic cells are included, e.g., bacteria, Aspergillus, yeast, and the like.

The invention also features genetic constructs (e.g., vectors and plasmids) that include a nucleic acid of the invention which is operably linked to a transcription and/or translation sequence to enable expression, e.g., expression vectors. By "operably linked" is meant that a selected nucleic acid, e.g., a DNA molecule encoding an AN polypeptide, is positioned adjacent to one or more sequence elements, e.g., a promoter, which directs transcription and/or translation of the sequence such that the sequence elements can control transcription and/or translation of the selected nucleic acid.

The invention also features purified or isolated AN97, AN17, AN80, and AN85 polypeptides. As used herein, both "protein" and "polypeptide" mean any chain of amino acids, regardless of length or post-translational modification (e.g., glycosylation or phosphorylation). Thus, the terms "AN97 polypeptide" (or AN97), "AN17 polypeptide" (or AN17), "AN80 polypeptide" (or AN80), or "AN85 polypeptide" (or AN85) include full-length, naturally occurring AN97, AN17, AN80, or AN85 proteins, respectively, as well as recombinantly or synthetically produced polypeptides that correspond to a full-length, naturally occurring AN97, AN17, AN80, or AN85 protein, or to a portion of a naturally occurring or synthetic AN97, AN17, AN80, or AN85 polypeptide.

A "purified" or "isolated" compound is a composition that is at least 60% by weight the compound of interest, e.g., an AN97 polypeptide or antibody. Preferably the preparation is at least 75% (e.g., at least 90% or 99%) by weight the compound of interest. Purity can be measured by any appropriate standard method, e.g., column chromatography, polyacrylamide gel electrophoresis, or HPLC analysis.

Preferred AN97, AN17, AN80, AN85 polypeptides include a sequence substantially identical to all or a portion of a naturally occurring AN97, AN17, AN80, or AN85 polypeptide, e.g., including all or a portion of the sequences shown in FIGS. 1, 2, 3, and 4, respectively. Polypeptides "substantially identical" to the AN polypeptide sequences described herein have an amino acid sequence that is at least 80% or 85% (e.g., 90%, 95% or 99%) identical to the amino acid sequence of the AN97, AN80, AN85 or AN17 polypeptides of SEQ ID NOs:2 and 29; NO:5; NOs:8, 30, 31, and 32; and NOs:11, 33, 34, and 35, respectively. For purposes of comparison, the length of the reference AN polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to an AN polypeptide. By "specifically binds" is meant that an antibody recognizes and binds a particular antigen, e.g., an AN97, AN17 polypeptide, but does not substantially recognize and bind other molecules in a sample, e.g., a biological sample that naturally includes AN97, AN17, AN80, or AN85. In one embodiment the antibody is a monoclonal antibody.

In another aspect, the invention features a method for detecting an AN polypeptide in a sample. This method includes: obtaining a sample suspected of containing AN97, AN17, AN85, or AN80; contacting the sample with an antibody that specifically binds an AN97, AN17, AN85 or AN80 polypeptide under conditions that allow the formation of complexes of an antibody and AN97, AN17, AN85 or AN80; and detecting the complexes, if any, as an indication of the presence of AN97, AN17, AN85 or AN80 in the sample.

Also encompassed by the invention is a method of obtaining a gene related to (i.e., a functional homologue of) the AN97, AN17, AN85, or AN80 gene. Such a method entails obtaining a labeled probe that includes an isolated nucleic acid which encodes all or a portion of AN97, AN17, AN85, or AN80, or a homolog thereof (e.g., D9798.4, L8543.16, YGR010W, or L8004.2); screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the AN97, AN17, AN85, or AN80 gene.

The invention offers several advantages. By combining gene knockout assays, as described herein, with assays of conditional sensitivity, we have identified genes that are truly essential, i.e., genes whose absence is fungicidal to Aspergillus. In addition, the methods for identifying antifungal agents can be configured for high throughput screening of numerous candidate antifungal agents.

Other features and advantages of the invention will be apparent from the following detailed description, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

BRIEF DESCRIPTION OF THE DRAWINGS

FIGS. 1A to 1K are a representation of the amino acid and nucleic acid sequences of the AN97 polypeptide and gene from an *Aspergillus nidulans* strain (SEQ ID NOs:2 and 29 and NO:1, respectively). The non-coding sequence is set forth as SEQ ID NO:3.

FIGS. 2A to 2D are a representation of the amino acid and nucleic acid sequences of the AN80 polypeptide and gene from an *Aspergillus nidulans* strain (SEQ ID NOs:5 and 4, respectively). The non-coding sequence is set forth as SEQ ID NO:6.

FIGS. 3A to 3D are a representation of the amino acid and nucleic acid sequences of the AN85 polypeptide and gene from an *Aspergillus nidulans* strain (SEQ ID NOs: 8, 30, 31 and 32; and NO:7, respectively). The non-coding sequence is set forth as SEQ ID NO:9.

FIGS. 4A to 4D are a representation of the amino acid and nucleic acid sequences of the AN17 polypeptide and gene from an *Aspergillus nidulans* strain (SEQ ID NOs:11, 33, 34, and 35; and NO:10, respectively). The non-coding sequence is set forth as SEQ ID NO:12.

FIGS. 5A to 5H are a representation of the amino acid and nucleic acid sequences of the D9798.4 polypeptide and gene from *S. cerevisiae* (SEQ ID NOs:14 and 13, respectively). The non-coding sequence is set forth as SEQ ID NO:15.

FIGS. 6A to 6D are a representation of the amino acid and nucleic acid sequences of the YGR010W polypeptide and gene from *S. cerevisiae* (SEQ ID NOs:17 and 16, respectively). The non-coding sequence is set forth as SEQ ID NO:18.

FIGS. 7A to 7G are a representation of the amino acid and nucleic acid sequences of the L8543.16 polypeptide and gene from *S. cerevisiae* (SEQ ID NOs:20 and 19, respectively). The non-coding sequence is set forth as SEQ ID NO:21.

FIGS. 8A to 8D are a representation of the amino acid and nucleic acid sequences of the L8004.2 polypeptide and gene from *S. cerevisiae* (SEQ ID NOs:23 and 22, respectively). The non-coding sequence is set forth as SEQ ID NO:24.

DETAILED DESCRIPTION OF THE INVENTION

Identifying Essential Aspergillus Genes

As shown by the experiments described below, expression of each of the AN97, AN17, AN80, and AN85 polypeptides is essential for survival of *Aspergillus nidulans*. *Aspergillus nidulans* is available from the ATCC (#FGSC4). To identify genes for which inhibition of gene expression is fungicidal, various mutants of *Aspergillus nidulans* were assayed for conditional sensitivity. In general, mutagenesis of *Aspergillus nidulans* can be accomplished using any of various art-known methods. For example, exposure to ultraviolet light, x-rays, and/or chemical mutagens is acceptable. Examples of suitable chemical mutagens include ethylmethansulfonate (EMS), metyhlmethanesulfonate (MMS), methylnitrosoguanidine (NTG), 4-nitroquinoline-1-oxide (NQO), 2-aminopurine, 5-bromouracil, ICR 191 and other acridine derivatives, sodium bisulfite, ethidium bromide, nitrous acid, hydroxylamine, N-methyl-N'-nitroso-N-nitroguanidine, and alkylating agents (for further description of art-known mutagens and mutagenesis methods, see, e.g., Current Protocols in Molecular Biology, 1995 and Adelberg et al., *Biochem. Biophys. Res. Comm.* 18:788, 1965).

To identify conditional-sensitive mutants, mutagenized cells can be grown under (a) a first set of permissive conditions, then shifted to (b) restrictive conditions, and then to (c) a second set of permissive conditions. The cells of interest are those mutants that grow under the permissive conditions of (a), but fail to grow under the restrictive conditions of (b), and fail to recover under the permissive conditions of (c).

Ostensibly, any change in a growth parameter can serve as the "restrictive condition." For example, the restrictive conditions may be met by increasing or decreasing the temperature at which the cells are grown, thereby allowing the identification of temperature-sensitive mutants. For example, the optimal growth temperature for *A. nidulans* is 28° C., and a typical restrictive temperature is 42° C. In alternative methods, the change to a restrictive condition may entail changing one or more of the following parameters of the growth conditions: pH, type and/or concentration of carbon and nitrogen sources, trace minerals, vitamins, salts, conidia-forming materials (e.g., DMSO, glycerol, and deuterated water), humidity, and the like. In general, permissive growth conditions allow the strains to grow at a rate that is at least 75% of that of the wild-type growth rate of Aspergillus. The second set of permissive conditions (in (c)) can be the same as, or different from, the first permissive conditions. Typically, the cells are subjected to the second permissive conditions for at least 2 growth cycles (more typically, at least 5, 10, 15 or even 20 growth cycles). Generally, the cells are subjected to the restrictive conditions for 2 to 20 growth cycles (typically 2–10 growth cycles) and for 24 hours or less.

In practicing the invention, cell death (e.g., in (b)) can be detected using any of a number of conventional criteria. For example, cell death can be detected macroscopically by observing that a colony of cells has approximately the same size, or a reduced size, after a length of time that is normally sufficient for several growth cycles under the second permissive conditions. Detection of cell death also can be facilitated by the use of light microscopy and cell staining to reveal cytological deformations and/or morphologies commonly known to be indicative of cell death. The absence of DNA, RNA, or protein synthesis also can signify cell death.

Identification of Homologs of AN Polypeptides

Having shown that the AN97, and AN80, and AN85 genes and polypeptides are essential for survival in Aspergillus, it can be expected that homologs of these polypeptides, when present in other organisms, for example pathogenic yeast, are essential for survival of those organisms as well. Using the sequences of the AN polypeptides identified in Aspergillus, homologs of these polypeptides were identified in the yeast *S. cerevisiae*. The coding sequences of AN97, AN80, and AN85 were used to search the GenBank database of nucleotide sequences to identify homologs of AN97, AN80, and AN85, respectively, which are essential genes in other organisms. Sequence comparisons were performed using the Basic Local Alignment Search Tool (BLAST) (Altschul et al., *J. Mol. Biol.*, 215:403–410 1990). The percent sequence identity shared by the AN polypeptides and their homologs were determined using the GAP program from the Genetics Computer Group (GCG) Wisconsin Sequence Analysis Package (Wisconsin Package Version 9.0, GCG; Madison, Wis.). The following parameters were used: gap creation penalty, 12 (protein) 50 (DNA); gap extension penalty, 4 (protein) 3 (DNA). The percent sequence identity shared by the AN polypeptides and their homologs are summarized in Table 1. Typically, the AN polypeptides and their homologs share at least 25% (e.g., at least 40%) sequence identity. Typically, the DNA sequences encoding AN polypeptides and their homologs share at least 35% (e.g., at least 45%) sequence identity.

TABLE 1

Sequence Identity Shared by AN Polypeptides and Their Homologues.

| AN Polypeptide | Homolog in Saccharomyces | % Identity of DNA Sequences (coding region) | % Identity of Polypeptide Sequences |
|---|---|---|---|
| AN80 | L8004.2 | 37.4 | 27.9 |
| AN85 | YGR010W | 50.2 | 41.0 |
| AN85 | L8543.16 | 49.2 | 43.7 |
| AN97 | D9798.4 | 38.7 | 25.8 |

To confirm that these yeast homologs of the AN polypeptides are essential for survival of yeast, the gene encoding each of the homologs was, separately, deleted from the *S. cerevisiae* genome. To this end, standard methods for making yeast "knock outs" were used, as described by Baudin et al., *Nucl. Acids. Res.* 21:3329–3330, 1993. Briefly, a portion of the yeast genome was amplified in a polymerase chain reaction (PCR) that employed two primers. The primers for L8004.2 were 5' AGGAAAGTAGCTATCGTAACGGG-TACTAATAGTAATCTTGGTCTCTT GGCCTC-CTCTAG3' (SEQ ID NO:25) and 5' TACGCA- GAGATATATTAAATGGGGTTCT AGTTTCAACAATTTCGTTCAGAATGACACG3' (SEQ ID NO:26). The primers for D9798.4 were 5' TTAACAGC-CGCGCCCATCATGCAAGATCCTGATGG-TATTGACATTCTC TTGG CCTCCTCTAG3' (SEQ ID NO:18) and 5' GCATATCAATTTTAACAGACCTCGCT-GAAAG ACTCTGAATCCTCGTTCAGAATGACACG3' (SEQ ID NO:28). These primers hybridized to a portion of the 5' and 3' sequences flanking the open reading frames of the yeast homologs and include nucleotides that are homologous to the HIS3 selectable marker. Following PCR amplification, the resulting crude mix was directly used to transform yeast, following a standard protocol.

Identification of AN97, AN17, AN80, and AN85 Genes in Additional Aspergillus Strains Now that the AN97, AN80, AN17, and AN85 genes and their yeast homologs, L8004.2, YGR010W, L8543.16, and D9798.4, have been identified as essential for survival (as described below under "Examples"), these genes, or fragments thereof, can be used to detect homologous essential genes in other organisms. In particular, these genes can be used to analyze various pathogenic and non-pathogenic strains of Aspergillus (e.g., *Aspergillus fumigatus*, *Aspergillus flavus* and *Aspergillus niger*) and yeast (e.g., *Candida albicans*). In particular, fragments of a nucleic acid (DNA or RNA) encoding an AN polypeptide or yeast homolog (or sequences complementary thereto) can be used as probes in conventional nucleic acid hybridization assays of pathogenic organisms (e.g., pathogenic Aspergillus strains). For example, nucleic acid probes (which typically are 8–30, or usually 15–20, nucleotides in length) can be used to detect the AN97, AN17, AN80, AN85 genes or homologs thereof in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library or a cDNA library constructed from mRNA obtained from an Aspergillus or yeast strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the cDNA library, or other nucleic acid sample, typically is performed under moderate to high stringency conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

As used herein, high stringency conditions include, for example, hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, cDNA libraries constructed from pathogenic or non-pathogenic Aspergillus or yeast strains can be screened. For example, such strains can be screened for AN97, AN17, AN85, or AN80 expression by Northern blot analysis. Upon detection of AN97, AN17, AN85, or AN80 transcripts or transcripts of homologs thereof, cDNA libraries can be constructed from RNA isolated from the appropriate strain, utilizing standard techniques well known to those of skill in the art. Alternatively, a total genomic DNA library can be screened using an AN97, AN17, AN85, or AN80 probe (or a probe directed to a homolog thereof).

New gene sequences can be isolated, for example, by performing PCR using two degenerate oligonucleotide primer pools designed on the basis of nucleotide sequences within the AN97, AN17, AN85 or AN80 genes, or their homologs, as depicted herein. The template for the reaction can be cDNA obtained by reverse transcription of mRNA prepared from strains known or suspected to express an AN97, AN17, AN85, or AN80 allele or an allele of a homolog thereof. The PCR product can be subcloned and sequenced to ensure that the amplified sequences represent the sequences of a new AN97, AN17, AN85, or AN80 nucleic acid sequence, or a sequence of a homolog thereof.

The PCR fragment can then be used to isolate a full length cDNA clone by a variety of known methods. For example, the amplified fragment can be labeled and used to screen a bacteriophage cDNA library. Alternatively, the labeled fragment can be used to screen a genomic library.

PCR technology also can be used to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Now that the AN97, AN17, AN85, and AN80 genes and their homologs have been cloned, synthesis of the AN polypeptides or their homologs (or an antigenic fragment thereof) for use as antigens, or for other purposes, can readily be accomplished using any of the various art-known techniques. For example, an AN polypeptide or homolog, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or insect cells (e.g., by using a baculovirus-based expression vector).

Proteins and polypeptides can also be produced in plant cells, if desired. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors*: A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, AN polypeptides or their homologs can be produced as fusion proteins. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary insect cell expression system, a baculovirus such as *Autographa californica* nuclear polyhedrosis virus (AcNPV), which grows in *Spodoptera frugiperda* cells, can be used as a vector to express foreign genes. A coding sequence encoding an AN polypeptide or homolog can be cloned into a non-essential region (for example the polyhedrin gene) of the viral genome and placed under control of a promoter, e.g., the polyhedrin promoter or an exogenous promoter. Successful insertion of a gene encoding an AN polypeptide or homolog can result in inactivation of the polyhedrin gene and production of non-occluded recombinant virus (i.e., virus lacking the proteinaceous coat encoded by the polyhedrin gene). These recombinant viruses are then used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051).

In mammalian host cells, a number of viral-based expression systems can be utilized. When an adenovirus is used as an expression vector, the nucleic acid sequence encoding the AN polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an AN97, AN17, AN85, or AN80 gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In cases where an entire native gene (e.g., AN97) or cDNA, including its own initiation codon and adjacent sequences, is inserted into the appropriate expression vector, no additional translational control signals may be needed. In other cases, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., Methods in Enzymol., 153:516, 1987).

The AN polypeptides and homologs can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the AN polypeptide or homolog thereof can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, cDNA encoding the protein is cloned into an expression vector that includes the dihydrofolate reductase (DHFR) gene. Integration of the plasmid and, therefore, the AN polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include PCVSEII-DHFR and pAdD26SV(A) (described in Ausubel et al., supra).

A number of other selection systems can be used, including but not limited to the herpes simplex virus thymidine kinase, hypoxanthine-guanine phosphoribosyl-transferase, and adenine phosphoribosyl-transferase genes can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, an AN polypeptide or homolog, or a portion thereof, can be fused to an immunoglobulin Fc domain. Such a fusion protein can be readily purified using a protein A column, for example. Moreover, such fusion proteins permit the production of a chimeric form of an AN polypeptide or homolog having increased stability in vivo.

Once the recombinant AN polypeptide (or homolog) is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-AN97 antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an AN polypeptide (e.g., an AN97-maltose binding fusion protein, an AN97-β-galactosidase fusion protein, or an AN97-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of AN97, AN17, AN85, AN80 from pathogenic Aspergillus strains, and fragments of D9798.4, L8004.2, L8543.16, and YGR010W from yeast, can be produced by standard chemical synthesis (e.g., by the methods described in *Solid Phase Peptide Synthesis*, 2nd ed., The Pierce Chemical Co., Rockford, Ill., 1984) and used as antigens, for example.

Antibodies

AN97, AN17, AN85, or AN80 polypeptides (or antigenic fragments or analogs of such polypeptide) can be used to raise antibodies useful in the invention, and such polypeptides can be produced by recombinant or peptide synthetic techniques (see, e.g., *Solid Phase Peptide Synthesis*, supra; Ausubel et al., supra). Likewise, antibodies can be raised against the yeast homologs. In general, the polypeptides can be coupled to a carrier protein, such as KLH, as described in Ausubel et al., supra, mixed with an adjuvant, and injected into a host mammal. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies (mAbs), which are homogeneous populations of antibodies to a particular antigen, can be prepared using the AN polypeptides or homologs thereof and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In Monoclonal Antibodies and T Cell Hybridomas, Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., Monoclonal Antibodies and Cancer Therapy, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of an AN polypeptide or homolog thereof in an immunoassay, such as a Western blot or immunoprecipitation analysis using standard techniques, e.g., as described in Ausubel et al., supra. Antibodies that specifically bind to AN97, AN17, AN85, or AN80, or conservative variants and homologs thereof, are useful in the invention. For example, such antibodies can be used in an immunoassay to detect AN97 in pathogenic or non-pathogenic strains of Aspergillus (e.g., in Aspergillus extracts).

Preferably, antibodies of the invention are produced using fragments of the AN polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant AN polypeptide or homolog, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against an AN polypeptide or homolog. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind AN polypeptides or homologs can be used, for example, to detect expression of an AN97, AN17, AN85, AN80 gene or homolog in another strain of Aspergillus. For example, AN97 polypeptide can be readily detected in conventional immunoassays of Aspergillus cells or extracts. Examples of suitable assays include, without limitation, Western blotting, ELISAs, radioimmune assays, and the like.

Assay for Antifungal Agents

The invention provides a method for identifying an antifungal agent(s). Although the inventors are not bound by any particular theory as to the biological mechanism involved, the new antifungal agents are thought to inhibit specifically the function of the AN polypeptides or expression of the AN97, AN17, AN85, or AN80 genes, or homologs thereof. Screening for antifungal agents can be rapidly accomplished by identifying those compounds (e.g., polypeptides, ribonucleic acids (including ribozymes), nucleic acids (including antisense nucleic acids), or small molecules) that specifically bind to an AN polypeptide. A homolog of an AN polypeptide (e.g., D9798.4, L8004.2, L8543.16, or YGR010W) can be substituted for the AN polypeptide in the methods summarized herein. Specific binding of a test compound to an AN polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with an AN polypeptide (or a combination of AN polypeptides and/or homologs) by adding the polypeptide(s) in a solution (typically, at a concentration of 0.05 to 1 mg/ml in a volume of 1–100 $\mu$l) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the AN polypeptide or homolog is contained in water or a buffer. The plate is then washed with a buffer that lacks the bound polypeptide. To block the free protein-binding sites on the plates, the plates are blocked with a protein that is unrelated to the bound polypeptide. For example, 300 $\mu$l of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the new AN polypeptides (or homologs thereof) can be detected by any of a variety of art-known methods. For example, an antibody that specifically binds an AN polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-AN97 antibody). In an alternative detection method, the AN polypeptide is labeled, and the label is detected (e.g., by labeling an AN polypeptide with a radioisotope, fluorophore, chromophore, or the like). In still another method, the AN polypeptide is produced as a fusion protein with a protein that can be detected optically, e.g., green fluorescent protein (which can be detected under UV light). In an alternative method, the AN polypeptide can be produced as a fusion protein with an enzyme having a detectable enzymatic activity, such as horse radish peroxidase, alkaline phosphatase, $\alpha$-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and $\alpha$-galactosidase) and non-enzymatic polypeptides (e.g., serum proteins, such as BSA and globulins, and milk proteins, such as caseins).

In various in vivo methods for identifying polypeptides that bind AN polypeptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Kits for practicing various two-hybrid methods are commercially available (e.g., from Clontech; Palo Alto, Calif.).

Generally, the two-hybrid methods involve in vivo reconstitution of two separable domains of a transcription factor. The DNA binding domain (DB) of the transcription factor is required for recognition of a chosen promoter. The activation domain (AD) is required for contacting other components of the host cell's transcriptional machinery. The transcription factor is reconstituted through the use of hybrid proteins. One hybrid is composed of the AD and a first protein of interest. The second hybrid is composed of the DB and a second protein of interest. In cases where the first and second proteins of interest interact with each other, the AD and DB are brought into close physical proximity, thereby reconstituting the transcription factor. Association of the proteins can be measured by assaying the ability of the reconstituted transcription factor to activate transcription of a reporter gene.

Useful reporter genes are those that are operably linked to a promoter which is specifically recognized by the DB. Typically, the two-hybrid system employs the yeast *Saccharomyces cerevisiae* and reporter genes, the expression of which can be selected under appropriate conditions. Other eukaryotic cells, including mammalian and insect cells, can be used, if desired. The two-hybrid system provides a convenient method for cloning a gene encoding a polypeptide (i.e., a candidate antifungal agent) that binds a second, preselected polypeptide (e.g., AN97). Typically, though not necessarily, a cDNA library is constructed such that randomly generated sequences are fused to the AD, and the protein of interest (e.g., AN97 or AN80) is fused to the DB.

In such two-hybrid methods, two fusion proteins are produced. One fusion protein contains the AN polypeptide (or homolog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the AN polypeptide to the test polypeptide (i.e., candidate antifungal agent) reconstitutes the transcription factor. Reconstitution of the transcription factor can be detected by detecting expression of a gene (i.e., a reporter gene) that is operably linked to a DNA sequence that is bound by the DNA binding domain of the transcription factor.

The methods described above can be used for high throughput screening of numerous test compounds to identify candidate antifungal (or anti-yeast) agents. Having identified a test compound as a candidate antifungal agent, the candidate antifungal agent can be further tested for inhibition of fungal growth in vitro or in vivo (e.g., using an animal, e.g., rodent, model system) if desired. Using other, art-known variations of such methods, one can test the ability of a nucleic acid (e.g., DNA or RNA) used as the test compound to bind an AN polypeptide or homolog thereof.

In vitro, further testing can be accomplished by means known to those in the art such as an enzyme inhibition assay or a whole-cell fungal growth inhibition assay. For example, an agar dilution assay identifies a substance that inhibits fungal growth. Microtiter plates are prepared with serial dilutions of the test compound; adding to the preparation a given amount of growth substrate; and providing a preparation of Aspergillus spores. Inhibition of growth is determined, for example, by observing changes in optical densities of the fungal cultures.

Inhibition of fungal growth is demonstrated, for example, by comparing (in the presence and absence of a test compound) the rate of growth or the absolute growth of fungal sporulation or nuclei. Inhibition includes a reduction of one of the above measurements by at least 20% (e.g., at least 25%, 30%, 40%, 50%, 75%, 80%, or 90%).

Rodent (e.g., murine) and bovine animal models of aspergillosis are known to those of skill in the art, and such animal model systems are accepted for screening antifungal agents as an indication of their therapeutic efficacy in human patients (Rhodes et al., *J. Med. and Vet. Myco.*, 30:51–57, 1992). Indeed, the clinical manifestations of bovine aspergillosis show many pathological similarities to aspergillosis in humans and rodents. In a typical in vivo assay, an animal is infected with a pathogenic Aspergillus strain, e.g., by inhalation of Aspergillus spores (i.e., *conidia*), and conventional methods and criteria are used to diagnose the mammal as being afflicted with aspergillosis. The candidate antifungal agent then is administered to the mammal at a dosage of 1–100 mg/kg of body weight, and the mammal is monitored for signs of amelioration of disease. Alternatively, the test compound can be administered to the mammal prior to infecting the mammal with Aspergillus, and the ability of the treated mammal to resist infection is measured. Of course, the results obtained in the presence of the test compound are compared with results in control animals, which are not treated with the test compound. Administration of candidate antifungal agent to the mammal can be carried out as described below, for example.

Antisense Methods

Antisense approaches involve the design of oligonucleotides (either DNA or RNA) that are complementary to AN97, AN17, AN80, or AN85 mRNA. The antisense oligonucleotides bind to the AN97, AN17, AN80, or AN85 coding sequences and/or mRNA transcripts and inhibit transcription and/or translation. Absolute complementarity is not required. A sequence "complementary" to a portion of an RNA, as referred to herein, means a sequence having sufficient complementarity to be able to hybridize with the RNA and form a stable duplex; in the case of double-stranded antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (Wagner, *Nature*, 372:333, 1984). Thus, oligonucleotides complementary to either the 5'-or 3'- non-translated, non-coding regions of the AN97, AN17, AN80, or AN85 genes, or their yeast homologs D9798.4, L8543.16, YGR010W, of L8004.2, as represented by SEQ ID NOs:1, 4, 7, 10, 13, 16, 19, and 22 can be used in an antisense approach to inhibit translation of the endogenous sequences. Oligonucleotides complementary to the 5' untranslated region of the mRNA typically also include the complement of the AUG start codon.

Antisense oligonucleotides complementary to mRNA coding regions are less preferred inhibitors of translation, but can be used in accordance with the invention. Whether designed to hybridize to the 5'-, 3'-, or coding region of the mRNA, antisense nucleic acids should be at least six nucleotides in length (e.g., oligonucleotides ranging from 6 to about 50 nucleotides in length). In specific aspects, the oligonucleotide is at least 10 nucleotides, at least 15 nucleotides, or at least 25 nucleotides.

Regardless of the choice of target sequence, in vitro studies typically are first performed to quantitate the ability of the antisense oligonucleotide to inhibit gene expression. Typically, these studies utilize controls that distinguish between antisense gene inhibition and nonspecific biological effects of oligonucleotides. Generally, these studies compare levels of the target RNA or protein with that of an internal control RNA or protein. Additionally, it is envisioned that results obtained using the antisense oligonucleotide are compared with those obtained using a control oligonucleotide. Typically, the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA, or chimeric mixtures, or derivatives or modified versions thereof, and can be single-stranded or double-stranded. The oligonucleotides can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA*, 86:6553, 1989; Lemaitre et al., *Proc. Natl. Acad. Sci. USA*, 84:648, 1987; PCT Publication No. WO 88/09810) or the blood-brain barrier (see, e.g., PCT Publication No. WO 89/10134), or hybridization-triggered cleavage agents (see, e.g., Krol et al., *BioTechniques*, 6:958, 1988), or intercalating agents (see, e.g., Zon, *Pharm. Res.*, 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropyl) uracil, (acp3) w, and 2,6-diaminopurine.

The antisense oligonucleotide can also include at least one modified sugar moiety selected from the group including, but not limited to, arabinose, 2-fluoroarabinose, xylulose, and hexose.

In yet another embodiment, the antisense oligonucleotide includes at least one modified phosphate backbone, e.g., a phosphorothioate, a phosphorodithioate, a phosphoramidothioate, a phosphoramidate, a phosphorodiamidate, a methylphosphonate, an alkyl phosphotriester, and a formacetal, or an analog of any of these backbones.

In addition, the antisense oligonucleotide can be an α-anomeric oligonucleotide that forms specific double-stranded hybrids with complementary RNA in which, contrary to the usual β-units, the strands run parallel to each other (Gautier et al., *Nucl. Acids. Res.*, 15:6625, 1987). The oligonucleotide can be a 2'-0-methylribonucleotide (Inoue et al., *Nucl. Acids Res.*, 15:6131, 1987), or a chimeric RNA-DNA analog (Inoue et al., *FEBS Lett.*, 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al., *Nucl. Acids Res.*, 16:3209, 1988, and methylphosphonate oligonucleotides can be prepared by use of controlled pore glass polymer supports (Sarin et al., *Proc. Natl. Acad. Sci. USA*, 85:7448, 1988).

While antisense nucleotides complementary to the AN97, AN17, AN80, AN85, D9798.4, L8543.16, YGR010W, or L8004.2 coding region sequence could be used, those complementary to the transcribed untranslated region are preferred. Generally, such antisense oligonucleotides are 10–100 nucleotides in length (e.g., 15–50 nucleotides). Pathogenic microorganisms, such as Aspergillus, can spontaneously phagocytose oligonucleotides. Accordingly, these antisense oligonucleotides can be administered systemically or locally to a patient suffering from a pathogen infection in order to deliver the antisense oligonucleotides to the infectious organism in a method of treatment. For example, such antisense oligonucleotides can be used to inhibit expression of an AN polypeptide and thereby treat or inhibit fungal infections. A suitable approach uses a recombinant DNA construct in which the antisense oligonucleotide is placed under the control of a strong pol III or pol II promoter. The use of such a construct to transfect fungal cells in the patient will result in the transcription of sufficient amounts of single stranded nucleic acids that form complementary base pairs with the endogenous transcripts encoding AN polypeptides and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Appropriate vectors can be constructed by recombinant DNA technology methods standard in the art. Vectors can be plasmid, viral, or others known in the art, used for replication and expression in fungal cells. Expression of the sequence encoding the antisense RNA can be by any promoter known in the art to act in fungi, e.g. Aspergillus, cells. Such promoters can be inducible or constitutive, such as an alcohol dehydrogenase promoter (e.g., alcA) and a nitrate reductase promoter (e.g., niiA). Any type of plasmid, cosmid, or viral vector can be used to prepare the recombinant DNA construct which can be administered systemically or directly to the infected tissue.

Ribozymes

Ribozyme molecules designed to catalytically cleave mRNA transcripts encoding AN polypeptides also can be used to prevent translation of mRNA and expression of the AN polypeptides (see, e.g., PCT Publication WO 90/11364; Saraver et al., *Science*, 247:1222, 1990). Various ribozymes that cleave mRNA at site-specific recognition sequences can be used to destroy mRNAs encoding the AN polypeptides (e.g., the use of hammerhead ribozymes). Hammerhead ribozymes cleave mRNAs at locations dictated by flanking regions that form complementary base pairs with the target mRNA. It is recommended that the target mRNA have the following sequence of two bases: 5'-UG-3'. The construction and production of hammerhead ribozymes is known in the art (Haseloff et al., *Nature*, 334:585, 1988). There are numerous examples of potential hammerhead ribozyme cleavage sites within the nucleotide sequence of cDNAs encoding AN polypeptides (FIGS. 1 to 3). Typically, the ribozyme is engineered so that the cleavage recognition site is located near the 5' end of the mRNA encoding the AN polypeptide in order to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., *Science*, 224:574, 1984; Zaug et al., *Science*, 231:470, 1986; Zug et al., *Nature*, 324:429, 1986; PCT Application No. WO 88/04300; and Been et al., Cell, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in AN polypeptides.

As in the antisense approach, the ribozymes can be composed of modified oligonucleotides (e.g., for improved stability, targeting, etc.), and should be delivered to cells that express the AN polypeptide. A typical method of delivery involves using a DNA construct "encoding" the ribozyme under the control of a strong constitutive promoter, e.g., a pol III or pol II promoter, so that transfected cells will produce sufficient quantities of the ribozyme to destroy endogenous mRNAs encoding AN polypeptides and inhibit translation thereof. Because ribozymes, unlike typical antisense molecules, are catalytic, a lower intracellular concentration is required for efficiency.

Pharmaceutical Formulations

Treatment includes administering a pharmaceutically effective amount of a composition containing an antifungal agent to a subject in need of such treatment, thereby inhibiting fungal growth in the subject. Such a composition typically contains from about 0.1 to 90% by weight (such as 1 to 20% or 1 to 10%) of an antifungal agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antifungal agent in each pharmaceutical formulation varies according to the formulation itself and the therapeutic effect desired in the specific pathologies and correlated therapeutic regimens. Appropriate dosages of the antifungal agents can readily be determined by those of ordinary skill in the art of medicine by monitoring the mammal for signs of disease amelioration or inhibition, and increasing or decreasing the dosage and/or frequency of treatment as desired. The optimal amount of the antifungal compound used for treatment of conditions caused by or contributed to by fungal infection may depend upon the manner of administration, the age and the body weight of the subject and the condition of the subject to be treated. Generally, the antifungal compound is administered at a dosage of 1 to 100 mg/kg of body weight, and typically at a dosage of 1 to 10 mg/kg of body weight.

EXAMPLE

In this example, the identification and cloning of AN97, AN17, AN85, and AN80 are described.

A library of approximately 1,000 *A. nidulans* mutants was obtained, which was prepared using 4-nitroquinoline as a mutagen, as described previously (Harris et al., *Genetics* 136:517–532 1994). To identify strains having a temperature-sensitive mutation in an essential gene, the collection of 1,000 strains was grown at the permissive temperature of 28° C. for 16 hours in minimal medium (MN; pH 6.5, 1% glucose, nitrate salts and trace elements as described in Kafer, *Adv. Genet.* 19:33–131, 1977). The trace element solution was stored at 4° in the dark; each liter contained 40 mg $Na_2B_4O_7$ (10 $H_2O$), 400 mg cupric sulfate (5 $H_2O$), 1 g ferric phosphate (4 $H_2O$), 600 mg manganese sulfate (4 $H_2O$), 800 mg disodium molybdate (2 $H_2O$), and 8 g zinc sulfate (7 $H_2O$). Salt solution was stored at 4° C. after adding 2 ml chloroform as a preservative; each liter contained 26 g potassium chloride, 26 g magnesium sulfate (7 $H_2O$) 76 g monobasic potassium phosphate and 50 mL trace element solution. Supplement solution was sterilized by autoclaving for 15 minutes and stored in a light-proof container due to the reactivity of riboflavin. Each liter contains 100 mg nicotinic acid, 250 mg riboflavin, 200 mg pantothenic acid, 50 mg pyridoxin, 1 mg biotin, and 20 mg p-aminobenzoic acid.

*Condidia* ($2 \times 10^6$/ml in sterile, distilled water) were mutagenized with NQO (4 µg/ml) for 30 minutes at 37° C. with constant shaking. Diluting the conidia with an equal volume of 5% sodium thiosulfate inactivated the NQO.

Mutagenized conidia were diluted and plated onto CM+TRITON X-100 plates (from Union Carbide Chemicals,) and incubated at 28° C. for 3 days. Colonies were replica plated and the replica plated plates were incubated at 28° C. and 42° C. Putative temperature-sensitive mutants were picked and retested, then stored as a colony plug in 15% glycerol at −70° C.

The cells were replica plated and shifted to 42° C. for 24 hours. Strains that grew poorly or not at all were selected, because they were most likely to represent strains having a mutation in an essential gene. After 1 round of subjecting the collection of cells to the temperature shift, approximately 100 strains (10% of the strains) were identified as having failed to recover once they were shifted to the second permissive temperature. These 100 strains were again grown at a first permissive temperature, followed by 24 hours at 42° C., and 24 or 48 hours at 28° C. (the second permissive temperature). After this second round of selection, 10 strains were identified as having failed to recover, and therefore as containing a temperature sensitive mutation in an essential gene.

Complementation analysis was used to identify the essential gene containing the mutation for each strain. Each of the 10 mutant strains was transformed, separately, with an Aspergillus genomic cosmid library containing an ArgB marker in a pCosAx vector (Adams et al., *FEMS Microbiol. Lett.*, 122:227–231 1994). The strains were grown for 3–4 days at 28° C., replica plated, and shifted to 42° C. for a maximum of 3 days. Strains that grew were collected, and the cosmid DNA was packaged by "selfing" the organism to force it to undergo meiosis. In this method, a colony is picked and grown on a separate plate (which typically is sealed to prevent contamination). The resulting spores then are picked and grown in liquid culture, prior to isolating the DNA. The cosmid was packaged using GIGAPACK III Gold packaging system (Stratagene; La Jolla, Calif.), which produced plasmids that were subsequently isolated, purified, and used to transform bacteria for amplification, isolation, purification, and sequencing.

In one of the resulting strains, the mutation was in a gene designated "AN97," indicating that in *A. nidulans* this gene is essential for survival. The amino acid sequence of the AN97 polypeptide and the AN97 gene of *A. nidulans* are provided in FIG. 1 as SEQ ID NOs:2 and 29; and NO:1, respectively.

In a second strain, the mutation was in a gene designated "AN80," indicating that this gene is essential for survival. The AN80 amino acid and nucleic acid sequences are shown in FIG. 2 as SEQ ID NOs:5 and 4, respectively.

In a third strain, the mutation was in a gene designated "AN85," indicating that this gene is essential for survival. The AN85 amino acid and nucleic acid sequences are shown in FIG. 3 as SEQ ID NOs:8, 30, 31, and 32; and NO:7, respectively.

In a fourth strain, the mutation was in a gene designated "AN17," indicating that this gene is essential for survival. The AN17 amino acid and nucleic acid sequences are shown in FIG. 4 as SEQ ID NOs:11, 33, 34, and 35; and NO:10, respectively.

Now that each of these genes is known to be essential for survival of Aspergillus; the AN polypeptides (AN97, AN17, AN80, and AN85) can be used to identify antifungal agents by using the assays described herein. Other art-known assays to detect interactions of test compounds with proteins, or to detect inhibition of fungal growth also can be used with the AN97, AN17, AN80, and AN85 genes and gene products and homologs thereof.

OTHER EMBODIMENTS

The invention also features fragments, variants, analogs, and derivatives of the AN polypeptides described above that retain one or more of the biological activities of the AN polypeptides, e.g., as determined in a complementation assay. Also included within the invention are naturally-occurring and non-naturally-occurring allelic variants. Compared with the naturally-occurring AN97, AN80, AN85, and AN17 nucleotide sequences depicted in FIGS. 1, 2, 3, and 4 respectively, the nucleic acid sequence encoding allelic variants may have a substitution, deletion, or addition of one or more nucleotides. The preferred allelic variants are functionally equivalent to an AN polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 35

<210> SEQ ID NO 1
<211> LENGTH: 5596
<212> TYPE: DNA
<213> ORGANISM: Aspergillus nidulans
<220> FEATURE:
<221> NAME/KEY: CDS
<222> LOCATION: (604)...(2655)
<221> NAME/KEY: CDS
<222> LOCATION: (2706)...(3992)

<400> SEQUENCE: 1
agcgctgcgc agggcagctg tggcaaatcg ccggacgctt tggcgaaaca tcctgtcaat      60
atcaatgctg ctcctgaaac agaaaaagac aagacgaagt tccccggatt gtatctcgaa     120
```

-continued

```
tgaggggacc gatttccggc gttagtaaga ggtcacgtga agatggcgt gctaactagt      180 atgcaaggca tttcggctca ggcaaaatac ccagtcaaca atttgttgcc tggaggtgga      240
aatacgagac ccttgattgc gagcagtgtg tgattaggat agctgaggca ttgtattcat      300
gtatcaggaa cctgatcgtc aaagcgttgc aggctgctgg gctgggcacg tgctgcccta      360
acccttatct atctactggt ttggggtgtt tgtttatgct ccgccccgtg actctcagca      420
acggttataa cgagtagtgg cagcagccaa cgaacttctt tgctgccgac ctcacgccaa      480
acaaaagcct ttactggaaa caggctgatc agcaaatcaa gatatactag gatgagttga      540
tattatcacc ggccgcagat tactgacccg acacccttac tgcgtcatta ccctcgatc       600
```

```
aag atg ccg agt cga gtt tcc gcc cgt tca aca tcc acc gcc tcg cgc       648
    Met Pro Ser Arg Val Ser Ala Arg Ser Thr Ser Thr Ala Ser Arg
      1               5                  10                  15 aaa ggc tct aca cag act gcg aca agc ggt cgc gct ggc tca gcg acc       696
Lys Gly Ser Thr Gln Thr Ala Thr Ser Gly Arg Ala Gly Ser Ala Thr
             20                  25                  30 cca tca ttc gcc atc cca gag gaa act gca tta ccc gag gct gtt cca       744
Pro Ser Phe Ala Ile Pro Glu Glu Thr Ala Leu Pro Glu Ala Val Pro
         35                  40                  45 acc ctt cgc cgc gat gta tgc gcc att ttc gcg gat gcc cag cgt tcg       792
Thr Leu Arg Arg Asp Val Cys Ala Ile Phe Ala Asp Ala Gln Arg Ser
     50                  55                  60 act gcc ggt cat cgc aaa ctt gtc gtc cga cta agg aaa atc cag gag       840
Thr Ala Gly His Arg Lys Leu Val Val Arg Leu Arg Lys Ile Gln Glu
 65                  70                  75 gtg tgc tgt gct ata ccc cag aag aac tcc aaa aaa gac agt tca act       888
Val Cys Cys Ala Ile Pro Gln Lys Asn Ser Lys Lys Asp Ser Ser Thr
 80                  85                  90                  95 gaa gag cga ttg att ccc ggc gaa gag acg gta cca gaa aag gag ttc       936
Glu Glu Arg Leu Ile Pro Gly Glu Glu Thr Val Pro Glu Lys Glu Phe
                100                 105                 110 aac gtc gaa gta agt cgt tgt gtg ttg cgc atc ttg tct att aag aag       984
Asn Val Glu Val Ser Arg Cys Val Leu Arg Ile Leu Ser Ile Lys Lys
            115                 120                 125 aca gag cct gtt ggc gat cga atc ctg cgg ttt ctc ggg aac ttc ctt      1032
Thr Glu Pro Val Gly Asp Arg Ile Leu Arg Phe Leu Gly Asn Phe Leu
        130                 135                 140 act cat gcc tcg gaa aag gac gct gag atc ttc ggc tct gaa gaa gat      1080
Thr His Ala Ser Glu Lys Asp Ala Glu Ile Phe Gly Ser Glu Glu Asp
    145                 150                 155 gaa gac gat atg cag aat tcg cac gaa aga ccg act gcc cac ttg acc      1128
Glu Asp Asp Met Gln Asn Ser His Glu Arg Pro Thr Ala His Leu Thr
160                 165                 170                 175 acc agt ctt gtc tcc ctg tta gtg cct ttg ttg tct gca aaa gac aag      1176
Thr Ser Leu Val Ser Leu Leu Val Pro Leu Leu Ser Ala Lys Asp Lys
                180                 185                 190 gtt gtg cgc ttc cgt acc acg caa att atc gcg cac atc gtc aat tca      1224
Val Val Arg Phe Arg Thr Thr Gln Ile Ile Ala His Ile Val Asn Ser
            195                 200                 205 ctc gat acc gta gac gac gaa tta tac cac act ctc cgg caa ggc ctt      1272
Leu Asp Thr Val Asp Asp Glu Leu Tyr His Thr Leu Arg Gln Gly Leu
        210                 215                 220 cta aaa cgg att cgc gac aaa gaa cct tcg gtg cgg gta caa gca gtg      1320
Leu Lys Arg Ile Arg Asp Lys Glu Pro Ser Val Arg Val Gln Ala Val
    225                 230                 235 atg ggt ctc ggc cgc ttg gcc gga aat gaa gag gac gat gac gaa aat      1368
Met Gly Leu Gly Arg Leu Ala Gly Asn Glu Glu Asp Asp Asp Glu Asn
240                 245                 250                 255
```

-continued

| | | |
|---|---|---|
| gat gat acc agt gcc ctt gtg gag aag ctc gtg gac ata atg caa aat<br>Asp Asp Thr Ser Ala Leu Val Glu Lys Leu Val Asp Ile Met Gln Asn<br>260 265 270 | | 1416 |
| gac acg gct gca gag gtt cgg agg aca tta ctc ctc aac ctc cca ttg<br>Asp Thr Ala Ala Glu Val Arg Arg Thr Leu Leu Leu Asn Leu Pro Leu<br>275 280 285 | | 1464 |
| att ccg tct acc ctt cca tac ctc ctc gaa cgc gcc cgt gac ctc gat<br>Ile Pro Ser Thr Leu Pro Tyr Leu Leu Glu Arg Ala Arg Asp Leu Asp<br>290 295 300 | | 1512 |
| gct ccc aca cga agg gca tta tat tct cgt cta ctt ccg aca ctg gga<br>Ala Pro Thr Arg Arg Ala Leu Tyr Ser Arg Leu Leu Pro Thr Leu Gly<br>305 310 315 | | 1560 |
| gat ttc cga cat tta tct ctc tcc atg aga gaa aag ttg ctc aga tgg<br>Asp Phe Arg His Leu Ser Leu Ser Met Arg Glu Lys Leu Leu Arg Trp<br>320 325 330 335 | | 1608 |
| ggt ctt cgt gat cgc gac aaa agt gtg agg aag gcc act gga aag ttg<br>Gly Leu Arg Asp Arg Asp Lys Ser Val Arg Lys Ala Thr Gly Lys Leu<br>340 345 350 | | 1656 |
| ttc tat gac cgc tgg att gag ata tcg ctg gca cga aca atg acc ctg<br>Phe Tyr Asp Arg Trp Ile Glu Ile Ser Leu Ala Arg Thr Met Thr Leu<br>355 360 365 | | 1704 |
| aga att cgg gca gcg ctc gga acg aga att ccc gct tta ctg gag ttg<br>Arg Ile Arg Ala Ala Leu Gly Thr Arg Ile Pro Ala Leu Leu Glu Leu<br>370 375 380 | | 1752 |
| ttg gag cgt atc gat gtg gtg aac tca ggc atg gaa tcc ggc ata gcg<br>Leu Glu Arg Ile Asp Val Val Asn Ser Gly Met Glu Ser Gly Ile Ala<br>385 390 395 | | 1800 |
| cac gaa gct atg cgc agt ttc tgg gaa ggt cga cca gac tat cga gag<br>His Glu Ala Met Arg Ser Phe Trp Glu Gly Arg Pro Asp Tyr Arg Glu<br>400 405 410 415 | | 1848 |
| gcg gta cta ttc gac gaa gcc ttc tgg gag tca atg aca gca gaa tcc<br>Ala Val Leu Phe Asp Glu Ala Phe Trp Glu Ser Met Thr Ala Glu Ser<br>420 425 430 | | 1896 |
| gct ttc ctc ctt cgc tca ttc aat gac ttt tgc cgg gtt gaa aac gaa<br>Ala Phe Leu Leu Arg Ser Phe Asn Asp Phe Cys Arg Val Glu Asn Glu<br>435 440 445 | | 1944 |
| ggt aaa tat gac agc ctc gcc gat gag aag atc cca gtc gtt aca gcc<br>Gly Lys Tyr Asp Ser Leu Ala Asp Glu Lys Ile Pro Val Val Thr Ala<br>450 455 460 | | 1992 |
| ctc gca atg tat ctt cat aag tac atg acc gag ctg ctg cag cgc aag<br>Leu Ala Met Tyr Leu His Lys Tyr Met Thr Glu Leu Leu Gln Arg Lys<br>465 470 475 | | 2040 |
| aag ctc aca aag gat gct act gac gta aac gac gac gat acc gtc gaa<br>Lys Leu Thr Lys Asp Ala Thr Asp Val Asn Asp Asp Asp Thr Val Glu<br>480 485 490 495 | | 2088 |
| atc gaa ttt atc gtc gag caa ctg ctt cac atc gcg atg aca cta gac<br>Ile Glu Phe Ile Val Glu Gln Leu Leu His Ile Ala Met Thr Leu Asp<br>500 505 510 | | 2136 |
| tac agc gac gaa gtt ggg cgg cga aag atg ttt tct cta ctc cgt gag<br>Tyr Ser Asp Glu Val Gly Arg Arg Lys Met Phe Ser Leu Leu Arg Glu<br>515 520 525 | | 2184 |
| gct ctc gct gtc cca gag ctc cct cag gaa tcg acc aag ctc gcg gtt<br>Ala Leu Ala Val Pro Glu Leu Pro Gln Glu Ser Thr Lys Leu Ala Val<br>530 535 540 | | 2232 |
| gag aca ctg aga tgt gtt tgt ggg ccc gac gcc gcg gca gag agc gaa<br>Glu Thr Leu Arg Cys Val Cys Gly Pro Asp Ala Ala Ala Glu Ser Glu<br>545 550 555 | | 2280 |
| ttc tgc agt gtt gtt ctg gaa gcc att gct gaa gtt cat gac aca atc<br>Phe Cys Ser Val Val Leu Glu Ala Ile Ala Glu Val His Asp Thr Ile | | 2328 |

```
560                565                570                575 agc acc gag gat agt ttc gtt tct gca aag tct gag att agc gat gat    2376
Ser Thr Glu Asp Ser Phe Val Ser Ala Lys Ser Glu Ile Ser Asp Asp
            580                585                590 gcc agc agc cgc caa cga tcc gaa acg ccg atg agt gaa gat gac aag    2424
Ala Ser Ser Arg Gln Arg Ser Glu Thr Pro Met Ser Glu Asp Asp Lys
            595                600                605 cca ttc aac aag gag gag gca aag gct aag gtc ctc aag gaa atc gtt    2472
Pro Phe Asn Lys Glu Glu Ala Lys Ala Lys Val Leu Lys Glu Ile Val
            610                615                620 att aat atg aag tgt ctg cac att gcc ctt tgc atg ctc cag aat gtt    2520
Ile Asn Met Lys Cys Leu His Ile Ala Leu Cys Met Leu Gln Asn Val
            625                630                635 gaa ggc aac ctg caa gca aat atg aat ctg gtg acc atg ttg aat aac    2568
Glu Gly Asn Leu Gln Ala Asn Met Asn Leu Val Thr Met Leu Asn Asn
640                645                650                655 ttg gta gta cct gct gtt cgg agc cac gaa gcg cca att cga gag cgc    2616
Leu Val Val Pro Ala Val Arg Ser His Glu Ala Pro Ile Arg Glu Arg
                660                665                670 ggt ctc gaa tgt ctt ggg ctg tgc tgc ttg ctg gac aag gtaagttcca    2665
Gly Leu Glu Cys Leu Gly Leu Cys Cys Leu Leu Asp Lys
                675                680 tccttactaa atacatcttc ttctctaacc tctctgttag act ctc gca gaa gaa   2720
                                              Thr Leu Ala Glu Glu
                                                      685 aat atg acg ctg ttt att cac tgt tac agc aag ggc cac gaa aac cta   2768
Asn Met Thr Leu Phe Ile His Cys Tyr Ser Lys Gly His Glu Asn Leu
690                695                700                705 cag gtc act gct att cat atc ctt tgc gat atg tta att agc cat cct   2816
Gln Val Thr Ala Ile His Ile Leu Cys Asp Met Leu Ile Ser His Pro
                710                715                720 tcg ctg gtg gct ccc gtt acc cag gcc gat aag gag aca gtt gcg cca   2864
Ser Leu Val Ala Pro Val Thr Gln Ala Asp Lys Glu Thr Val Ala Pro
                725                730                735 ccg gcg ttc cag aag cca ctg ctt aag gtc ttt tcc aga gct ctc aaa   2912
Pro Ala Phe Gln Lys Pro Leu Leu Lys Val Phe Ser Arg Ala Leu Lys
                740                745                750 cca aat tca ccc gcg tct gta caa acg gca gct gcg aca gct ctt tct   2960
Pro Asn Ser Pro Ala Ser Val Gln Thr Ala Ala Ala Thr Ala Leu Ser
            755                760                765 aag ctt ctg ctc act ggt gtt ttt act cca tct gcc gcc aat atc ccc   3008
Lys Leu Leu Leu Thr Gly Val Phe Thr Pro Ser Ala Ala Asn Ile Pro
770                775                780                785 gat gcc att caa gag ttc aac caa cat gcc atc gaa aca ctg cta cag   3056
Asp Ala Ile Gln Glu Phe Asn Gln His Ala Ile Glu Thr Leu Leu Gln
                790                795                800 tcc ctc gtt gtc tcc ttc ttc cat ccc cga act cgc gag aat ccc gca   3104
Ser Leu Val Val Ser Phe Phe His Pro Arg Thr Arg Glu Asn Pro Ala
            805                810                815 ctc cga cag gca ctc gcg tac ttc ttc cct gtc tac tgc cac tcc cgg   3152
Leu Arg Gln Ala Leu Ala Tyr Phe Phe Pro Val Tyr Cys His Ser Arg
            820                825                830 ccg gat aac acc cag cat atg aga aag att act gta cct gtc atc cgg   3200
Pro Asp Asn Thr Gln His Met Arg Lys Ile Thr Val Pro Val Ile Arg
            835                840                845 acc atc cta aac tca gcg gaa gaa tac tac tca ctt gag gct gaa gag   3248
Thr Ile Leu Asn Ser Ala Glu Glu Tyr Tyr Ser Leu Glu Ala Glu Glu
850                855                860                865 gac agt gat ggt gat att gat gag tct gtt ggg gag aag gaa ttg aag   3296
```

```
Asp Ser Asp Gly Asp Ile Asp Glu Ser Val Gly Glu Lys Glu Leu Lys
            870                 875                 880 gcc ctg atg agc gga gtt ctt ggt atg ctt gcg gag tgg acg gat gag    3344
Ala Leu Met Ser Gly Val Leu Gly Met Leu Ala Glu Trp Thr Asp Glu
            885                 890                 895 cga aga gtg atc gga ctt ggc ggc gaa cgg gtc ctt gct ggg ggc ctt    3392
Arg Arg Val Ile Gly Leu Gly Gly Glu Arg Val Leu Ala Gly Gly Leu
            900                 905                 910 gct agc tcc aat gtt tgt ggc att atc cac ttg caa ctg att aag gac    3440
Ala Ser Ser Asn Val Cys Gly Ile Ile His Leu Gln Leu Ile Lys Asp
    915                 920                 925 ata ctg gaa cga gtg ctc ggg atc agt gaa ggc agc aat cgc tgc tct    3488
Ile Leu Glu Arg Val Leu Gly Ile Ser Glu Gly Ser Asn Arg Cys Ser
930                 935                 940                 945 aaa caa caa cga aaa ctc ctg ttt tca ctc atg agc aag ctc tat att    3536
Lys Gln Gln Arg Lys Leu Leu Phe Ser Leu Met Ser Lys Leu Tyr Ile
            950                 955                 960 gcg ccg cca acg gca ctt tcg cgc tca gcg tcc cag gcc ccc gaa gac    3584
Ala Pro Pro Thr Ala Leu Ser Arg Ser Ala Ser Gln Ala Pro Glu Asp
            965                 970                 975 gac tcg ttc cgt tcc agc gtg cga agc tcc cat ggc gaa ctc aat ccc    3632
Asp Ser Phe Arg Ser Ser Val Arg Ser Ser His Gly Glu Leu Asn Pro
            980                 985                 990 gaa aac ctt gcc ctc gcg cag gaa gtc aag gag cta ctt gac cag acc    3680
Glu Asn Leu Ala Leu Ala Gln Glu Val Lys Glu Leu Leu Asp Gln Thr
        995                 1000                1005 atc gaa gaa ggt gtg gcg gct gat gct gct agc cga aat gcc ctc gtc    3728
Ile Glu Glu Gly Val Ala Ala Asp Ala Ala Ser Arg Asn Ala Leu Val
1010                1015                1020                1025 aag gtg aag aac gtg gtg ctc aag cta ctg gcg gct ccc atg cga cct    3776
Lys Val Lys Asn Val Val Leu Lys Leu Leu Ala Ala Pro Met Arg Pro
                1030                1035                1040 tct agc gca cgc ggc cgc gag agc agt gtc gaa agt gac att ggc agt    3824
Ser Ser Ala Arg Gly Arg Glu Ser Ser Val Glu Ser Asp Ile Gly Ser
            1045                1050                1055 gtt cga tct tcc aga agt gtt cgg ccg tcc gta gag cct ggc ttt ggg    3872
Val Arg Ser Ser Arg Ser Val Arg Pro Ser Val Glu Pro Gly Phe Gly
    1060                1065                1070 cgc cgc ggt gta tcc gtg gag ccc agt atc atg gag gag gat gag aat    3920
Arg Arg Gly Val Ser Val Glu Pro Ser Ile Met Glu Glu Asp Glu Asn
1075                1080                1085 gag gat agc cgg gcg act ctg gac agt aga atg act gtt atc aaa gag    3968
Glu Asp Ser Arg Ala Thr Leu Asp Ser Arg Met Thr Val Ile Lys Glu
1090                1095                1100                1105 gag gat gcc gac gct atg gag gaa tgattttcgg tctcaagatc tttgctgtct  4022
Glu Asp Ala Asp Ala Met Glu Glu
                1110 ggttcggcgt tggggaggtt tcccggcagg gctaatggtc atatttatgg ttaggttgcg  4082 atgtaattat tcgattcttg gttatgcttg aacatgctct atatgttaca aataattcac  4142 tccaaacgtt catgtatgag tatggatctg ttttatattg gccttaccag gatagctcag  4202 ttcttggcga agttatccca gactgacagc tgcctccagg ccagaattgg ctagtcttag  4262 tcttaggtag catctgagtt atcgcgtggt atcaacagtg atcagtgtgg aagggccatc  4322 cgatctgttt gatcttacca gaacgtgtta caacaattca acccaccata tatgtggtat  4382 ctacgtcaat gtgaatgaat ctgcttgggc agccttatga ctctggtgac gcgactcggg  4442 gcttgattca atgcgggcaa gaccgcatgt ggagactcct agcatcggat gtgaggcttc  4502
```

```
cgttttaatt tcttcctcca aatcgtctgc ctgcctcgct gctttgaaat actccggagg    4562
taccaaagta aagataaatg gttgactctg agagactgct ttgacctcct ggaccaagtc    4622
gtgcctagcc agaaggggag tgttcaatgg gctttgtgag gctactaagg ccgcacgata    4682
caccggagat gcaaagaagt ccgatacggt cgtccatatc tcgagcacct ttattactgg    4742
cgcttttgca gttatatgga ggcgtttaat gattgcgtgt tcggaatccg atgaataata    4802
tctcattagt cgactaaacg gggatgagga tggatgactg ctggtatctt ggtctcaaac    4862
tgtaataagc gtctcggcaa caccgtacgg ttgacaatcc tgggcagatg gcagcacctg    4922
tagaatccaa gaagacgcag ctggactcat tgagacagtt gaattcctta actataatga    4982
cagactaata atacaaaagt gcggtggtca acttcttccc aatcccctca aaagtcagac    5042
ccgaccctgt tctttctaat aatctgacgc tccaccaaaa gtccagcttc tgggcgactt    5102 tcttttttctt ccccatcctt ttcctttccc actctcctcc ctcctctctc gcttctcttc    5162
ctttcgctgt atgttttttg ttgcttgatt cacgactttc tttttccttc tggtcgtgga    5222
tccgtgtctt ctgcccccac ttgcagaggc acgatttttc tccctctccc tctcctccct    5282
tccgtactcc ccccctcccc cctgctctgc gcctttggca tccggagcct gcgtcgagac    5342
cgtgagcgat ggcctccgtg tcagctccca cgcccaagct ggaccgctac atcgtcgttc    5402
atgtggcaac tacctgcgat gagcatggcg tctacgtcac caaggactct gcagagtgat    5462
cgagttgggg tggatcttgt tggataccaa aacctgcgag agtcgcagtg attctctccc    5522
tgcaccacac ctattccacc ccctcttttg tgtcttgatt ctcgccggcc taccgggatt    5582
ctgccgacga catt                                                     5596

<210> SEQ ID NO 2
<211> LENGTH: 684
<212> TYPE: PRT
<213> ORGANISM: Aspergillus nidulans

<400> SEQUENCE: 2

Met Pro Ser Arg Val Ser Ala Arg Ser Thr Ser Thr Ala Ser Arg Lys
  1               5                  10                  15

Gly Ser Thr Gln Thr Ala Thr Ser Gly Arg Ala Gly Ser Ala Thr Pro
             20                  25                  30

Ser Phe Ala Ile Pro Glu Glu Thr Ala Leu Pro Glu Ala Val Pro Thr
         35                  40                  45

Leu Arg Arg Asp Val Cys Ala Ile Phe Ala Asp Ala Gln Arg Ser Thr
     50                  55                  60

Ala Gly His Arg Lys Leu Val Val Arg Leu Arg Lys Ile Gln Glu Val
 65                  70                  75                  80

Cys Cys Ala Ile Pro Gln Lys Asn Ser Lys Lys Asp Ser Ser Thr Glu
                 85                  90                  95

Glu Arg Leu Ile Pro Gly Glu Glu Thr Val Pro Glu Lys Glu Phe Asn
            100                 105                 110

Val Glu Val Ser Arg Cys Val Leu Arg Ile Leu Ser Ile Lys Lys Thr
        115                 120                 125

Glu Pro Val Gly Asp Arg Ile Leu Arg Phe Leu Gly Asn Phe Leu Thr
    130                 135                 140

His Ala Ser Glu Lys Asp Ala Glu Ile Phe Gly Ser Glu Glu Asp Glu
145                 150                 155                 160

Asp Asp Met Gln Asn Ser His Gly Arg Pro Thr Ala His Leu Thr Thr
                165                 170                 175
```

```
Ser Leu Val Ser Leu Leu Val Pro Leu Leu Ser Ala Lys Asp Lys Val
            180                 185                 190

Val Arg Phe Arg Thr Thr Gln Ile Ile Ala His Ile Val Asn Ser Leu
        195                 200                 205

Asp Thr Val Asp Asp Glu Leu Tyr His Thr Leu Arg Gln Gly Leu Leu
        210                 215                 220

Lys Arg Ile Arg Asp Lys Glu Pro Ser Val Arg Val Gln Ala Val Met
225                 230                 235                 240

Gly Leu Gly Arg Leu Ala Gly Asn Glu Glu Asp Asp Asp Glu Asn Asp
                245                 250                 255

Asp Thr Ser Ala Leu Val Glu Lys Leu Val Asp Ile Met Gln Asn Asp
        260                 265                 270

Thr Ala Ala Glu Val Arg Arg Thr Leu Leu Leu Asn Leu Pro Leu Ile
        275                 280                 285

Pro Ser Thr Leu Pro Tyr Leu Leu Glu Arg Ala Arg Asp Leu Asp Ala
        290                 295                 300

Pro Thr Arg Arg Ala Leu Tyr Ser Arg Leu Leu Pro Thr Leu Gly Asp
305                 310                 315                 320

Phe Arg His Leu Ser Leu Ser Met Arg Glu Lys Leu Leu Arg Trp Gly
                325                 330                 335

Leu Arg Asp Arg Asp Lys Ser Val Arg Lys Ala Thr Gly Lys Leu Phe
                340                 345                 350

Tyr Asp Arg Trp Ile Glu Ile Ser Leu Ala Arg Thr Met Thr Leu Arg
        355                 360                 365

Ile Arg Ala Ala Leu Gly Thr Arg Ile Pro Ala Leu Leu Glu Leu Leu
        370                 375                 380

Glu Arg Ile Asp Val Val Asn Ser Gly Met Glu Ser Gly Ile Ala His
385                 390                 395                 400

Glu Ala Met Arg Ser Phe Trp Glu Gly Arg Pro Asp Tyr Arg Glu Ala
                405                 410                 415

Val Leu Phe Asp Glu Ala Phe Trp Glu Ser Met Thr Ala Glu Ser Ala
                420                 425                 430

Phe Leu Leu Arg Ser Phe Asn Asp Phe Cys Arg Val Glu Asn Glu Gly
            435                 440                 445

Lys Tyr Asp Ser Leu Ala Asp Glu Lys Ile Pro Val Val Thr Ala Leu
450                 455                 460

Ala Met Tyr Leu His Lys Tyr Met Thr Glu Leu Leu Gln Arg Lys Lys
465                 470                 475                 480

Leu Thr Lys Asp Ala Thr Asp Val Asn Asp Asp Thr Val Glu Ile
                485                 490                 495

Glu Phe Ile Val Glu Gln Leu Leu His Ile Ala Met Thr Leu Asp Tyr
            500                 505                 510

Ser Asp Glu Val Gly Arg Arg Lys Met Phe Ser Leu Leu Arg Glu Ala
            515                 520                 525

Leu Ala Val Pro Glu Leu Pro Gln Glu Ser Thr Lys Leu Ala Val Glu
        530                 535                 540

Thr Leu Arg Cys Val Cys Gly Pro Asp Ala Ala Glu Ser Glu Phe
545                 550                 555                 560

Cys Ser Val Val Leu Glu Ala Ile Ala Glu Val His Asp Thr Ile Ser
                565                 570                 575

Thr Glu Asp Ser Phe Val Ser Ala Lys Ser Glu Ile Ser Asp Asp Ala
        580                 585                 590

Ser Ser Arg Gln Arg Ser Glu Thr Pro Met Ser Glu Asp Asp Lys Pro
```

```
                595             600                 605
    Phe Asn Lys Glu Glu Ala Lys Ala Lys Val Leu Lys Glu Ile Val Ile
            610                 615                 620

Asn Met Lys Cys Leu His Ile Ala Leu Cys Met Leu Gln Asn Val Glu
    625                 630                 635                 640

Gly Asn Leu Gln Ala Asn Met Asn Leu Val Thr Met Leu Asn Asn Leu
                    645                 650                 655

Val Val Pro Ala Val Arg Ser His Glu Ala Pro Ile Arg Glu Arg Gly
                660                 665                 670

Leu Glu Cys Leu Gly Leu Cys Cys Leu Leu Asp Lys
                675                 680

<210> SEQ ID NO 3
<211> LENGTH: 5596
<212> TYPE: DNA
<213> ORGANISM: Aspergillus nidulans

<400> SEQUENCE: 3
aatgtcgtcg gcagaatccc ggtaggccgg cgagaatcaa gacacaaaag aggggtgga       60 ataggtgtgg tgcagggaga gaatcactgc gactctcgca ggttttggta tccaacaaga     120 tccacccaa ctcgatcact ctgcagagtc cttggtgacg tagacgccat gctcatcgca     180
ggtagttgcc acatgaacga cgatgtagcg gtccagcttg ggcgtgggag ctgacacgga     240
ggccatcgct cacggtctcg acgcaggctc cggatgccaa aggcgcagag caggggggag     300 gggggagta cggaagggag gagagggaga gggagaaaaa tcgtgcctct gcaagtgggg     360
gcagaagaca cggatccacg accagaagga aaagaaagt cgtgaatcaa gcaacaaaaa     420
acatacagcg aaaggaagag aagcgagaga ggagggagga gagtgggaaa ggaaaaggat     480
ggggaagaaa aagaaagtcg cccagaagct ggacttttgg tggagcgtca gattattaga     540
aagaacaggg tcgggtctga cttttgaggg gattgggaag aagttgacca ccgcactttt     600
gtattattag tctgtcatta tagttaagga attcaactgt ctcaatgagt ccagctgcgt     660
cttcttggat tctacaggtg ctgccatctg cccaggattg tcaaccgtac ggtgttgccg     720
agacgcttat tacagtttga gaccaagata ccagcagtca tccatcctca tcccgttta     780 gtcgactaat gagatattat tcatcggatt ccgaacacgc aatcattaaa cgcctccata     840
taactgcaaa agcgccagta ataaaggtgc tcgagatatg gacgaccgta tcggacttct     900
ttgcatctcc ggtgtatcgt gcggccttag tagcctcaca aagcccattg aacactcccc     960
ttctggctag gcacgacttg gtccaggagg tcaaagcagt ctctcagagt caaccattta    1020
tctttacttt ggtacctccg gagtatttca agcagcgag gcaggcagac gatttggagg     1080
aagaaattaa aacggaagcc tcacatccga tgctaggagt ctccacatgc ggtcttgccc     1140
gcattgaatc aagcccccgag tcgcgtcacc agagtcataa ggctgcccaa gcagattcat     1200
tcacattgac gtagatacca tatatatggt gggttgaatt gttgtaacac gttctggtaa     1260
gatcaaacag atcggatggc ccttccacac tgatcactgt tgataccacg cgataactca     1320
gatgctacct aagactaaga ctagccaatt ctggcctgga ggcagctgtc agtctgggat     1380
aacttcgcca agaactgagc tatcctggta aggccaatat aaaacagatc catactcata     1440
catgaacgtt tggagtgaat tatttgtaac atatagagca tgttcaagca taaccaagaa     1500
tcgaataatt acatcgcaac ctaaccataa atatgaccat tagccctgcc gggaaacctc     1560
cccaacgccg aaccagacag caaagatctt gagaccgaaa atcattcctc catagcgtcg    1620
```

```
gcatcctcct ctttgataac agtcattcta ctgtccagag tcgcccggct atcctcattc      1680
tcatcctcct ccatgatact gggctccacg gatacaccgc ggcgcccaaa gccaggctct      1740
acggacggcc gaacacttct ggaagatcga acactgccaa tgtcactttc gacactgctc      1800
tcgcggccgc gtgcgctaga aggtcgcatg ggagccgcca gtagcttgag caccacgttc      1860
ttcaccttga cgagggcatt tcggctagca gcatcagccg ccacaccttc ttcgatggtc      1920
tggtcaagta gctccttgac ttcctgcgcg agggcaaggt tttcgggatt gagttcgcca      1980
tgggagcttc gcacgctgga acggaacgag tcgtcttcgg gggcctggga cgctgagcgc      2040
gaaagtgccg ttgcggcgc aatatagagc ttgctcatga gtgaaaacag gagttttcgt      2100
tgttgtttag agcagcgatt gctgccttca ctgatcccga gcactcgttc cagtatgtcc      2160
ttaatcagtt gcaagtggat aatgccacaa acattggagc tagcaaggcc cccagcaagg      2220
acccgttcgc cgccaagtcc gatcactctt cgctcatccg tccactccgc aagcatacca      2280
agaactccgc tcatcagggc cttcaattcc ttctccccaa cagactcatc aatatcacca      2340
tcactgtcct cttcagcctc aagtgagtag tattcttccg ctgagtttag gatggtccgg      2400
atgacaggta cagtaatctt tctcatatgc tgggtgttat ccggccggga gtggcagtag      2460
acagggaaga agtacgcgag tgcctgtcgg agtgcgggat tctcgcgagt tcggggatgg      2520
aagaaggaga caacgaggga ctgtagcagt gtttcgatgg catgttggtt gaactcttga      2580
atggcatcgg ggatattggc ggcagatgga gtaaaaacac cagtgagcag aagcttagaa      2640
agagctgtcg cagctgccgt ttgtacagac gcgggtgaat ttggtttgag agctctggaa      2700
aagaccttaa gcagtggctt ctggaacgcc ggtggcgcaa ctgtctcctt atcggcctgg      2760
gtaacgggag ccaccagcga aggatggcta attaacatat cgcaaaggat atgaatagca      2820
gtgacctgta ggttttcgtg gcccttgctg taacagtgaa taaacagcgt catattttct      2880
tctgcgagag tctaacagag aggttagaga agaagatgta tttagtaagg atggaactta      2940
ccttgtccag caagcagcac agcccaagac attcgagacc gcgctctcga attggcgctt      3000
cgtggctccg aacagcaggt actaccaagt tattcaacat ggtcaccaga ttcatatttg      3060
cttgcaggtt gccttcaaca ttctggagca tgcaaagggc aatgtgcaga cacttcatat      3120
taataacgat ttccttgagg accttagcct ttgcctcctc cttgttgaat ggcttgtcat      3180
cttcactcat cggcgtttcg gatcgttggc ggctgctggc atcatcgcta atctcagact      3240
ttgcagaaac gaaactatcc tcggtgctga ttgtgtcatg aacttcagca atggcttcca      3300
gaacaacact gcagaattcg ctctctgccg cggcgtcggg cccacaaaca catctcagtg      3360
tctcaaccgc gagcttggtc gattcctgag ggagctctgg gacagcgaga gcctcacgga      3420
gtagagaaaa catctttcgc cgcccaactt cgtcgctgta gtctagtgtc atcgcgatgt      3480
gaagcagttg ctcgacgata aattcgattt cgacggtatc gtcgtcgttt acgtcagtag      3540
catcctttgt gagcttcttg cgctgcagaa gctcggtcat gtacttatga agatacattg      3600
cgagggctgt aacgactggg atcttctcat cggcgaggct gtcatattta ccttcgtttt      3660
caacccggca aaagtcattg aatgagcgaa ggaggaaagc ggattctgct gtcattgact      3720
cccagaaggc ttcgtcgaat agtaccgcct ctcgatagtc tggtcgacct tcccagaaac      3780
tgcgcatagc ttcgtgcgct atgccggatt ccatgcctga gttcaccaca tcgatacgct      3840
ccaacaactc cagtaaagcg ggaattctcg ttccgagcgc tgcccgaatt ctcagggtca      3900
ttgttcgtgc cagcgatatc tcaatccagc ggtcatagaa caacttttcca gtggccttcc      3960 tcacactttt gtcgcgatca cgaagacccc atctgagcaa cttttctctc atggagagag      4020
```

-continued

```
ataaatgtcg gaaatctccc agtgtcggaa gtagacgaga atataatgcc cttcgtgtgg    4080
gagcatcgag gtcacgggcg cgttcgagga ggtatggaag ggtagacgga atcaatggga    4140
ggttgaggag taatgtcctc cgaacctctg cagccgtgtc attttgcatt atgtccacga    4200
gcttctccac aagggcactg gtatcatcat tttcgtcatc gtcctcttca tttccggcca    4260
agcggccgag acccatcact gcttgtaccc gcaccgaagg ttctttgtcg cgaatccgtt    4320
ttagaaggcc ttgccggaga gtgtggtata attcgtcgtc tacggtatcg agtgaattga    4380
cgatgtgcgc gataatttgc gtggtacgga agcgcacaac cttgtctttt gcagacaaca    4440
aaggcactaa cagggagaca agactggtgg tcaagtgggc agtcggtctt tcgtgcgaat    4500
tctgcatatc gtcttcatct tcttcagagc cgaagatctc agcgtccttt tccgaggcat    4560
gagtaaggaa gttcccgaga accgcagga ttcgatcgcc aacaggctct gtcttcttaa     4620
tagacaagat gcgcaacaca caacgactta cttcgacgtt gaactccttt tctggtaccg    4680
tctcttcgcc gggaatcaat cgctcttcag ttgaactgtc ttttttggag ttcttctggg    4740
gtatagcaca gcacacctcc tggattttcc ttagtcggac gacaagtttg cgatgaccgg    4800
cagtcgaacg ctgggcatcc gcgaaaatgg cgcatacatc gcggcgaagg gttggaacag    4860
cctcgggtaa tgcagtttcc tctgggatgg cgaatgatgg ggtcgctgag ccagcgcgac    4920
cgcttgtcgc agtctgtgta gagcctttgc gcgaggcggt ggatgttgaa cgggcggaaa    4980
ctcgactcgg catcttgatc gagggtaat gacgcagtaa gggtgtcggg tcagtaatct     5040
gcggccggtg ataatatcaa ctcatcctag tatatcttga tttgctgatc agcctgtttc    5100
cagtaaaggc ttttgtttgg cgtgaggtcg gcagcaaaga agttcgttgg ctgctgccac    5160
tactcgttat aaccgttgct gagagtcacg gggcggagca taaacaaaca ccccaaacca    5220
gtagatagat aagggttagg gcagcacgtg cccagcccag cagcctgcaa cgctttgacg    5280
atcaggttcc tgatacatga atacaatgcc tcagctatcc taatcacaca ctgctcgcaa    5340
tcaagggtct cgtatttcca cctccaggca acaaattgtt gactgggtat tttgcctgag    5400
ccgaaatgcc ttgcatacta gttagcacgc catctttcac gtgacctctt actaacgccg    5460
gaaatcggtc ccctcattcg agatacaatc cggggaactt cgtcttgtct ttttctgttt    5520
caggagcagc attgatattg acaggatgtt tcgccaaagc gtccggcgat ttgccacagc    5580
tgccctgcgc agcgct                                                    5596
```

<210> SEQ ID NO 4
<211> LENGTH: 1758
<212> TYPE: DNA
<213> ORGANISM: Aspergillus nidulans
<220> FEATURE:
<221> NAME/KEY: CDS
<222> LOCATION: (162)...(1319)

<400> SEQUENCE: 4

```
caaaagtctt gatcacaggg gcacaagcgc aattgagcca ccatgcttac ggacggcatc     60 gaagggtca aggagaaagt ctttgtgctc gtgaccggtg ccaacaggta cagtgaaacc     120
ctgcgctctg tctcctatct catgcggtcc gttagtggtt t atg ttt cta act gtt    176
                                            Met Phe Leu Thr Val
                                             1               5 acc cct tgt ggg ttt tca ccg ttt agc gga cta gga tac tca acg tgt    224
Thr Pro Cys Gly Phe Ser Pro Phe Ser Gly Leu Gly Tyr Ser Thr Cys
         10                  15                  20 tgc cgt ctt gca gat gaa ttc ctg gcg tct cat cgg aac gac cat cgt    272
```

```
                                                          -continued

Cys Arg Leu Ala Asp Glu Phe Leu Ala Ser His Arg Asn Asp His Arg
         25                  30                  35 tca ttg aca atc atc ttc act acc cgg agc aca aga aag gga agc gac        320
Ser Leu Thr Ile Ile Phe Thr Thr Arg Ser Thr Arg Lys Gly Ser Asp
         40                  45                  50 acc ctt cgc aac cta cag aat cac ctc cgc acc tcc acc ttc ggt gct        368
Thr Leu Arg Asn Leu Gln Asn His Leu Arg Thr Ser Thr Phe Gly Ala
     55                  60                  65 tcg gcc acc gct cga gtg acc ttc gtt cct gaa aat gtc gac ctc tgc        416
Ser Ala Thr Ala Arg Val Thr Phe Val Pro Glu Asn Val Asp Leu Cys
 70                  75                  80                  85 aac ctc ctc tcg gtc cgc gcg cta tcc cgt cgc ctg aac aag acc ttc        464
Asn Leu Leu Ser Val Arg Ala Leu Ser Arg Arg Leu Asn Lys Thr Phe
                 90                  95                 100 cca aaa ctc gac gcg att gtg ctt aat gcc ggg ata ggg ggt tgg tct        512
Pro Lys Leu Asp Ala Ile Val Leu Asn Ala Gly Ile Gly Gly Trp Ser
            105                 110                 115 ggc ctc aat tgg cct ctg gcc gta tgg agc gtt tgc acc gac att atc        560
Gly Leu Asn Trp Pro Leu Ala Val Trp Ser Val Cys Thr Asp Ile Ile
        120                 125                 130 cat gcg acg acg tgg cca aag tac aaa att gcg cct gta ggt ctc ata        608
His Ala Thr Thr Trp Pro Lys Tyr Lys Ile Ala Pro Val Gly Leu Ile
    135                 140                 145 acg gac aac cag aca att act gtg acc gac aag gag ccc cgc ctg gga        656
Thr Asp Asn Gln Thr Ile Thr Val Thr Asp Lys Glu Pro Arg Leu Gly
150                 155                 160                 165 acc gtc ttc tgc gcc aac gtc ttc ggc cac tac atg ctc gcg cat aat        704
Thr Val Phe Cys Ala Asn Val Phe Gly His Tyr Met Leu Ala His Asn
                170                 175                 180 gtc atg cct ctc ctg cac cga tcc gga tcc ccc aac gga ccc gga cgc        752
Val Met Pro Leu Leu His Arg Ser Gly Ser Pro Asn Gly Pro Gly Arg
            185                 190                 195 gtg ata tgg ctc tcc agc act gaa gcc acg atc aac ttc ttc gat gtt        800
Val Ile Trp Leu Ser Ser Thr Glu Ala Thr Ile Asn Phe Phe Asp Val
        200                 205                 210 gat gat ttt cag gcg ctc cgg tcc aaa gct ccc tac gag tca tca aaa        848
Asp Asp Phe Gln Ala Leu Arg Ser Lys Ala Pro Tyr Glu Ser Ser Lys
    215                 220                 225 gcg cta aca gac ctc cta tcc ctc acc tca gac ctt ccc agt act gct        896
Ala Leu Thr Asp Leu Leu Ser Leu Thr Ser Asp Leu Pro Ser Thr Ala
230                 235                 240                 245 ccc tgg gtg aaa agc ttc tat tcc acc gac ttc gaa acc gat tcc aag        944
Pro Trp Val Lys Ser Phe Tyr Ser Thr Asp Phe Glu Thr Asp Ser Lys
                250                 255                 260 ccc agc acc gga cct gag acc gcc tcg acc ata ccc aac gta tac ctc        992
Pro Ser Thr Gly Pro Glu Thr Ala Ser Thr Ile Pro Asn Val Tyr Leu
            265                 270                 275 tct cac ccc gga atc tgc gct acg gcg att ata ccc ctt cct aca atc       1040
Ser His Pro Gly Ile Cys Ala Thr Ala Ile Ile Pro Leu Pro Thr Ile
        280                 285                 290 ctc atc tac gca atg gtc gcc gca ttt tgg cta gcc cgc atc ctc ggc       1088
Leu Ile Tyr Ala Met Val Ala Ala Phe Trp Leu Ala Arg Ile Leu Gly
    295                 300                 305 tcc cct tgg cat acc tta tcc acc tac cta ggc gct tgc agc cct gtc       1136
Ser Pro Trp His Thr Leu Ser Thr Tyr Leu Gly Ala Cys Ser Pro Val
310                 315                 320                 325 tgg ctt gct ctc tcc aca caa tca gaa ctc gac gcc gcc gaa gca ccg       1184
Trp Leu Ala Leu Ser Thr Gln Ser Glu Leu Asp Ala Ala Glu Ala Pro
                330                 335                 340
```

```
tac cgg aaa cac ggc ggc agg gtg aaa tgg ggg tct tcg gcg tct    1232
Tyr Arg Lys His Gly Gly Arg Val Lys Trp Gly Ser Ser Ala Ser
            345                 350                 355 cga tta ggt gta gcc tcc gtc gta tct tcg gag gtt gac gga tgg ggc    1280
Arg Leu Gly Val Ala Ser Val Val Ser Ser Glu Val Asp Gly Trp Gly
        360                 365                 370 tat ggg ggt gtt cct ggg gcc ggc tgt tgt ggc gga gga tagggtctga    1329
Tyr Gly Gly Val Pro Gly Ala Gly Cys Cys Gly Gly Gly
    375                 380                 385 aggcgcaagc gtggtgcagt ggatcttacg gctgagggga aggagggatt ccaggaactg    1389
ggggctatat gttggaggca gatggaggag ctgaggatcc tgtgggataa cttacttgat    1449
gaagagagaa ggggactggt gtgacggcgt aggtggcttg tcctgggagt gagatctctt    1509
acatttcggc cttcgtccct aaaatccttt tctcccttcc tctttattat acgatgtcgg    1569
cggttttatg ttcaatacag cacatctacg gtacaaagac aacatatagc taatataata    1629
tcatagataa tagtaataat caagcacaaa agctcgattc tgcaagatct caatatcttt    1689
attccagttt tcactgctct tgtcttccat atttacattc cacgtccacg tgcatccttt    1749
aaaaacagt                                                            1758

<210> SEQ ID NO 5
<211> LENGTH: 386
<212> TYPE: PRT
<213> ORGANISM: Aspergillus nidulans

<400> SEQUENCE: 5

Met Phe Leu Thr Val Thr Pro Cys Gly Phe Ser Pro Phe Ser Gly Leu
 1               5                  10                  15

Gly Tyr Ser Thr Cys Cys Arg Leu Ala Asp Glu Phe Leu Ala Ser His
                20                  25                  30

Arg Asn Asp His Arg Ser Leu Thr Ile Ile Phe Thr Thr Arg Ser Thr
            35                  40                  45

Arg Lys Gly Ser Asp Thr Leu Arg Asn Leu Gln Asn His Leu Arg Thr
        50                  55                  60

Ser Thr Phe Gly Ala Ser Ala Thr Ala Arg Val Thr Phe Val Pro Glu
 65                  70                  75                  80

Asn Val Asp Leu Cys Asn Leu Leu Ser Val Arg Ala Leu Ser Arg Arg
                85                  90                  95

Leu Asn Lys Thr Phe Pro Lys Leu Asp Ala Ile Val Leu Asn Ala Gly
            100                 105                 110

Ile Gly Gly Trp Ser Gly Leu Asn Trp Pro Leu Ala Val Trp Ser Val
        115                 120                 125

Cys Thr Asp Ile Ile His Ala Thr Thr Trp Pro Lys Tyr Lys Ile Ala
130                 135                 140

Pro Val Gly Leu Ile Thr Asp Asn Gln Thr Ile Thr Val Thr Asp Lys
145                 150                 155                 160

Glu Pro Arg Leu Gly Thr Val Phe Cys Ala Asn Val Phe Gly His Tyr
                165                 170                 175

Met Leu Ala His Asn Val Met Pro Leu Leu His Arg Ser Gly Ser Pro
            180                 185                 190

Asn Gly Pro Gly Arg Val Ile Trp Leu Ser Ser Thr Glu Ala Thr Ile
        195                 200                 205

Asn Phe Phe Asp Val Asp Phe Gln Ala Leu Arg Ser Lys Ala Pro
        210                 215                 220

Tyr Glu Ser Ser Lys Ala Leu Thr Asp Leu Leu Ser Leu Thr Ser Asp
```

```
225                 230                 235                 240
Leu Pro Ser Thr Ala Pro Trp Val Lys Ser Phe Tyr Ser Thr Asp Phe
                245                 250                 255
Glu Thr Asp Ser Lys Pro Ser Thr Gly Pro Glu Thr Ala Ser Thr Ile
            260                 265                 270
Pro Asn Val Tyr Leu Ser His Pro Gly Ile Cys Ala Thr Ala Ile Ile
        275                 280                 285
Pro Leu Pro Thr Ile Leu Ile Tyr Ala Met Val Ala Ala Phe Trp Leu
    290                 295                 300
Ala Arg Ile Leu Gly Ser Pro Trp His Thr Leu Ser Thr Tyr Leu Gly
305                 310                 315                 320
Ala Cys Ser Pro Val Trp Leu Ala Leu Ser Thr Gln Ser Glu Leu Asp
                325                 330                 335
Ala Ala Glu Ala Pro Tyr Arg Lys His Gly Gly Gly Arg Val Lys Trp
            340                 345                 350
Gly Ser Ser Ala Ser Arg Leu Gly Val Ala Ser Val Val Ser Ser Glu
        355                 360                 365
Val Asp Gly Trp Gly Tyr Gly Val Pro Gly Ala Gly Cys Cys Gly
    370                 375                 380
ly Gly
385

<210> SEQ ID NO 6
<211> LENGTH: 1758
<212> TYPE: DNA
<213> ORGANISM: Aspergillus nidulans

<400> SEQUENCE: 6
actgttttta aaggatgcac gtggacgtgg aatgtaaata tggaagacaa gagcagtgaa      60
aactggaata aagatattga gatcttgcag aatcgagctt ttgtgcttga ttattactat     120
tatctatgat attatattag ctatatgttg tctttgtacc gtagatgtgc tgtattgaac     180
ataaaaccgc cgacatcgta taataaagag gaagggagaa aaggatttta gggacgaagg     240
ccgaaatgta agagatctca ctcccaggac aagccaccta cgccgtcaca ccagtcccct     300
tctctcttca tcaagtaagt tatcccacag gatcctcagc tcctccatct gcctccaaca     360
tatagccccc agttcctgga atccctcctt cccctcagcc gtaagatcca ctgcaccacg     420
cttgcgcctt cagaccctat cctccgccac aacagccggc cccaggaaca cccccatagc     480
cccatccgtc aacctccgaa gatacgacgg aggctacacc taatcgagac gccgaagacc     540
cccatttcac cctgccgccg ccgtgtttcc ggtacggtgc ttcggcggcg tcgagttctg     600
attgtgtgga gagagcaagc cagacagggc tgcaagcgcc taggtaggtg gataaggtat     660
gccaagggga gccgaggatg cgggctagcc aaaatgcggc gaccattgcg tagatgagga     720
ttgtaggaag gggtataatc gccgtagcgc agattccggg gtgagagagg tatacgttgg     780
gtatggtcga ggcggtctca ggtccggtgc tgggcttgga atcggtttcg aagtcggtgg     840
aatagaagct tttcacccag ggagcagtac tgggaaggtc tgaggtgagg ataggaggt     900
ctgttagcgc ttttgatgac tcgtaggtag ctttggaccg gagcgcctga aaatcatcaa     960
catcgaagaa gttgatcgtg gcttcagtgc tggagagcca tatcacgcgt ccgggtccgt    1020
tggggggatcc ggatcggtgc aggagaggca tgacattatg cgcgagcatg tagtggccga    1080
agacgttggc gcagaagacg gttccaggc ggggctcctt gtcggtcaca gtaattgtct    1140
ggttgtccgt tatgagacct acaggcgcaa ttttgtactt tggccacgtc gtcgcatgga    1200
```

-continued

```
taatgtcggt gcaaacgctc catacggcca gaggccaatt gaggccagac caaccccta      1260 tcccggcatt aagcacaatc gcgtcgagtt tgggaaggt cttgttcagg cgacgggata      1320
gcgcgcggac cgagaggagg ttgcagaggt cgacattttc aggaacgaag gtcactcgag      1380
cggtggccga agcaccgaag gtggaggtgc ggaggtgatt ctgtaggttg cgaagggtgt      1440
cgcttccctt tcttgtgctc cgggtagtga agatgattgt caatgaacga tggtcgttcc      1500
gatgagacgc caggaattca tctgcaagac ggcaacacgt tgagtatcct agtccgctaa      1560
acggtgaaaa cccacaaggg gtaacagtta gaaacataaa ccactaacgg accgcatgag      1620
ataggagaca gagcgcaggg tttcactgta cctgttggca ccggtcacga gcacaaagac      1680
tttctccttg acccttcga tgccgtccgt aagcatggtg gctcaattgc gcttgtgccc      1740
ctgtgatcaa gacttttg                                                    1758
```

<210> SEQ ID NO 7
<211> LENGTH: 1792
<212> TYPE: DNA
<213> ORGANISM: Aspergillus nidulans
<220> FEATURE:
<221> NAME/KEY: CDS
<222> LOCATION: (230)...(309)
<221> NAME/KEY: CDS
<222> LOCATION: (375)...(815)
<221> NAME/KEY: CDS
<222> LOCATION: (876)...(1149)
<221> NAME/KEY: CDS
<222> LOCATION: (1200)...(1475)

<400> SEQUENCE: 7

```
gaattcctgt gatggagcag aacctcggag tatgctccga tgtcagtaca ttaaattttg       60
tagcgatcca cgtgatttct attttgcgtc cgcaataggt cttctgatac ggctgaagaa      120
atatagtacg tggtccagtg cctatagacg gaaagtattt tcgtacggtt ggctcccaag      180
gcaataggtc aacctcgcat acggagaata acggtacggt cctgaagga atg agg gga      238
                                                        Met Arg Gly
                                                          1 tgt att ctc ctt ctc cga ggg cca gaa ggg gaa cag gcc cgc act gat         286
Cys Ile Leu Leu Leu Arg Gly Pro Glu Gly Glu Gln Ala Arg Thr Asp
  5                  10                  15 ccg gcg aaa att tcc cct ctc ga gtcttcgctc tccccccac acggctgact         339
Pro Ala Lys Ile Ser Pro Leu Asp
 20                  25 aaccctccca ttcttgcccg catccagcca gccag c ctt ttg tcg ccg ccc ttg        393
                                       Leu Leu Ser Pro Pro Leu
                                                        30 gtt cgg gct act gtc atc ttc cct tct tca tct tca tgc cgc tct cga         441
Val Arg Ala Thr Val Ile Phe Pro Ser Ser Ser Ser Cys Arg Ser Arg
 35                  40                  45 ctg aaa tat tca gtc tct tgc tct gat tta cag tta cta cgc gca gac         489
Leu Lys Tyr Ser Val Ser Cys Ser Asp Leu Gln Leu Leu Arg Ala Asp
 50                  55                  60                  65 acg ctg cac atc tcc gcg atc atg acc gaa tcc act caa gaa cag ggc         537
Thr Leu His Ile Ser Ala Ile Met Thr Glu Ser Thr Gln Glu Gln Gly
                 70                  75                  80 aac gat ggc cag cga atg ccc ccc gcc ccg gcg acc ccc gtt gag gat         585
Asn Asp Gly Gln Arg Met Pro Pro Ala Pro Ala Thr Pro Val Glu Asp
             85                  90                  95 tac gtc ttc cct gaa tat cgc ctg aag cgt gtg atg gat gac ccg gaa         633
Tyr Val Phe Pro Glu Tyr Arg Leu Lys Arg Val Met Asp Asp Pro Glu
        100                 105                 110
```

```
aag acg ccg cta ttg ctt ata gct tgc ggt tca ttc tca cct att acg      681
Lys Thr Pro Leu Leu Leu Ile Ala Cys Gly Ser Phe Ser Pro Ile Thr
    115                 120                 125 ttc ctg cac ctg cgc atg ttc gaa atg gcc gcc gat tac gtc aaa ctg      729
Phe Leu His Leu Arg Met Phe Glu Met Ala Ala Asp Tyr Val Lys Leu
130                 135                 140                 145 agc aca gat ttc gaa ata att gga ggt tat ctt tcg ccc gtc tcg gac      777
Ser Thr Asp Phe Glu Ile Ile Gly Gly Tyr Leu Ser Pro Val Ser Asp
                150                 155                 160 gcc tac cgc aag gca ggt ctt gcg agt gcc aat cac ag gtagttactt        825
Ala Tyr Arg Lys Ala Gly Leu Ala Ser Ala Asn His Arg
                165                 170 taacacactt cttccatagt tactatccag gactgatctg gcggctttag a att gca     882
                                                        Ile Ala
                                                            175 atg tgc caa cga gcc gtg gac caa acg tca gac tgg atg atg gtg gat      930
Met Cys Gln Arg Ala Val Asp Gln Thr Ser Asp Trp Met Met Val Asp
            180                 185                 190 aca tgg gag ccg atg cac aag gag tac cag cca act gcc atc gta ctg      978
Thr Trp Glu Pro Met His Lys Glu Tyr Gln Pro Thr Ala Ile Val Leu
        195                 200                 205 gat cat ttt gac tac gag atc aac act gtc cgc aaa ggt atc gat acc     1026
Asp His Phe Asp Tyr Glu Ile Asn Thr Val Arg Lys Gly Ile Asp Thr
210                 215                 220 gga aaa ggc act cga aag cga gtg caa gtc gtc tta ttg gcc ggg gca     1074
Gly Lys Gly Thr Arg Lys Arg Val Gln Val Val Leu Leu Ala Gly Ala
225                 230                 235                 240 gat ttg gtc cat acc atg tct acg ccc gga gta tgg agt gag aag gat     1122
Asp Leu Val His Thr Met Ser Thr Pro Gly Val Trp Ser Glu Lys Asp
                245                 250                 255 ctc gat cat att ctt gga cag tac ggg gtatgttatg ttgtatctat           1169
Leu Asp His Ile Leu Gly Gln Tyr Gly
                260                 265 cctaaacttc gcgcaagcta actggtctag act ttc atc gtc gag cga agc ggg    1223
                                 Thr Phe Ile Val Glu Arg Ser Gly
                                                         270 aca gat att gac gag gcg ctc gcg gca ttg cag cca tgg aaa aag aat     1271
Thr Asp Ile Asp Glu Ala Leu Ala Ala Leu Gln Pro Trp Lys Lys Asn
275                 280                 285 atc cat gtt att caa caa ctt att caa aat gac gtt agc agc act aag     1319
Ile His Val Ile Gln Gln Leu Ile Gln Asn Asp Val Ser Ser Thr Lys
290                 295                 300                 305 att cgc tta ttc ctc agg cga gat atg agc gta cgc tac ttg atc cct     1367
Ile Arg Leu Phe Leu Arg Arg Asp Met Ser Val Arg Tyr Leu Ile Pro
                310                 315                 320 gac ccg gtg att gag tac atc tat gag aat aac ctc tac atg gac gac     1415
Asp Pro Val Ile Glu Tyr Ile Tyr Glu Asn Asn Leu Tyr Met Asp Asp
            325                 330                 335 ggt acg aca caa ccg acg gcc gac aag ggc aag aca cga gag gag ccc     1463
Gly Thr Thr Gln Pro Thr Ala Asp Lys Gly Lys Thr Arg Glu Glu Pro
        340                 345                 350 gcg cct tca aat tagcattgct caaaaagcca gataaggcca cgcgacgacg         1515
Ala Pro Ser Asn
    355 tcatgacgac cattgctggt ttcacgaaga tatcaaaccg ccgggcgaat gcaatctctg   1575 cgctgatctg agcaagcact gattccggta agccgcaagt tgggggagga tttaatgagc  1635 ccaaccgtat gggtttgttc cggtcaagtc actgcgatta acgacacgcc ttatgactgt  1695
```

| catatcgaca ggtccctctc cagagccggc ctacacaaca gtgatgctgg cgttcttcta | 1755 |
| ttccaagccc tcaacatcta agtgcagcgg cgaattc | 1792 |

<210> SEQ ID NO 8
<211> LENGTH: 27
<212> TYPE: PRT
<213> ORGANISM: Aspergillus nidulans

<400> SEQUENCE: 8

Met Arg Gly Cys Ile Leu Leu Leu Arg Gly Pro Glu Gly Glu Gln Ala
 1               5                  10                  15

Arg Thr Asp Pro Ala Lys Ile Ser Pro Leu Asp
            20                  25

<210> SEQ ID NO 9
<211> LENGTH: 1792
<212> TYPE: DNA
<213> ORGANISM: Aspergillus nidulans

<400> SEQUENCE: 9

| gaattcgccg ctgcacttag atgttgaggg cttggaatag aagaacgcca gcatcactgt | 60 |
| tgtgtaggcc ggctctggag agggacctgt cgatatgaca gtcataaggc gtgtcgttaa | 120 |
| tcgcagtgac ttgaccggaa caaacccata cggttgggct cattaaatcc tcccccaact | 180 |
| tgcggcttac cggaatcagt gcttgctcag atcagcgcag agattgcatt cgcccggcgg | 240 |
| tttgatatct tcgtgaaacc agcaatggtc gtcatgacgt cgtcgcgtgg ccttatctgg | 300 |
| cttttttgagc aatgctaatt tgaaggcgcg ggctcctctc gtgtcttgcc cttgtcggcc | 360 |
| gtcggttgtg tcgtaccgtc gtccatgtag aggttattct catagatgta ctcaatcacc | 420 |
| gggtcaggga tcaagtagcg tacgctcata tctcgcctga ggaataagcg aatcttagtg | 480 |
| ctgctaacgt cattttgaat aagttgttga ataacatgga tattctttt ccatggctgc | 540 |
| aatgccgcga gcgcctcgtc aatatctgtc ccgcttcgct cgacgatgaa agtctagacc | 600 |
| agttagcttg cgcgaagttt aggatagata caacataaca tacccgtac tgtccaagaa | 660 |
| tatgatcgag atccttctca ctccatactc cgggcgtaga catggtatgg accaaatctg | 720 |
| ccccggccaa taagacgact tgcactcgct ttcgagtgcc ttttccggta tcgataccctt | 780 |
| tgcggacagt gttgatctcg tagtcaaaat gatccagtac gatggcagtt ggctggtact | 840 |
| ccttgtgcat cggctcccat gtatccacca tcatccagtc tgacgtttgg tccacggctc | 900 |
| gttggcacat tgcaattcta aagccgccag atcagtcctg atagtaact atggaagaag | 960 |
| tgtgttaaag taactacctg tgattggcac tcgcaagacc tgccttgcgg taggcgtccg | 1020 |
| agacgggcga agataacct ccaattattt cgaaatctgt gctcagtttg acgtaatcgg | 1080 |
| cggccatttc gaacatgcgc aggtgcagga acgtaatagg tgagaatgaa ccgcaagcta | 1140 |
| taagcaatag cggcgtcttt tccgggtcat ccatcacacg cttcaggcga tattcaggga | 1200 |
| agacgtaatc ctcaacgggg gtcgccgggg cggggggcat tcgctggcca tcgttgccct | 1260 |
| gttcttgagt ggattcggtc atgatcgcgg agatgtgcag cgtgtctgcg cgtagtaact | 1320 |
| gtaaatcaga gcaagagact gaatatttca gtcgagagcg gcatgaagat gaagaaggga | 1380 |
| agatgacagt agcccgaacc aagggcggcg acaaaaggct ggctggctgg atgcgggcaa | 1440 |
| gaatggaagg gttagtcagc cgtgtggggg ggagagcgaa gactcgagag gggaaatttt | 1500 |
| cgccggatca gtgcgggcct gttcccctte tggccctcgg agaaggagaa tacatcccct | 1560 |
| cattccttca ggaccgtacc gttattctcc gtatgcgagg ttgacctatt gccttgggag | 1620 |

-continued

```
ccaaccgtac gaaaatactt tccgtctata ggcactggac cacgtactat atttcttcag    1680
ccgtatcaga agacctattg cggacgcaaa atagaaatca cgtggatcgc tacaaaattt    1740
aatgtactga catcggagca tactccgagg ttctgctcca tcacaggaat tc            1792

<210> SEQ ID NO 10
<211> LENGTH: 1899
<212> TYPE: DNA
<213> ORGANISM: Aspergillus nidulans
<220> FEATURE:
<221> NAME/KEY: CDS
<222> LOCATION: (453)...(627)
<221> NAME/KEY: CDS
<222> LOCATION: (686)...(890)
<221> NAME/KEY: CDS
<222> LOCATION: (949)...(1157)
<221> NAME/KEY: CDS
<222> LOCATION: (1212)...(1288)

<400> SEQUENCE: 10
ttgccttctt agacttgata tctgaaggaa tataacggaa gagatcatct ggtttgatgg      60
tactgtatta gcgggagcac gtgattattt ccctccgata ggccagtggc gtatgtcata    120
aggaagactg acgcctggag gggaaaaacac ctccctcgcc cgagttccat cttatcactt   180
tcacgctcga tctctccaag tttctggctt cattgactga gtcgctcgcc ttgcctagtg    240
ggtagattta gatctagtcg caaatcactt gcctacattc tcgaacctgt ttgttcagcc    300
ttgcggttcc cctcactact tatctcttct taccttctac cgtttcgaaa acacttcctc    360
ctgcggcgag actagtatct atcgcctgtc gcccactttc accaccgtgt ttcactagga    420
gaatagtgaa agactcaagt cgtctaccaa aa atg tgg tca tgg ttc cgg tgg      473
                                    Met Trp Ser Trp Phe Arg Trp
                                     1               5 tgc ggc cgc gca gaa gcg caa gga agc gcc gaa aac gca atc ctc cag      521
Cys Gly Arg Ala Glu Ala Gln Gly Ser Ala Glu Asn Ala Ile Leu Gln
         10                  15                  20 ctt cga agc cac ctt gac atg cta cag aag cga gaa aag cac cta gaa      569
Leu Arg Ser His Leu Asp Met Leu Gln Lys Arg Glu Lys His Leu Glu
 25                  30                  35 aac caa atg aac gaa caa gag gcc atc gct aaa aag aac gtg acc acg      617
Asn Gln Met Asn Glu Gln Glu Ala Ile Ala Lys Lys Asn Val Thr Thr
 40                  45                  50                  55 aat aag aac g gtgtgtatat tatgggaccct ttatacaagt tcccatgctg            667
Asn Lys Asn atttgaccac caccgcag cc gcc aaa gcc gcg ctc cga cgg aaa aag gtg       717
                   Ala Ala Lys Ala Ala Leu Arg Arg Lys Lys Val
                                60                  65 cac gag aag aac tta gaa cag acg cag gct cag att gta cag ctt gag      765
His Glu Lys Asn Leu Glu Gln Thr Gln Ala Gln Ile Val Gln Leu Glu
 70                  75                  80                  85 cag cag ata tac tct att gaa gcc gcc aat att aac cac gag acc ctg      813
Gln Gln Ile Tyr Ser Ile Glu Ala Ala Asn Ile Asn His Glu Thr Leu
             90                  95                 100 gcc gcc atg aag gcc gcc ggt gca gct atg gag aag att cac aac ggc      861
Ala Ala Met Lys Ala Ala Gly Ala Ala Met Glu Lys Ile His Asn Gly
        105                 110                 115 atg acc gtc gaa cag gtc gac gag aca at gtacgtccct tactgtaccg        910
Met Thr Val Glu Gln Val Asp Glu Thr Met
        120                 125 ctggtgacat accggaattg gcatgctaac agactcag g gac aaa ctg cgg gaa    964
                                          Asp Lys Leu Arg Glu
```

```
                                      130
caa caa gcc atc aac gac gaa atc gcg att gcc atc aca aac ccg ggg      1012
Gln Gln Ala Ile Asn Asp Glu Ile Ala Ile Ala Ile Thr Asn Pro Gly
        135                 140                 145 ttc ggc gag cag gtg gac gaa gaa gat ctg gag gcg gaa ctc gag ggc      1060
Phe Gly Glu Gln Val Asp Glu Glu Asp Leu Glu Ala Glu Leu Glu Gly
    150                 155                 160 atg gag cag gag gct atg gac gag cgc atg ctc cac aca ggc aca gta      1108
Met Glu Gln Glu Ala Met Asp Glu Arg Met Leu His Thr Gly Thr Val
165                 170                 175                 180 cca gtt gca gat cag ctc aat cgg cta cct gcg cca gcg aat gca gaa      1156
Pro Val Ala Asp Gln Leu Asn Arg Leu Pro Ala Pro Ala Asn Ala Glu
            185                 190                 195 c gtaaggctct ccctttccca cctcaaaagc gaactccgac tgacagcctt             1207 ccag cc gcc aaa gcg aaa cag aaa gca gaa gaa gaa gac gag gaa gcc      1255
     Pro Ala Lys Ala Lys Gln Lys Ala Glu Glu Glu Asp Glu Glu Ala
                      200                 205                 210 gag ttg gag aag tta cgc gcg gaa atg gcc atg tgagagtggt cctggtgctt    1308
Glu Leu Glu Lys Leu Arg Ala Glu Met Ala Met
                215                 220 tggtctcttt ggtctaactt taatctttt tcttcccct acacatatga tgaacaggga      1368
atcgttatca tgacgcacta cgattagcca agcactgtgt tctttttccg tcggctcgtt   1428
gcgattcctt cttctccgcg gcgtaattac ttatctagtt gtaccaacta ccccgcgagg   1488
cttctgttga ggcgagagcg aaagcccaga cgtgtcgccc ttgccctgat tactggccac   1548
tcccgtccga gcacgctacc tccgttctgt ccacgctgtg tatcccactc tgtaataatc   1608
taccaagtga atacttttct ggatgatttg aagggcctat gtttcctacg ccatcatgtc   1668
attagatatg ttttgtggat catgtttccc cagcgcaatt gatgcccatt tgcagttcac   1728
actcgtgtca tatgaacctc agaatatgaa agccgcttct caacccagca aaacgtcact   1788
gaggattaaa attgagtaat tgagtaaaac taaattagta gctagataac tcccgtttcc   1848
caccagacct aacaccgtcc aaacagataa tcaacaagga aagaaagaa a             1899

<210> SEQ ID NO 11
<211> LENGTH: 59
<212> TYPE: PRT
<213> ORGANISM: Aspergillus nidulans

<400> SEQUENCE: 11

Met Trp Ser Trp Phe Arg Trp Cys Gly Arg Ala Glu Ala Gln Gly Ser
 1               5                  10                  15

Ala Glu Asn Ala Ile Leu Gln Leu Arg Ser His Leu Asp Met Leu Gln
            20                  25                  30

Lys Arg Glu Lys His Leu Glu Asn Gln Met Asn Glu Gln Glu Ala Ile
        35                  40                  45

Ala Lys Lys Asn Val Thr Thr Asn Lys Asn Ala
    50                  55

<210> SEQ ID NO 12
<211> LENGTH: 1899
<212> TYPE: DNA
<213> ORGANISM: Aspergillus nidulans

<400> SEQUENCE: 12
tttctttctt ttccttgttg attatctgtt tggacggtgt taggtctggt gggaaacggg    60
agttatctag ctactaattt agttttactc aattactcaa ttttaatcct cagtgacgtt   120
```

```
ttgctgggtt gagaagcggc tttcatattc tgaggttcat atgacacgag tgtgaactgc    180
aaatgggcat caattgcgct ggggaaacat gatccacaaa acatatctaa tgacatgatg    240
gcgtaggaaa cataggccct tcaaatcatc cagaaaagta ttcacttggt agattattac    300
agagtgggat acacagcgtg gacagaacgg aggtagcgtg ctcggacggg agtggccagt    360
aatcagggca agggcgacac gtctgggctt cgctctcgc ctcaacagaa gcctcgcggg    420
gtagttggta caactagata agtaattacg ccgcggagaa gaaggaatcg caacgagccg    480
acggaaaaag aacacagtgc ttggctaatc gtagtgcgtc atgataacga ttccctgttc    540
atcatatgtg tagggggaag aaaaaagatt aaagttagac caaagagacc aaagcaccag    600
gaccactctc acatggccat ttccgcgcgt aacttctcca actcggcttc ctcgtcttct    660
tcttctgctt tctgtttcgc tttggcggct ggaaggctgt cagtcggagt tcgcttttga    720
ggtgggaaag ggagagcctt acgttctgca ttcgctggcg caggtagccg attgagctga    780
tctgcaactg gtactgtgcc tgtgtggagc atgcgctcgt ccatagcctc ctgctccatg    840
ccctcgagtt ccgcctccag atcttcttcg tccacctgct cgccgaaccc cgggtttgtg    900
atggcaatcg cgatttcgtc gttgatggct tgttgttccc gcagtttgtc cctgagtctg    960
ttagcatgcc aattccggta tgtcaccagc ggtacagtaa gggacgtaca ttgtctcgtc   1020
gacctgttcg acggtcatgc cgttgtgaat cttctccata gctgcaccgg cggccttcat   1080
ggcggccagg gtctcgtggt taatattggc ggcttcaata gagtatatct gctgctcaag   1140
ctgtacaatc tgagcctgcg tctgttctaa gttcttctcg tgcaccttt tccgtcggag   1200
cgcggctttg gcggctgcgg tggtggtcaa atcagcatgg gaacttgtat aaaggtccca   1260
taatatacac accgttctta ttcgtggtca cgttcttttt agcgatggcc tcttgttcgt   1320
tcatttggtt ttctaggtgc ttttctcgct tctgtagcat gtcaaggtgg cttcgaagct   1380
ggaggattgc gtttcggcg cttccttgcg cttctgcgcg gccgcaccac cggaaccatg    1440
accacatttt tggtagacga cttgagtctt tcactattct cctagtgaaa cacggtggtg   1500
aaagtgggcg acaggcgata gatactagtc tcgccgcagg aggaagtgtt ttcgaaacgg   1560
tagaaggtaa gaagagataa gtagtgaggg gaaccgcaag gctgaacaaa caggttcgag   1620
aatgtaggca agtgatttgc gactagatct aaatctaccc actaggcaag gcgagcgact   1680
cagtcaatga agccagaaac ttggagagat cgagcgtgaa agtgataaga tggaactcgg   1740
gcgagggagg tgttttcccc tccaggcgtc agtcttcctt atgacatacg ccactggcct   1800
atcggaggga ataatcacg tgctcccgct aatacagtac catcaaacca gatgatctct   1860
tccgttatat tccttcagat atcaagtcta agaaggcaa                         1899
```

<210> SEQ ID NO 13
<211> LENGTH: 3800
<212> TYPE: DNA
<213> ORGANISM: Saccharomyces cerevisiae
<220> FEATURE:
<221> NAME/KEY: CDS
<222> LOCATION: (306)...(3458)

<400> SEQUENCE: 13

```
tttttcttgt cagtctgaaa atttttcatt tggtttttg aaaaaaatcc tgcctaatat     60
ggtatcaaga ggaataacaa gaaaaaaaaa tcatggggga tacaaaggaa acaaggaga    120
taatgcaggt tatactgaat tgctcatagt attagcctaa agcactttac ctctgattta   180
ttgcatctat cgtattcttg agttattgcg acttttaaaa tccgtgcacc gcatatgaaa   240
```

```
gggtagagcc ttcgtgtttg tttacctttt tagctctttg aagatcaaac aaaaacactt        300 cagta atg cct aca gcc ttg gat aag aca aag aag tta aca gcc gcg ccc        350
      Met Pro Thr Ala Leu Asp Lys Thr Lys Lys Leu Thr Ala Ala Pro
       1               5                  10                  15 atc atg caa gat cct gat ggt att gac att aat acg aaa atc ttt aac          398
Ile Met Gln Asp Pro Asp Gly Ile Asp Ile Asn Thr Lys Ile Phe Asn
             20                  25                  30 tca gtt gct gaa gta ttt caa aag gca cag ggt tct tat gca gga cac          446
Ser Val Ala Glu Val Phe Gln Lys Ala Gln Gly Ser Tyr Ala Gly His
             35                  40                  45 agg aag cat ata gca gtt ttg aag aaa att cag tca aag gct gtt gag          494
Arg Lys His Ile Ala Val Leu Lys Lys Ile Gln Ser Lys Ala Val Glu
         50                  55                  60 caa ggc tat gaa gat gct ttt aac ttt tgg ttc gat aaa tta gtt act          542
Gln Gly Tyr Glu Asp Ala Phe Asn Phe Trp Phe Asp Lys Leu Val Thr
         65                  70                  75 aag atc ctt cct ctg aaa aag aat gag att atc gga gac agg ata gta          590
Lys Ile Leu Pro Leu Lys Lys Asn Glu Ile Ile Gly Asp Arg Ile Val
 80                  85                  90                  95 aag tta gta gct gca ttt ata gct tct tta gaa agg gag ttg ata ttg          638
Lys Leu Val Ala Ala Phe Ile Ala Ser Leu Glu Arg Glu Leu Ile Leu
                100                 105                 110 gcc aaa aaa caa aac tat aag ctc acg aat gat gaa gaa ggg ata ttc          686
Ala Lys Lys Gln Asn Tyr Lys Leu Thr Asn Asp Glu Glu Gly Ile Phe
             115                 120                 125 tca agg ttc gtc gat cag ttc ata aga cat gtt ttg cgt ggt gtg gaa          734
Ser Arg Phe Val Asp Gln Phe Ile Arg His Val Leu Arg Gly Val Glu
             130                 135                 140 agc cct gac aag aac gtc aga ttt aga gtt tta cag tta tta gcc gtt          782
Ser Pro Asp Lys Asn Val Arg Phe Arg Val Leu Gln Leu Leu Ala Val
         145                 150                 155 ata atg gat aat ata ggg gaa atc gat gaa tca ctt ttc aat tta tta          830
Ile Met Asp Asn Ile Gly Glu Ile Asp Glu Ser Leu Phe Asn Leu Leu
160                 165                 170                 175 ata ttg tct tta aat aag agg att tat gat aga gaa cca acg gtt agg          878
Ile Leu Ser Leu Asn Lys Arg Ile Tyr Asp Arg Glu Pro Thr Val Arg
                180                 185                 190 ata cag gct gtg ttt tgt tta act aaa ttt cag gat gaa gag caa act          926
Ile Gln Ala Val Phe Cys Leu Thr Lys Phe Gln Asp Glu Glu Gln Thr
             195                 200                 205 gaa cat tta act gag ctt tct gat aat gaa gaa aat ttt gaa gct acg          974
Glu His Leu Thr Glu Leu Ser Asp Asn Glu Glu Asn Phe Glu Ala Thr
             210                 215                 220 aga act cta gtt gct tct atc cag aac gat ccg tca gct gaa gta cgg         1022
Arg Thr Leu Val Ala Ser Ile Gln Asn Asp Pro Ser Ala Glu Val Arg
         225                 230                 235 agg gct gca atg ctg aat ttg atc aat gat aat aat act aga ccg tat         1070
Arg Ala Ala Met Leu Asn Leu Ile Asn Asp Asn Asn Thr Arg Pro Tyr
240                 245                 250                 255 atc ttg gag agg gct aga gat gta aac atc gtt aat aga agg ctc gtg         1118
Ile Leu Glu Arg Ala Arg Asp Val Asn Ile Val Asn Arg Arg Leu Val
                260                 265                 270 tat tcg aga att ttg aaa tca atg gga aga aag tgt ttc gat gat att         1166
Tyr Ser Arg Ile Leu Lys Ser Met Gly Arg Lys Cys Phe Asp Asp Ile
             275                 280                 285 gag ccg cat att ttt gat caa ttg att gag tgg ggt tta gaa gat agg         1214
Glu Pro His Ile Phe Asp Gln Leu Ile Glu Trp Gly Leu Glu Asp Arg
             290                 295                 300
```

| | | | | | | | | | | | | | | |
|---|---|---|---|---|---|---|---|---|---|---|---|---|---|---|
| gaa | tta | tca | gtg | aga | aat | gcg | tgt | aag | aga | ctc | att | gct | cat | gat tgg | 1262 |
| Glu | Leu | Ser | Val | Arg | Asn | Ala | Cys | Lys | Arg | Leu | Ile | Ala | His | Asp Trp |
| | 305 | | | | 310 | | | | | 315 | | | | |

```
gaa tta tca gtg aga aat gcg tgt aag aga ctc att gct cat gat tgg    1262
Glu Leu Ser Val Arg Asn Ala Cys Lys Arg Leu Ile Ala His Asp Trp
    305             310             315 tta aat gct ctg gat ggc gat ttg ata gaa tta cta gaa aaa ttg gat    1310
Leu Asn Ala Leu Asp Gly Asp Leu Ile Glu Leu Leu Glu Lys Leu Asp
320             325             330             335 gtc tca aga tcc tca gtg tgt gtt aag gct ata gaa gca ctt ttt caa    1358
Val Ser Arg Ser Ser Val Cys Val Lys Ala Ile Glu Ala Leu Phe Gln
            340             345             350 tca agg cca gat ata tta tct aaa atc aaa ttt cct gaa agt att tgg    1406
Ser Arg Pro Asp Ile Leu Ser Lys Ile Lys Phe Pro Glu Ser Ile Trp
        355             360             365 aaa gac ttt acc gta gaa att gcc ttc ctc ttt cgg gct att tat ttg    1454
Lys Asp Phe Thr Val Glu Ile Ala Phe Leu Phe Arg Ala Ile Tyr Leu
370             375             380 tac tgt ttg gat aat aat ata aca gaa atg ctg gaa gaa aac ttt cca    1502
Tyr Cys Leu Asp Asn Asn Ile Thr Glu Met Leu Glu Glu Asn Phe Pro
    385             390             395 gaa gcc tca aaa tta tcc gag cat tta aac cat tat att ctt ctc aga    1550
Glu Ala Ser Lys Leu Ser Glu His Leu Asn His Tyr Ile Leu Leu Arg
400             405             410             415 tat cat cac aac gac att tct aat gac tct cag tcg cat ttt gat tat    1598
Tyr His His Asn Asp Ile Ser Asn Asp Ser Gln Ser His Phe Asp Tyr
            420             425             430 aac act tta gag ttt att att gag caa cta tcg att gcc gcc gaa agg    1646
Asn Thr Leu Glu Phe Ile Ile Glu Gln Leu Ser Ile Ala Ala Glu Arg
        435             440             445 tat gat tat agc gat gag gtt gga agg aga tcg atg ctt aca gtg gta    1694
Tyr Asp Tyr Ser Asp Glu Val Gly Arg Arg Ser Met Leu Thr Val Val
    450             455             460 cga aat atg ctg gcc tta act aca ctc tcc gaa cct ctt att aaa att    1742
Arg Asn Met Leu Ala Leu Thr Thr Leu Ser Glu Pro Leu Ile Lys Ile
465             470             475 ggt att cgt gta atg aaa agt ctg tcc ata aat gaa aaa gat ttt gta    1790
Gly Ile Arg Val Met Lys Ser Leu Ser Ile Asn Glu Lys Asp Phe Val
480             485             490             495 aca atg gca ata gaa atc att aat gat att aga gac gac gat att gaa    1838
Thr Met Ala Ile Glu Ile Ile Asn Asp Ile Arg Asp Asp Asp Ile Glu
            500             505             510 aaa caa gaa caa gaa gag aaa ata aaa agc aag aag att aat cgc aga    1886
Lys Gln Glu Gln Glu Glu Lys Ile Lys Ser Lys Lys Ile Asn Arg Arg
        515             520             525 aat gag act tcc gtc gat gaa gag gac gaa aac ggc aca cat aat gac    1934
Asn Glu Thr Ser Val Asp Glu Glu Asp Glu Asn Gly Thr His Asn Asp
    530             535             540 gaa gtt aac gag gat gaa gaa gac gac aat att tca tcc ttc cat tct    1982
Glu Val Asn Glu Asp Glu Glu Asp Asp Asn Ile Ser Ser Phe His Ser
545             550             555 gct gta gaa aac tta gtg cag gga aac ggc aac gta tct gag agt gac    2030
Ala Val Glu Asn Leu Val Gln Gly Asn Gly Asn Val Ser Glu Ser Asp
560             565             570             575 ata ata aat aat ctc cca ccc gaa aag gaa gcg tcc tca gca aca att    2078
Ile Ile Asn Asn Leu Pro Pro Glu Lys Glu Ala Ser Ser Ala Thr Ile
            580             585             590 gtt ctc tgt ctt aca agg tca tca tat atg cta gaa cta gtt aac aca    2126
Val Leu Cys Leu Thr Arg Ser Ser Tyr Met Leu Glu Leu Val Asn Thr
        595             600             605 ccg tta aca gaa aac att tta att gcg tcg ttg atg gac act ttg atc    2174
Pro Leu Thr Glu Asn Ile Leu Ile Ala Ser Leu Met Asp Thr Leu Ile
    610             615             620
```

```
aca cca gcg gtt aga aat acc gcg cca aat att agg gag ctt ggt gtc    2222
Thr Pro Ala Val Arg Asn Thr Ala Pro Asn Ile Arg Glu Leu Gly Val
    625                 630                 635 aag aac ctt ggt tta tgt tgt ctc ttg gat gtg aag ttg gct att gat    2270
Lys Asn Leu Gly Leu Cys Cys Leu Leu Asp Val Lys Leu Ala Ile Asp
640                 645                 650                 655 aac atg tac atc tta ggt atg tgc gtt tcg aaa ggt aat gca tca tta    2318
Asn Met Tyr Ile Leu Gly Met Cys Val Ser Lys Gly Asn Ala Ser Leu
                660                 665                 670 aag tat att gcg tta caa gtc att gta gat att ttt tcc gta cat ggg    2366
Lys Tyr Ile Ala Leu Gln Val Ile Val Asp Ile Phe Ser Val His Gly
            675                 680                 685 aac act gtg gta gac gga gaa ggc aaa gtt gac tca atc tcg ttg cac    2414
Asn Thr Val Val Asp Gly Glu Gly Lys Val Asp Ser Ile Ser Leu His
        690                 695                 700 aaa ata ttt tac aag gtt tta aag aat aac ggt tta ccg gaa tgt cag    2462
Lys Ile Phe Tyr Lys Val Leu Lys Asn Asn Gly Leu Pro Glu Cys Gln
    705                 710                 715 gtg ata gca gcg gag ggt tta tgc aaa cta ttt ttg gca gac gtg ttc    2510
Val Ile Ala Ala Glu Gly Leu Cys Lys Leu Phe Leu Ala Asp Val Phe
720                 725                 730                 735 act gat gat gat ttg ttt gaa acg ttg gtt ttg tca tat ttt tcg ccg    2558
Thr Asp Asp Asp Leu Phe Glu Thr Leu Val Leu Ser Tyr Phe Ser Pro
                740                 745                 750 ata aat tcc tca aac gaa gcg ctg gta cag gca ttt gcc ttc tgc att    2606
Ile Asn Ser Ser Asn Glu Ala Leu Val Gln Ala Phe Ala Phe Cys Ile
            755                 760                 765 cca gtc tat tgt ttt tca cat cct gct cat caa caa cgt atg tct agg    2654
Pro Val Tyr Cys Phe Ser His Pro Ala His Gln Gln Arg Met Ser Arg
        770                 775                 780 acg gct gcg gac ata ctc tta aga cta tgt gtt ctt tgg gac gat tta    2702
Thr Ala Ala Asp Ile Leu Leu Arg Leu Cys Val Leu Trp Asp Asp Leu
    785                 790                 795 cag agc tct gta ata cct gag gta gac cgt gaa gct atg cta aag cct    2750
Gln Ser Ser Val Ile Pro Glu Val Asp Arg Glu Ala Met Leu Lys Pro
800                 805                 810                 815 aac ata ata ttt caa cag ttg cta ttt tgg act gat cca cgt aac tta    2798
Asn Ile Ile Phe Gln Gln Leu Leu Phe Trp Thr Asp Pro Arg Asn Leu
                820                 825                 830 gtt aac cag aca ggt tca aca aaa aaa gat aca gtg cag ctt aca ttc    2846
Val Asn Gln Thr Gly Ser Thr Lys Lys Asp Thr Val Gln Leu Thr Phe
            835                 840                 845 ttg atc gat gtg ctc aaa ata tac gct caa att gag aag aaa gaa ata    2894
Leu Ile Asp Val Leu Lys Ile Tyr Ala Gln Ile Glu Lys Lys Glu Ile
        850                 855                 860 aag aag atg atc atc act aat ata aac gct ata ttt ctt tct tct gaa    2942
Lys Lys Met Ile Ile Thr Asn Ile Asn Ala Ile Phe Leu Ser Ser Glu
    865                 870                 875 caa gat tat tct act ttg aaa gaa ctt ctt gag tat tct gac gat att    2990
Gln Asp Tyr Ser Thr Leu Lys Glu Leu Leu Glu Tyr Ser Asp Asp Ile
880                 885                 890                 895 gca gaa aat gat aat tta gac aat gtt agc aaa aat gct ctg gac aag    3038
Ala Glu Asn Asp Asn Leu Asp Asn Val Ser Lys Asn Ala Leu Asp Lys
                900                 905                 910 cta agg aat aat ttg aat tcg ctg att gaa gag atc aat gaa agg tca    3086
Leu Arg Asn Asn Leu Asn Ser Leu Ile Glu Glu Ile Asn Glu Arg Ser
            915                 920                 925 gaa act cag aca aaa gat gag aac aac act gcg aat gac caa tac tcg    3134
Glu Thr Gln Thr Lys Asp Glu Asn Asn Thr Ala Asn Asp Gln Tyr Ser
```

```
                930             935             940
tct att ttg ggg aat tca ttc aat aaa tct tca aat gac acc ata gaa    3182
Ser Ile Leu Gly Asn Ser Phe Asn Lys Ser Ser Asn Asp Thr Ile Glu
        945             950             955 cac gct gct gat ata act gat gga aat aac aca gaa ttg act aaa aca    3230
His Ala Ala Asp Ile Thr Asp Gly Asn Asn Thr Glu Leu Thr Lys Thr
960             965             970             975 act gtt aat att tcg gca gtt gac aat aca aca gag caa agt aac tca    3278
Thr Val Asn Ile Ser Ala Val Asp Asn Thr Thr Glu Gln Ser Asn Ser
                980             985             990 agg aaa aga acg aga tca gaa gcg gag caa att gac aca tcc aaa aac    3326
Arg Lys Arg Thr Arg Ser Glu Ala Glu Gln Ile Asp Thr Ser Lys Asn
            995             1000            1005 ctg gaa aac atg agt att caa gac acg tca act gta gca aaa aat gta    3374
Leu Glu Asn Met Ser Ile Gln Asp Thr Ser Thr Val Ala Lys Asn Val
        1010            1015            1020 agt ttt gtt tta cct gac gag aaa tca gat gca atg tcc ata gat gaa    3422
Ser Phe Val Leu Pro Asp Glu Lys Ser Asp Ala Met Ser Ile Asp Glu
    1025            1030            1035 gaa gat aag gat tca gag tct ttc agc gag gtc tgt taaaattgat         3468
Glu Asp Lys Asp Ser Glu Ser Phe Ser Glu Val Cys
1040            1045            1050 atgcgagctc ttcatctatt taagttgatt ttttggttgt aaacatattt gtattttatt  3528
cttaggtttg ttaattcttc tacgcttacc agatatagat gctatatgtt attgcattac  3588
gcacattacc cggtgggaca aattatgaaa atattccaag gctataaatt ctttggtgaa  3648
aggaactgaa attatgtcca gtaatgcacc agaaatggac atataaaact attaatgcat  3708
tttattacaa ttatcctaag aaaatatcct atatataatt aaagtaaaag aataagatc   3768 aaaagaacaa aataaagtcg agtagaattt tc                                3800

<210> SEQ ID NO 14
<211> LENGTH: 1051
<212> TYPE: PRT
<213> ORGANISM: Saccharomyces cerevisiae

<400> SEQUENCE: 14

Met Pro Thr Ala Leu Asp Lys Thr Lys Lys Leu Thr Ala Ala Pro Ile
1               5                   10                  15

Met Gln Asp Pro Asp Gly Ile Asp Ile Asn Thr Lys Ile Phe Asn Ser
                20                  25                  30

Val Ala Glu Val Phe Gln Lys Ala Gln Gly Ser Tyr Ala Gly His Arg
            35                  40                  45

Lys His Ile Ala Val Leu Lys Lys Ile Gln Ser Lys Ala Val Glu Gln
        50                  55                  60

Gly Tyr Glu Asp Ala Phe Asn Phe Trp Phe Asp Lys Leu Val Thr Lys
65                  70                  75                  80

Ile Leu Pro Leu Lys Lys Asn Glu Ile Ile Gly Asp Arg Ile Val Lys
                85                  90                  95

Leu Val Ala Ala Phe Ile Ala Ser Leu Glu Arg Glu Leu Ile Leu Ala
            100                 105                 110

Lys Lys Gln Asn Tyr Lys Leu Thr Asn Asp Glu Glu Gly Ile Phe Ser
        115                 120                 125

Arg Phe Val Asp Gln Phe Ile Arg His Val Leu Arg Gly Val Glu Ser
    130                 135                 140

Pro Asp Lys Asn Val Arg Phe Arg Val Leu Gln Leu Leu Ala Val Ile
145                 150                 155                 160
```

```
Met Asn Ile Gly Glu Ile Asp Glu Ser Leu Phe Asn Leu Leu Ile
            165                 170                 175

Leu Ser Leu Asn Lys Arg Ile Tyr Asp Arg Glu Pro Thr Val Arg Ile
            180                 185                 190

Gln Ala Val Phe Cys Leu Thr Lys Phe Gln Asp Glu Glu Gln Thr Glu
            195                 200                 205

His Leu Thr Glu Leu Ser Asp Asn Glu Glu Asn Phe Glu Ala Thr Arg
            210                 215                 220

Thr Leu Val Ala Ser Ile Gln Asn Asp Pro Ser Ala Glu Val Arg Arg
225                 230                 235                 240

Ala Ala Met Leu Asn Leu Ile Asn Asp Asn Thr Arg Pro Tyr Ile
            245                 250                 255

Leu Glu Arg Ala Arg Asp Val Asn Ile Val Asn Arg Arg Leu Val Tyr
            260                 265                 270

Ser Arg Ile Leu Lys Ser Met Gly Arg Lys Cys Phe Asp Asp Ile Glu
            275                 280                 285

Pro His Ile Phe Asp Gln Leu Ile Glu Trp Gly Leu Glu Asp Arg Glu
            290                 295                 300

Leu Ser Val Arg Asn Ala Cys Lys Arg Leu Ile Ala His Asp Trp Leu
305                 310                 315                 320

Asn Ala Leu Asp Gly Asp Leu Ile Glu Leu Leu Glu Lys Leu Asp Val
            325                 330                 335

Ser Arg Ser Ser Val Cys Val Lys Ala Ile Glu Ala Leu Phe Gln Ser
            340                 345                 350

Arg Pro Asp Ile Leu Ser Lys Ile Lys Phe Pro Glu Ser Ile Trp Lys
            355                 360                 365

Asp Phe Thr Val Glu Ile Ala Phe Leu Phe Arg Ala Ile Tyr Leu Tyr
            370                 375                 380

Cys Leu Asp Asn Asn Ile Thr Glu Met Leu Glu Glu Asn Phe Pro Glu
385                 390                 395                 400

Ala Ser Lys Leu Ser Glu His Leu Asn His Tyr Ile Leu Leu Arg Tyr
            405                 410                 415

His His Asn Asp Ile Ser Asn Asp Ser Gln Ser His Phe Asp Tyr Asn
            420                 425                 430

Thr Leu Glu Phe Ile Ile Glu Gln Leu Ser Ile Ala Ala Glu Arg Tyr
            435                 440                 445

Asp Tyr Ser Asp Glu Val Gly Arg Arg Ser Met Leu Thr Val Val Arg
            450                 455                 460

Asn Met Leu Ala Leu Thr Thr Leu Ser Glu Pro Leu Ile Lys Ile Gly
465                 470                 475                 480

Ile Arg Val Met Lys Ser Leu Ser Ile Asn Glu Lys Asp Phe Val Thr
            485                 490                 495

Met Ala Ile Glu Ile Ile Asn Asp Ile Arg Asp Asp Ile Glu Lys
            500                 505                 510

Gln Glu Gln Glu Glu Lys Ile Lys Ser Lys Lys Ile Asn Arg Arg Asn
            515                 520                 525

Glu Thr Ser Val Asp Glu Glu Asp Glu Asn Gly Thr His Asn Asp Glu
            530                 535                 540

Val Asn Glu Asp Glu Glu Asp Asp Asn Ile Ser Ser Phe His Ser Ala
545                 550                 555                 560

Val Glu Asn Leu Val Gln Gly Asn Gly Asn Val Ser Glu Ser Asp Ile
            565                 570                 575
```

-continued

```
Ile Asn Asn Leu Pro Pro Glu Lys Glu Ala Ser Ser Ala Thr Ile Val
            580                 585                 590
Leu Cys Leu Thr Arg Ser Ser Tyr Met Leu Glu Leu Val Asn Thr Pro
        595                 600                 605
Leu Thr Glu Asn Ile Leu Ile Ala Ser Leu Met Asp Thr Leu Ile Thr
    610                 615                 620
Pro Ala Val Arg Asn Thr Ala Pro Asn Ile Arg Glu Leu Gly Val Lys
625                 630                 635                 640
Asn Leu Gly Leu Cys Cys Leu Leu Asp Val Lys Leu Ala Ile Asp Asn
                645                 650                 655
Met Tyr Ile Leu Gly Met Cys Val Ser Lys Gly Asn Ala Ser Leu Lys
            660                 665                 670
Tyr Ile Ala Leu Gln Val Ile Val Asp Ile Phe Ser Val His Gly Asn
        675                 680                 685
Thr Val Val Asp Gly Glu Gly Lys Val Asp Ser Ile Ser Leu His Lys
    690                 695                 700
Ile Phe Tyr Lys Val Leu Lys Asn Asn Gly Leu Pro Glu Cys Gln Val
705                 710                 715                 720
Ile Ala Ala Glu Gly Leu Cys Lys Leu Phe Leu Ala Asp Val Phe Thr
                725                 730                 735
Asp Asp Asp Leu Phe Glu Thr Leu Val Leu Ser Tyr Phe Ser Pro Ile
            740                 745                 750
Asn Ser Ser Asn Glu Ala Leu Val Gln Ala Phe Ala Phe Cys Ile Pro
        755                 760                 765
Val Tyr Cys Phe Ser His Pro Ala His Gln Arg Met Ser Arg Thr
    770                 775                 780
Ala Ala Asp Ile Leu Leu Arg Leu Cys Val Leu Trp Asp Asp Leu Gln
785                 790                 795                 800
Ser Ser Val Ile Pro Glu Val Asp Arg Glu Ala Met Leu Lys Pro Asn
                805                 810                 815
Ile Ile Phe Gln Gln Leu Leu Phe Trp Thr Asp Pro Arg Asn Leu Val
            820                 825                 830
Asn Gln Thr Gly Ser Thr Lys Lys Asp Thr Val Gln Leu Thr Phe Leu
        835                 840                 845
Ile Asp Val Leu Lys Ile Tyr Ala Gln Ile Glu Lys Lys Glu Ile Lys
    850                 855                 860
Lys Met Ile Ile Thr Asn Ile Asn Ala Ile Phe Leu Ser Ser Glu Gln
865                 870                 875                 880
Asp Tyr Ser Thr Leu Lys Glu Leu Leu Glu Tyr Ser Asp Asp Ile Ala
                885                 890                 895
Glu Asn Asp Asn Leu Asp Asn Val Ser Lys Asn Ala Leu Asp Lys Leu
            900                 905                 910
Arg Asn Asn Leu Asn Ser Leu Ile Glu Glu Ile Asn Glu Arg Ser Glu
        915                 920                 925
Thr Gln Thr Lys Asp Glu Asn Asn Thr Ala Asn Asp Gln Tyr Ser Ser
    930                 935                 940
Ile Leu Gly Asn Ser Phe Asn Lys Ser Ser Asn Asp Thr Ile Glu His
945                 950                 955                 960
Ala Ala Asp Ile Thr Asp Gly Asn Asn Thr Glu Leu Thr Lys Thr Thr
                965                 970                 975
Val Asn Ile Ser Ala Val Asp Thr Thr Glu Gln Ser Asn Ser Arg
            980                 985                 990
Lys Arg Thr Arg Ser Glu Ala Glu Gln Ile Asp Thr Ser Lys Asn Leu
```

```
                995                 1000                1005
        Glu Asn Met Ser Ile Gln Asp Thr Ser Thr Val Ala Lys Asn Val Ser
            1010                1015                1020

Phe Val Leu Pro Asp Glu Lys Ser Asp Ala Met Ser Ile Asp Glu Glu
        1025                1030                1035                1040

Asp Lys Asp Ser Glu Ser Phe Ser Glu Val Cys
                    1045                1050

<210> SEQ ID NO 15
<211> LENGTH: 3800
<212> TYPE: DNA
<213> ORGANISM: Saccharomyces cerevisiae

<400> SEQUENCE: 15
```

| | | | | | |
|---|---|---|---|---|---|
| gaaaattcta | ctcgacttta | ttttgttctt | ttgatcttat | ttcttttact | ttaattatat | 60 |
| ataggatatt | ttcttaggat | aattgtaata | aaatgcatta | atagttttat | atgtccattt | 120 |
| ctggtgcatt | actggacata | atttcagttc | ctttcaccaa | agaatttata | gccttggaat | 180 |
| atttccataa | tttgtcccac | cgggtaatgt | gcgtaatgca | ataacatata | gcatctatat | 240 |
| ctggtaagcg | tagaagaatt | aacaaaccta | agaataaaat | acaaatatgt | ttacaaccaa | 300 |
| aaaatcaact | taaatagatg | aagagctcgc | atatcaattt | taacagacct | cgctgaaaga | 360 |
| ctctgaatcc | ttatcttctt | catctatgga | cattgcatct | gatttctcgt | caggtaaaac | 420 |
| aaaacttaca | ttttttgcta | cagttgacgt | gtcttgaata | ctcatgtttt | ccaggttttt | 480 |
| ggatgtgtca | atttgctccg | cttctgatct | cgttcttttc | cttgagttac | tttgctctgt | 540 |
| tgtattgtca | actgccgaaa | tattaacagt | tgttttagtc | aattctgtgt | tatttccatc | 600 |
| agttatatca | gcagcgtgtt | ctatggtgtc | atttgaagat | ttattgaatg | aattccccaa | 660 |
| aatagacgag | tattggtcat | tcgcagtgtt | gttctcatct | tttgtctgag | tttctgacct | 720 |
| ttcattgatc | tcttcaatca | gcgaattcaa | attattcctt | agcttgtcca | gagcattttt | 780 |
| gctaacattg | tctaaattat | cattttctgc | aatatcgtca | gaatactcaa | gaagttcttt | 840 |
| caaagtagaa | taatcttgtt | cagaagaaag | aaatatagcg | tttatattag | tgatgatcat | 900 |
| cttctttatt | tctttcttct | caatttgagc | gtatattttg | agcacatcga | tcaagaatgt | 960 |
| aagctgcact | gtatcttttt | ttgttgaacc | tgtctggtta | actaagttac | gtggatcagt | 1020 |
| ccaaaatagc | aactgttgaa | atattatgtt | aggctttagc | atagcttcac | ggtctaccto | 1080 |
| aggtattaca | gagctctgta | aatcgtccca | agaacacat | agtcttaaga | gtatgtccgc | 1140 |
| agccgtccta | gacatacgtt | gttgatgagc | aggatgtgaa | aaacaataga | ctggaatgca | 1200 |
| gaaggcaaat | gcctgtacca | gcgcttcgtt | tgaggaattt | atcggcgaaa | aatatgacaa | 1260 |
| aaccaacgtt | tcaaacaaat | catcatcagt | gaacacgtct | gccaaaaata | gtttgcataa | 1320 |
| accctccgct | gctatcacct | gacattccgg | taaaccgtta | ttctttaaaa | ccttgtaaaa | 1380 |
| tattttgtgc | aacgagattg | agtcaacttt | gccttctccg | tctaccacag | tgttcccatg | 1440 |
| tacggaaaaa | atatctacaa | tgacttgtaa | cgcaatatac | tttaatgatg | cattaccttt | 1500 |
| cgaaacgcac | atacctaaga | tgtacatgtt | atcaatagcc | aacttcacat | ccaagagaca | 1560 |
| acataaacca | aggttcttga | caccaagctc | cctaatattt | ggcgcggtat | ttctaaccgc | 1620 |
| tggtgtgatc | aaagtgtcca | tcaacgacgc | aattaaaatg | ttttctgtta | acggtgtgtt | 1680 |
| aactagttct | agcatatatg | atgaccttgt | aagacagaga | acaattgttg | ctgaggacgc | 1740 |
| ttcctttcg | ggtgggagat | tatttattat | gtcactctca | gatacgttgc | cgtttccctg | 1800 |

-continued

```
cactaagttt tctacagcag aatggaagga tgaaatattg tcgtcttctt catcctcgtt    1860
aacttcgtca ttatgtgtgc cgttttcgtc ctcttcatcg acggaagtct catttctgcg    1920
attaatcttc ttgcttttta ttttctcttc ttgttcttgt ttttcaatat cgtcgtctct    1980
aatatcatta atgatttcta ttgccattgt tacaaaatct ttttcattta tggacagact    2040
tttcattaca cgaataccaa ttttaataag aggttcggag agtgtagtta aggccagcat    2100
atttcgtacc actgtaagca tcgatctcct tccaacctca tcgctataat catacctttc    2160
ggcggcaatc gatagttgct caataataaa ctctaaagtg ttataatcaa aatgcgactg    2220
agagtcatta gaaatgtcgt tgtgatgata tctgagaaga atataatggt ttaaatgctc    2280
ggataatttt gaggcttctg gaagttttc ttccagcatt tctgttatat tattatccaa     2340
acagtacaaa taaatagccc gaaagaggaa ggcaatttct acggtaaagt ctttccaaat    2400
actttcagga aatttgattt tagataatat atctggcctt gattgaaaaa gtgcttctat    2460
agccttaaca cacactgagg atcttgagac atccaatttt tctagtaatt ctatcaaatc    2520
gccatccaga gcatttaacc aatcatgagc aatgagtctc ttacacgcat ttctcactga    2580
taattcccta tcttctaaac cccactcaat caattgatca aaaatatgcg gctcaatatc    2640
atcgaaacac tttcttccca ttgatttcaa aattctcgaa tacacgagcc ttctattaac    2700
gatgtttaca tctctagccc tctccaagat atacggtcta gtattattat cattgatcaa    2760
attcagcatt gcagccctcc gtacttcagc tgacggatcg ttctggatag aagcaactag    2820
agttctcgta gcttcaaaat tttcttcatt atcagaaagc tcagttaaat gttcagtttg    2880
ctcttcatcc tgaaatttag ttaaacaaaa cacagcctgt atcctaaccg ttggttctct    2940
atcataaatc ctcttattta aagacaatat taataaattg aaaagtgatt catcgatttc    3000
ccctatatta tccattataa cggctaataa ctgtaaaact ctaaatctga cgttcttgtc    3060
agggctttcc acaccacgca aaacatgtct tatgaactga tcgacgaacc ttgagaatat    3120
cccttcttca tcattcgtga gcttatagtt ttgttttttg gccaatatca actcccttc     3180 taaagaagct ataaatgcag ctactaactt tactatcctg tctccgataa tctcattctt    3240
tttcagagga aggatcttag taactaattt atcgaaccaa agttaaaag catcttcata     3300 gccttgctca acagcctttg actgaatttt cttcaaaact gctatatgct tcctgtgtcc    3360
tgcataagaa ccctgtgcct tttgaaatac ttcagcaact gagttaaaga ttttcgtatt    3420
aatgtcaata ccatcaggat cttgcatgat gggcgcggct gttaacttct ttgtcttatc    3480
caaggctgta ggcattactg aagtgttttt gtttgatctt caaagagcta aaaggtaaa    3540 caaacacgaa ggctctaccc tttcatatgc ggtgcacgga ttttaaaagt cgcaataact    3600
caagaatacg atagatgcaa taaatcagag gtaaagtgct ttaggctaat actatgagca    3660
attcagtata acctgcatta tctccttgtt tccttgta tccccatga ttttttttc        3720 ttgttattcc tcttgatacc atattaggca ggatttttt caaaaaacca aatgaaaaat    3780
tttcagactg acaagaaaaa                                                3800
```

<210> SEQ ID NO 16
<211> LENGTH: 2156
<212> TYPE: DNA
<213> ORGANISM: Saccharomyces cerevisiae
<220> FEATURE:
<221> NAME/KEY: CDS
<222> LOCATION: (543)...(1727)

<400> SEQUENCE: 16

-continued

```
tcttttggtg tcaatggtgt attattccga gttactccag gctaggttca ggagtaccaa      60
gaatgtactt tatttattta tacaccggag caagtcatat aattacgcaa acgattcgaa     120
attgttaaaa gcaggatcaa cgtatctcat ttcttttga aagacgggta atagaaagtc      180
tctgagtcgc accccacatg gatatcgtac tattcgtata tggaatgtaa aatactcgca     240
atacgatttt atttagcttc acaatctctc aaacttatcg tcttgatcaa tctttacgtt     300
ttaccaaata atcgcctgtt tctggccatt ttttgcttat accatctacc atactcgctg     360
tccatatgtg acggtgtcgt ctccaagaaa ataacaatg taaattgacc cagcgtgacg      420
acagtagact gtaagttata gtacaatcat actctacctt agtcactgtt cctccactgt     480
taagtagaga gagagagaga gtttaaagtg gagaaggcaa gaaaaagtgc acttattacg     540
```

| | | | | | | | | | | | | | | | | |
|---|---|---|---|---|---|---|---|---|---|---|---|---|---|---|---|---|
| ta atg gat ccc acc aaa gca ccc gat ttt aaa ccg cca cag cca aat | | | | | | | | | | | | | | | | 587 |
| Met Asp Pro Thr Lys Ala Pro Asp Phe Lys Pro Pro Gln Pro Asn | | | | | | | | | | | | | | | | |
| 1 | | | 5 | | | | | 10 | | | | | 15 | | | |

```
gaa gaa cta caa cca ccg cca gat cca aca cat acg ata cca aaa tct     635
Glu Glu Leu Gln Pro Pro Pro Asp Pro Thr His Thr Ile Pro Lys Ser
            20                  25                  30 gga ccc ata gtt cca tat gtt tta gct gat tat aat tct tcg atc gat     683
Gly Pro Ile Val Pro Tyr Val Leu Ala Asp Tyr Asn Ser Ser Ile Asp
        35                  40                  45 gct cct ttc aat ctc gac att tac aaa acc ctg tcg tca agg aaa aaa     731
Ala Pro Phe Asn Leu Asp Ile Tyr Lys Thr Leu Ser Ser Arg Lys Lys
    50                  55                  60 aac gcc aac tca agc aac cga atg gac cat att cca tta aat act agt     779
Asn Ala Asn Ser Ser Asn Arg Met Asp His Ile Pro Leu Asn Thr Ser
65                  70                  75 gac ttc cag cca cta tct cgg gat gta tca tcg gag gag gaa agt gaa     827
Asp Phe Gln Pro Leu Ser Arg Asp Val Ser Ser Glu Glu Glu Ser Glu
80                  85                  90                  95 ggg caa tcg aat gga att gac gct act cta cag gat gtt acg atg act     875
Gly Gln Ser Asn Gly Ile Asp Ala Thr Leu Gln Asp Val Thr Met Thr
            100                 105                 110 ggg aat ttg ggg gta ctg aag agc caa att gct gat ttg gaa gaa gtt     923
Gly Asn Leu Gly Val Leu Lys Ser Gln Ile Ala Asp Leu Glu Glu Val
        115                 120                 125 cct cac aca att gta aga caa gcc aga act att gaa gat tac gaa ttt     971
Pro His Thr Ile Val Arg Gln Ala Arg Thr Ile Glu Asp Tyr Glu Phe
    130                 135                 140 cct gta cac aga ttg acg aaa aag tta caa gat cct gaa aaa ctg cct    1019
Pro Val His Arg Leu Thr Lys Lys Leu Gln Asp Pro Glu Lys Leu Pro
145                 150                 155 ctg atc atc gtt gct tgt gga tca ttt tct ccc ata aca tac cta cat    1067
Leu Ile Ile Val Ala Cys Gly Ser Phe Ser Pro Ile Thr Tyr Leu His
160                 165                 170                 175 ttg aga atg ttt gaa atg gct tta gat gat atc aat gag caa acg cgt    1115
Leu Arg Met Phe Glu Met Ala Leu Asp Asp Ile Asn Glu Gln Thr Arg
            180                 185                 190 ttt gaa gtg gtt ggt ggt tat ttt tct cca gta agt gat aac tat caa    1163
Phe Glu Val Val Gly Gly Tyr Phe Ser Pro Val Ser Asp Asn Tyr Gln
        195                 200                 205 aag cga ggg tta gcc cca gct tat cat cgt gtc cgc atg tgc gaa tta    1211
Lys Arg Gly Leu Ala Pro Ala Tyr His Arg Val Arg Met Cys Glu Leu
    210                 215                 220 gca tgc gag cgg aca tca tct tgg tta atg gtt gat gcc tgg gaa tct    1259
Ala Cys Glu Arg Thr Ser Ser Trp Leu Met Val Asp Ala Trp Glu Ser
225                 230                 235 tta caa tca agt tat aca agg aca gca aaa gtc ttg gac cat ttc aat    1307
```

```
Leu Gln Ser Ser Tyr Thr Arg Thr Ala Lys Val Leu Asp His Phe Asn
240                 245                 250                 255 cat gaa ata aat atc aag aga ggt gga atc atg act gta gat ggt gaa      1355
His Glu Ile Asn Ile Lys Arg Gly Gly Ile Met Thr Val Asp Gly Glu
                    260                 265                 270 aaa atg ggc gta aaa atc atg tta ttg gca ggc ggt gat ctt atc gaa      1403
Lys Met Gly Val Lys Ile Met Leu Leu Ala Gly Gly Asp Leu Ile Glu
                275                 280                 285 tcc atg ggc gag cct cat gtg tgg gct gat tca gac ctg cac cat att      1451
Ser Met Gly Glu Pro His Val Trp Ala Asp Ser Asp Leu His His Ile
            290                 295                 300 ttg ggt aat tat gga tgt ttg atc gtg gaa agg act ggt tct gat gtt      1499
Leu Gly Asn Tyr Gly Cys Leu Ile Val Glu Arg Thr Gly Ser Asp Val
        305                 310                 315 agg tcc ttc ttg ctt tcc cat gat atc atg tat gaa cac aga aga aat      1547
Arg Ser Phe Leu Leu Ser His Asp Ile Met Tyr Glu His Arg Arg Asn
320                 325                 330                 335 atc ctt att atc aaa caa ctt att tac aat gat att tcc tct acg aaa      1595
Ile Leu Ile Ile Lys Gln Leu Ile Tyr Asn Asp Ile Ser Ser Thr Lys
                    340                 345                 350 gtg cgg ctt ttc atc aga cgt gga atg tca gtt caa tat ctt ctt cca      1643
Val Arg Leu Phe Ile Arg Arg Gly Met Ser Val Gln Tyr Leu Leu Pro
                355                 360                 365 aac tct gtc atc cgt tac atc caa gag tat aat cta tac att aat caa      1691
Asn Ser Val Ile Arg Tyr Ile Gln Glu Tyr Asn Leu Tyr Ile Asn Gln
            370                 375                 380 agt gaa ccg gtc aag cag gtc ttg gat agc aaa gag tgagtttatt           1737
Ser Glu Pro Val Lys Gln Val Leu Asp Ser Lys Glu
        385                 390                 395 acaactctga tactgcagca gttcaaattt accactttcc tcttcaaggt gcatagaaaa    1797
aaagttcctg gatgcacgat ttaaaatgtt tacagcagag caacaatcat gtgaacaatg    1857
tcaaacattt attttaacac ttaataatta taatataacc acaccagcgg taagtttcat    1917
aaggaaaacc tttcagacaa acattccagt gaatcgtata cgtaaatcag caaaattagc    1977
ttataaaata cagaatccga agatacttga tctactcgcg ttactattaa tgcgggtaat    2037
gatctatatt gaattttgca cgtctatagt aacttaaaag tcttgtaata tttgaagtaa    2097
caatgccgta taatactgca taatagccct atcaatcgga atataccaaa acatcctttt   2156

<210> SEQ ID NO 17
<211> LENGTH: 395
<212> TYPE: PRT
<213> ORGANISM: Saccharomyces cerevisiae

<400> SEQUENCE: 17

Met Asp Pro Thr Lys Ala Pro Asp Phe Lys Pro Pro Gln Pro Asn Glu
1               5                   10                  15

Glu Leu Gln Pro Pro Asp Pro Thr His Thr Ile Pro Lys Ser Gly
                20                  25                  30

Pro Ile Val Pro Tyr Val Leu Ala Asp Tyr Asn Ser Ser Ile Asp Ala
            35                  40                  45

Pro Phe Asn Leu Asp Ile Tyr Lys Thr Leu Ser Ser Arg Lys Lys Asn
        50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Ser Glu Glu Ser Glu Gly
                85                  90                  95
```

```
Gln Ser Asn Gly Ile Asp Ala Thr Leu Gln Asp Val Thr Met Thr Gly
                100                 105                 110
Asn Leu Gly Val Leu Lys Ser Gln Ile Ala Asp Leu Glu Glu Val Pro
            115                 120                 125
His Thr Ile Val Arg Gln Ala Arg Thr Ile Glu Asp Tyr Glu Phe Pro
        130                 135                 140
Val His Arg Leu Thr Lys Lys Leu Gln Asp Pro Glu Lys Leu Pro Leu
145                 150                 155                 160
Ile Ile Val Ala Cys Gly Ser Phe Ser Pro Ile Thr Tyr Leu His Leu
                165                 170                 175
Arg Met Phe Glu Met Ala Leu Asp Asp Ile Asn Glu Gln Thr Arg Phe
            180                 185                 190
Glu Val Gly Gly Tyr Phe Ser Pro Val Ser Asp Asn Tyr Gln Lys
        195                 200                 205
Arg Gly Leu Ala Pro Ala Tyr His Arg Val Arg Met Cys Glu Leu Ala
        210                 215                 220
Cys Glu Arg Thr Ser Ser Trp Leu Met Val Asp Ala Trp Glu Ser Leu
225                 230                 235                 240
Gln Ser Ser Tyr Thr Arg Thr Ala Lys Val Leu Asp His Phe Asn His
                245                 250                 255
Glu Ile Asn Ile Lys Arg Gly Gly Ile Met Thr Val Asp Gly Glu Lys
            260                 265                 270
Met Gly Val Lys Ile Met Leu Leu Ala Gly Gly Asp Leu Ile Glu Ser
        275                 280                 285
Met Gly Glu Pro His Val Trp Ala Asp Ser Asp Leu His His Ile Leu
        290                 295                 300
Gly Asn Tyr Gly Cys Leu Ile Val Glu Arg Thr Gly Ser Asp Val Arg
305                 310                 315                 320
Ser Phe Leu Leu Ser His Asp Ile Met Tyr Glu His Arg Arg Asn Ile
                325                 330                 335
Leu Ile Ile Lys Gln Leu Ile Tyr Asn Asp Ile Ser Ser Thr Lys Val
            340                 345                 350
Arg Leu Phe Ile Arg Arg Gly Met Ser Val Gln Tyr Leu Leu Pro Asn
        355                 360                 365
Ser Val Ile Arg Tyr Ile Gln Glu Tyr Asn Leu Tyr Ile Asn Gln Ser
        370                 375                 380
Glu Pro Val Lys Gln Val Leu Asp Ser Lys Glu
385                 390                 395

<210> SEQ ID NO 18
<211> LENGTH: 2156
<212> TYPE: DNA
<213> ORGANISM: Saccharomyces cerevisiae

<400> SEQUENCE: 18
aaaggatgtt ttggtatatt ccgattgata gggctattat gcagtattat acggcattgt      60
tacttcaaat attacaagac ttttaagtta ctatagacgt gcaaaattca atatagatca     120
ttacccgcat taatagtaac gcgagtagat caagtatctt cggattctgt attttataag     180
ctaattttgc tgatttacgt atacgattca ctggaatgtt tgtctgaaag gttttcctta     240
tgaaacttac cgctggtgtg gttatattat aattattaag tgttaaaata aatgtttgac     300
attgttcaca tgattgttgc tctgctgtaa acattttaaa tcgtgcatcc aggaactttt     360
tttctatgca ccttgaagag gaaagtggta aatttgaact gctgcagtat cagagttgta     420
```

-continued

```
ataaactcac tctttgctat ccaagacctg cttgaccggt tcactttgat taatgtatag    480
attatactct tggatgtaac ggatgacaga gtttggaaga agatattgaa ctgacattcc    540
acgtctgatg aaaagccgca ctttcgtaga ggaaatatca ttgtaaataa gttgtttgat    600
aataaggata tttcttctgt gttcatacat gatatcatgg aaagcaaga aggacctaac     660 atcagaacca gtcctttcca cgatcaaaca tccataatta cccaaaatat ggtgcaggtc    720
tgaatcagcc cacacatgag gctcgcccat ggattcgata agatcaccgc ctgccaataa    780 catgatttt acgcccattt tttcaccatc tacagtcatg attccacctc tcttgatatt     840
tatttcatga ttgaaatggt ccaagacttt tgctgtcctt gtataacttg attgtaaaga    900
ttcccaggca tcaaccatta ccaagatga tgtccgctcg catgctaatt cgcacatgcg     960
gacacgatga taagctgggg ctaaccctcg cttttgatag ttatcactta ctggagaaaa   1020
ataaccacca accacttcaa aacgcgtttg ctcattgata tcatctaaag ccatttcaaa   1080
cattctcaaa tgtaggtatg ttatgggaga aaatgatcca caagcaacga tgatcagagg   1140 cagttttca ggatcttgta acttttcgt caatctgtgt acaggaaatt cgtaatcttc      1200
aatagttctg gcttgtctta caattgtgtg aggaacttct tccaaatcag caatttggct   1260
cttcagtacc cccaaattcc cagtcatcgt aacatcctgt agagtagcgt caattccatt   1320
cgattgccct tcactttcct cctccgatga tacatcccga gatagtggct ggaagtcact   1380
agtatttaat ggaatatggt ccattcggtt gcttgagttg gcgttttttt tccttgacga   1440
cagggttttg taaatgtcga gattgaaagg agcatcgatc gaagaattat aatcagctaa   1500
aacatatgga actatgggtc cagattttg tatcgtatgt gttggatctg gcggtggttg    1560
tagttcttca tttggctgtg gcggtttaaa atcgggtgct ttggtgggat ccattacgta   1620
ataagtgcac ttttcttgc cttctccact ttaaactctc tctctctctc tacttaacag    1680
tggaggaaca gtgactaagg tagagtatga ttgtactata acttacagtc tactgtcgtc   1740
acgctgggtc aatttacatt gttatttttc ttggagacga caccgtcaca tatggacagc   1800
gagtatggta gatggtataa gcaaaaaatg gccagaaaca ggcgattatt tggtaaaacg   1860
taaagattga tcaagacgat aagtttgaga gattgtgaag ctaaataaaa tcgtattgcg   1920
agtattttac attccatata cgaatagtac gatatccatg tggggtgcga ctcagagact   1980
ttctattacc cgtctttcaa aaagaaatga gatacgttga tcctgctttt aacaatttcg   2040
aatcgtttgc gtaattatat gacttgctcc ggtgtataaa taaataaagt acattcttgg   2100
tactcctgaa cctagcctgg agtaactcgg aataatacac cattgacacc aaaaga       2156
```

<210> SEQ ID NO 19
<211> LENGTH: 3343
<212> TYPE: DNA
<213> ORGANISM: Saccharomyces cerevisiae
<220> FEATURE:
<221> NAME/KEY: CDS
<222> LOCATION: (1526)...(2728)

<400> SEQUENCE: 19

```
gtttgaattg tgtttgtgtt agaaatttgt gtgctttaat gttatgttat aatgaaatct     60
tattagattt atttaacgtt tttgctgtgc ttataataaa cattacataa taaaggagt     120 agaagaaagt ggtagagagg agtacaaatc tacctgccag aactctctcc ttatatatat    180
ttccagtggt gtctggatta cctacctcaa gccataccat atccatacca tatccataaa    240
cgcctacaaa atttctaccc caatccagca gcttctatca ctatctcgta taccaccata    300
```

-continued

```
ggcaccacca ctgtttgtgt aaatttactc ctgaggggg ggtggctcaa cacggtgtag    360
gccttcttcc cgcacaatcc gatgaaaccc cacaatcgcc tccgtctctt ccactgtgca    420
cggcgctagc tcaacatctt ccccgccaca tttactgtgg caaagaaggt gcataatcta    480
aaaaaacata cgtatgagaa tggaaagggc aagataatat cggaccgtag tgagtcactt    540
gcttttggta ttgcaaccaa ctgccgcccc tcttcccgct cttgcaccaa aacgctaaat    600
gcccattgtg atggctcatc caccctcacg acgaagtaag acccgggca caagaaaata    660 cgagatcata acagttcgag tccgtttatt gtgtgcggtt ttggtacgct ttttcgtgag    720
gtgtactacc attcatgaga gtcgttttag gagctgtcat gaaagatatg tatcttgttg    780
atgaactgta aaaatttgca gaattgcgc tattccgttt atttcattgt cgattcggtg    840
ttaatattag gggtacaaaa tatactagaa gttctccctc gaggatatag gaatgcgcaa    900
atgggcattt gatgtgacac aaaatttgga caatataacg attcattttt agatcgttgt    960
tcaaccgtcc cagtggccga gtggttaagg cgatgcctgc tatttcctca gaaaagcaat   1020
taggcattgg gttttacctg cgcaggttcg aatcctgtct gtgacgcttt ttttaatttc   1080
tttactccat gacaaaagcg gataaaaatt cccgcattcg gcgtaaaaaa atccggtttt   1140 tttttttagca ctcgctgttt ttgcctctac cgggtgaaaa atgacgatga agacggctgg   1200
aattgcgctg catccgctta cgtaggatag aacacctaca aagatttacg aactttattg   1260
ctcgaagatt cgctatccat atcttttag tttcccccca tttcacaatg ggataccgtt   1320
gttttttctg taggtacgct ttctcatagt taatagagtc agtaattcat ttcattttt   1380 gcagaaagga atttcttcac ctaatttaga atttcatcaa catttattgt atctgcatgg   1440
tataacaaat tagaaaaatt tggaagggaa aaaaaaactg ttgcgtcaat tacttatacc   1500
agggatagaa aaaaaaaag gaaac atg gat ccc aca aga gct ccg gat ttc     1552
                              Met Asp Pro Thr Arg Ala Pro Asp Phe
                                1               5 aaa ccg cca tct gca gac gag gaa ttg att cct cca ccc gac ccg gaa     1600
Lys Pro Pro Ser Ala Asp Glu Glu Leu Ile Pro Pro Pro Asp Pro Glu
 10              15                  20                  25 tct aaa att ccc aaa tct att cca att att cca tac gtc tta gcc gat     1648
Ser Lys Ile Pro Lys Ser Ile Pro Ile Ile Pro Tyr Val Leu Ala Asp
             30                  35                  40 gcg aat tcc tct ata gat gca cct ttt aat att aag agg aag aaa aag     1696
Ala Asn Ser Ser Ile Asp Ala Pro Phe Asn Ile Lys Arg Lys Lys Lys
         45                  50                  55 cat cct aag cat cat cat cac cat cat cac agt cgt aaa gaa ggc aat     1744
His Pro Lys His His His His His His Ser Arg Lys Glu Gly Asn
     60                  65                  70 gat aaa aaa cat cag cat att cca ttg aac caa gac gac ttt caa cca     1792
Asp Lys Lys His Gln His Ile Pro Leu Asn Gln Asp Asp Phe Gln Pro
 75                  80                  85 ctt tcc gca gaa gtg tct tcc gaa gat gat gac gcg gat ttt aga tcc     1840
Leu Ser Ala Glu Val Ser Ser Glu Asp Asp Asp Ala Asp Phe Arg Ser
 90                  95                  100                 105 aag gag aga tac ggt tca gat tca acc aca gaa tca gaa act aga ggt     1888
Lys Glu Arg Tyr Gly Ser Asp Ser Thr Thr Glu Ser Glu Thr Arg Gly
             110                 115                 120 gtt cag aaa tat cag att gct gat tta gaa gaa gtt cca cat gga atc     1936
Val Gln Lys Tyr Gln Ile Ala Asp Leu Glu Glu Val Pro His Gly Ile
         125                 130                 135 gtt cgt caa gca aga acc ttg gaa gac tac gaa ttc ccc tca cac aga     1984
Val Arg Gln Ala Arg Thr Leu Glu Asp Tyr Glu Phe Pro Ser His Arg
     140                 145                 150
```

-continued

| | |
|---|---|
| tta tcg aaa aaa tta ctg gat cca aat aaa ctg ccg tta gta ata gta<br>Leu Ser Lys Lys Leu Leu Asp Pro Asn Lys Leu Pro Leu Val Ile Val<br>      155                      160                      165 | 2032 |
| gca tgt ggg tct ttt tca cca atc acc tac ttg cat cta aga atg ttt<br>Ala Cys Gly Ser Phe Ser Pro Ile Thr Tyr Leu His Leu Arg Met Phe<br>170                      175                      180                      185 | 2080 |
| gaa atg gct tta gat gca atc tct gaa caa aca agg ttt gaa gtc ata<br>Glu Met Ala Leu Asp Ala Ile Ser Glu Gln Thr Arg Phe Glu Val Ile<br>                      190                      195                      200 | 2128 |
| ggt gga tat tac tcc cct gtt agt gat aac tat caa aag caa ggc ttg<br>Gly Gly Tyr Tyr Ser Pro Val Ser Asp Asn Tyr Gln Lys Gln Gly Leu<br>      205                      210                      215 | 2176 |
| gcc cca tcc tac cat aga gta cgt atg tgt gaa ttg gcc tgc gaa aga<br>Ala Pro Ser Tyr His Arg Val Arg Met Cys Glu Leu Ala Cys Glu Arg<br>          220                      225                      230 | 2224 |
| acc tca tct tgg ttg atg gtg gat gca tgg gag tca ttg caa cct tca<br>Thr Ser Ser Trp Leu Met Val Asp Ala Trp Glu Ser Leu Gln Pro Ser<br>              235                      240                      245 | 2272 |
| tac aca aga act gcc aag gtc ttg gat cat ttc aat cac gaa atc aat<br>Tyr Thr Arg Thr Ala Lys Val Leu Asp His Phe Asn His Glu Ile Asn<br>250                      255                      260                      265 | 2320 |
| att aag aga ggt ggt gta gct act gtt act gga gaa aaa att ggt gtg<br>Ile Lys Arg Gly Gly Val Ala Thr Val Thr Gly Glu Lys Ile Gly Val<br>                      270                      275                      280 | 2368 |
| aaa ata atg ttg ctg gct ggt ggt gac cta ata gag tca atg ggt gaa<br>Lys Ile Met Leu Leu Ala Gly Gly Asp Leu Ile Glu Ser Met Gly Glu<br>              285                      290                      295 | 2416 |
| cca aac gtt tgg gcg gac gcc gat tta cat cac att ctc ggt aat tac<br>Pro Asn Val Trp Ala Asp Ala Asp Leu His His Ile Leu Gly Asn Tyr<br>          300                      305                      310 | 2464 |
| ggt tgt ttg att gtc gaa cgt act ggt tct gat gta agg tct ttt ttg<br>Gly Cys Leu Ile Val Glu Arg Thr Gly Ser Asp Val Arg Ser Phe Leu<br>      315                      320                      325 | 2512 |
| tta tcc cat gat att atg tat gaa cat aga agg aat att ctt atc atc<br>Leu Ser His Asp Ile Met Tyr Glu His Arg Arg Asn Ile Leu Ile Ile<br>330                      335                      340                      345 | 2560 |
| aag caa ctc atc tat aat gat att tct tcc acg aaa gtt cgt cta ttt<br>Lys Gln Leu Ile Tyr Asn Asp Ile Ser Ser Thr Lys Val Arg Leu Phe<br>                      350                      355                      360 | 2608 |
| atc aga cgc gcc atg tct gta caa tat ttg tta cct aat tcg gtc atc<br>Ile Arg Arg Ala Met Ser Val Gln Tyr Leu Leu Pro Asn Ser Val Ile<br>          365                      370                      375 | 2656 |
| agg tat atc caa gaa cat aga cta tat gtg gac caa acc gaa cct gtt<br>Arg Tyr Ile Gln Glu His Arg Leu Tyr Val Asp Gln Thr Glu Pro Val<br>              380                      385                      390 | 2704 |
| aag caa gtt ctt gga aac aaa gaa tgatttgccg tccggaattg cttcgttctt<br>Lys Gln Val Leu Gly Asn Lys Glu<br>      395                      400 | 2758 |
| tctttcatct ttctctttac aatttccaat tttccctac aggaattaat tggagggtac | 2818 |
| aagcgagtag aaatgtgaca tatgacttac ctatctgtgt tttagtatag ttttttttc | 2878 |
| tgtagtataa ttcactttta cactaatttt ttcgcctttt tctcttaaag agctaatttc | 2938 |
| tataaccttc agcggttata ccaaatataa aaaatggaag gaaaacaaac agtaagaaat | 2998 |
| aagcgcaaca gcacgttagt tcaccattgg attccaacat ttcaaaattt aatctaatgg | 3058 |
| caagagatat cacattttg accgtatttt tagaaagttg tggcgctgta aataatgatg | 3118 |
| aggcaggaaa attgttatct gcttggactt caaccgtacg cattgaggga ccggaatcaa | 3178 |

-continued

```
ccgactctaa ttcattatat attccactgc taccacctgg aatgttgaaa gtatgtttct    3238
cctagcaaaa ttaaaaccca tccgtgaatg aagcgttact aactataata actggtagct    3298
ttgtcactcg taccaggaaa agtgaagatt aaactgaatt ttaaa                    3343
```

<210> SEQ ID NO 20
<211> LENGTH: 401
<212> TYPE: PRT
<213> ORGANISM: Saccharomyces cerevisiae

<400> SEQUENCE: 20

```
Met Asp Pro Thr Arg Ala Pro Asp Phe Lys Pro Ser Ala Asp Glu
 1               5                  10                  15

Glu Leu Ile Pro Pro Asp Pro Glu Ser Lys Ile Pro Lys Ser Ile
                20                  25                  30

Pro Ile Ile Pro Tyr Val Leu Ala Asp Ala Asn Ser Ser Ile Asp Ala
                35                  40                  45

Pro Phe Asn Ile Lys Arg Lys Lys Lys His Pro Lys His His His
    50                  55                  60

His His His Ser Arg Lys Glu Gly Asn Asp Lys Lys His Gln His Ile
 65                  70                  75                  80

Pro Leu Asn Gln Asp Asp Phe Gln Pro Leu Ser Ala Glu Val Ser Ser
                85                  90                  95

Glu Asp Asp Ala Asp Phe Arg Ser Lys Glu Arg Tyr Gly Ser Asp
                100                 105                 110

Ser Thr Thr Glu Ser Glu Thr Arg Gly Val Gln Lys Tyr Gln Ile Ala
                115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
                180                 185                 190

Ser Glu Gln Thr Arg Phe Glu Val Ile Gly Gly Tyr Tyr Ser Pro Val
                195                 200                 205

Ser Asp Asn Tyr Gln Lys Gln Gly Leu Ala Pro Ser Tyr His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
                260                 265                 270

Thr Val Thr Gly Glu Lys Ile Gly Val Lys Ile Met Leu Leu Ala Gly
                275                 280                 285

Gly Asp Leu Ile Glu Ser Met Gly Glu Pro Asn Val Trp Ala Asp Ala
                290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Ile Lys Gln Leu Ile Tyr Asn Asp
                340                 345                 350
```

```
Ile Ser Ser Thr Lys Val Arg Leu Phe Ile Arg Arg Ala Met Ser Val
        355                 360                 365
Gln Tyr Leu Leu Pro Asn Ser Val Ile Arg Tyr Ile Gln Glu His Arg
    370                 375                 380
Leu Tyr Val Asp Gln Thr Glu Pro Val Lys Gln Val Leu Gly Asn Lys
385                 390                 395                 400
Glu

<210> SEQ ID NO 21
<211> LENGTH: 3343
<212> TYPE: DNA
<213> ORGANISM: Saccharomyces cerevisiae

<400> SEQUENCE: 21
```

| | | | | | |
|---|---|---|---|---|---|
| tttaaaattc | agtttaatct | tcactttcc | tggtacgagt | gacaaagcta | ccagttatta | 60 |
| tagttagtaa | cgcttcattc | acggatgggt | tttaattttg | ctaggagaaa | catactttca | 120 |
| acattccagg | tggtagcagt | ggaatatata | atgaattaga | gtcggttgat | tccggtccct | 180 |
| caatgcgtac | ggttgaagtc | caagcagata | acaattttcc | tgcctcatca | ttatttacag | 240 |
| cgccacaact | ttctaaaaat | acggtcaaaa | atgtgatatc | tcttgccatt | agattaaatt | 300 |
| ttgaaatgtt | ggaatccaat | ggtgaactaa | cgtgctgttg | cgcttatttc | ttactgtttg | 360 |
| ttttccttcc | atttttata | tttggtataa | ccgctgaagg | ttatagaaat | tagctcttta | 420 |
| agagaaaaag | gcgaaaaaat | tagtgtaaaa | gtgaattata | ctacagaaaa | aaaaactata | 480 |
| ctaaaacaca | gataggtaag | tcatatgtca | catttctact | cgcttgtacc | ctccaattaa | 540 |
| ttcctgtagg | ggaaaattgg | aaattgtaaa | gagaaagatg | aaagaaagaa | cgaagcaatt | 600 |
| ccggacggca | aatcattctt | tgtttccaag | aacttgctta | acaggttcgg | tttggtccac | 660 |
| atatagtcta | tgttcttgga | tatacctgat | gaccgaatta | ggtaacaaat | attgtacaga | 720 |
| catggcgcgt | ctgataaata | gacgaacttt | cgtggaagaa | atatcattat | agatgagttg | 780 |
| cttgatgata | agaatattcc | ttctatgttc | atacataata | tcatgggata | caaaaaaga | 840 |
| ccttacatca | gaaccagtac | gttcgacaat | caaacaaccg | taattaccga | gaatgtgatg | 900 |
| taaatcggcg | tccgcccaaa | cgtttggttc | acccattgac | tctattaggt | caccaccagc | 960 |
| cagcaacatt | attttcacac | caattttttc | tccagtaaca | gtagctacac | cacctctctt | 1020 |
| aatattgatt | tcgtgattga | atgatccaa | gaccttggca | gttcttgtgt | atgaaggttg | 1080 |
| caatgactcc | catgcatcca | ccatcaacca | agatgaggtt | ctttcgcagg | ccaattcaca | 1140 |
| catacgtact | ctatggtagg | atggggccaa | gccttgcttt | tgatagttat | cactaacagg | 1200 |
| ggagtaatat | ccacctatga | cttcaaacct | tgtttgttca | gagattgcat | ctaaagccat | 1260 |
| ttcaaacatt | cttagatgca | agtaggtgat | tggtgaaaaa | gacccacatg | ctactattac | 1320 |
| taacggcagt | ttatttggat | ccagtaattt | tttcgataat | ctgtgtgagg | ggaattcgta | 1380 |
| gtcttccaag | gttcttgctt | gacgaacgat | tccatgtgga | acttcttcta | aatcagcaat | 1440 |
| ctgatatttc | tgaacacctc | tagtttctga | ttctgtggtt | gaatctgaac | cgtatctctc | 1500 |
| cttggatcta | aaatccgcgt | catcatcttc | ggaagacact | tctgcggaaa | gtggttgaaa | 1560 |
| gtcgtcttgg | ttcaatggaa | tatgctgatg | ttttttatca | ttgccttctt | tacgactgtg | 1620 |
| atgatggtga | tgatgatgct | taggatgctt | tttcttcctc | ttaatattaa | aaggtgcatc | 1680 |
| tatagaggaa | ttcgcatcgg | ctaagacgta | tggaataatt | ggaatagatt | tgggaatttt | 1740 |
| agattccggg | tcgggtggag | gaatcaattc | ctcgtctgca | gatggcggtt | tgaaatccgg | 1800 |

```
agctcttgtg ggatccatgt ttcctttttt tttttctatc cctggtataa gtaattgacg    1860
caacagtttt ttttttccctt ccaaattttt ctaatttgtt ataccatgca gatacaataa    1920
atgttgatga aattctaaat taggtgaaga aattcctttc tgcaaaaaat gaaatgaatt    1980
actgactcta ttaactatga gaaagcgtac ctacagaaaa aacaacggta tcccattgtg    2040
aaatgggggg aaactaaaaa gatatggata gcgaatcttc gagcaataaa gttcgtaaat    2100
ctttgtaggt gttctatcct acgtaagcgg atgcagcgca attccagccg tcttcatcgt    2160
cattttcac ccgtagagg caaaaacagc gagtgctaaa aaaaaaaccg gatttttta      2220
cgccgaatgc gggaattttt atccgctttt gtcatggagt aaagaaatta aaaaagcgt    2280
cacagacagg attcgaacct cgcaggtaa aacccaatgc ctaattgctt ttctgaggaa    2340
atagcaggca tcgccttaac cactcggcca ctgggacggt tgaacaacga tctaaaaatg    2400
aatcgttata ttgtccaaat tttgtgtcac atcaaatgcc catttgcgca ttcctatatc    2460
ctcgagggag aacttctagt atattttgta ccctaatat taacaccgaa tcgacaatga    2520
aataaacgga atagcgcaat ttctgcaaat tttacagtt catcaacaag atacatatct    2580
ttcatgacag ctcctaaaac gactctcatg aatggtagta caccctcacga aaaagcgtac    2640
caaaaccgca cacaataaac ggactcgaac tgttatgatc tcgtattttc ttgtgccccg    2700
ggtcttactt cgtcgtgagg gtggatgagc catcacaatg ggcatttagc gttttggtgc    2760
aagagcggga agagggcgg cagttggttg caataccaaa agcaagtgac tcactacggt    2820
ccgatattat cttgcccttt ccattctcat acgtatgttt tttagatta tgcaccttct    2880
ttgccacagt aaatgtggcg gggaagatgt tgagctagcg ccgtgcacag tggaagagac    2940
ggaggcgatt gtggggtttc atcggattgt gcgggaagaa ggcctacacc gtgttgagcc    3000
accccccct caggagtaaa tttacacaaa cagtggtggt gcctatggtg gtatacgaga    3060
tagtgataga agctgctgga ttggggtaga aattttgtag gcgtttatgg atatggtatg    3120
gatatggtat ggcttgaggt aggtaatcca gacaccactg gaaatatata taaggagaga    3180
gttctggcag gtagatttgt actcctctct accactttct tctactcctt ttattatgta    3240
atgtttatta taagcacagc aaaaacgtta aataaatcta ataagatttc attataacat    3300
aacattaaag cacacaaatt tctaacacaa acacaattca aac                      3343
```

<210> SEQ ID NO 22
<211> LENGTH: 1900
<212> TYPE: DNA
<213> ORGANISM: Saccharomyces cerevisiae
<220> FEATURE:
<221> NAME/KEY: CDS
<222> LOCATION: (813)...(1853)

<400> SEQUENCE: 22

```
ttctactact ccacgtacaa aaaagagcac gctgctttat ttatactttt gtgccacaag      60
aatgatcaac atcaacataa atatcaacta gtatctgcaa cacatctgct ccacggaact     120
aaacccgttg agcagtgccc cgtggaaacg taaactatcg caaattggga ttaacaagcc    180
aaaaacagcc aagcaagatt cacgaaaccg cgcctcgttt ggaccccgaa ggcccattta    240
acggccggcc gttacaagca agatcggcag agcaaaccac tccccagcac cacagcacat    300
cactgcacga gcaacaataa ctagaacatg gcagatagcg aggatacctc tgtgatcctg    360
cagggcatcg acacaatcaa cagcgtggag ggcctggaag aagatggtta cctcagcgac    420
gaggacacgt cactcagcaa cgagctcgca gatgcacagc gtcaatggga agagtcgctg    480
```

```
caacagttga acaagctgct caactgggtc ctgctgcccc tgctgggcaa gtatataggt      540
aggagaatgg ccaagactct atggagtagg ttcattgaac actttgtata agtgtttgtt      600
gtttatgtat ccgcatatag cagttataac agataaatgg cactttcgc acaccgttg       660 ttttatctcc gatagtacgt gggcctttat ttatggtcgt ttaacgaaag aacggcatct      720
tgaattgagc aggtatttaa aagataggac gagaaacaag cacatgatct gtgtcgaaaa      780
aaagtagcaa agagaaaaag taggaggata gg atg aac agg aaa gta gct atc       833
                                    Met Asn Arg Lys Val Ala Ile
                                     1               5 gta acg ggt act aat agt aat ctt ggt ctg aac att gtg ttc cgt ctg        881
Val Thr Gly Thr Asn Ser Asn Leu Gly Leu Asn Ile Val Phe Arg Leu
         10                  15                  20 att gaa act gag gac acc aat gtc aga ttg acc att gtg gtg act tct        929
Ile Glu Thr Glu Asp Thr Asn Val Arg Leu Thr Ile Val Val Thr Ser
 25                  30                  35 aga acg ctt cct cga gtg cag gag gtg att aac cag att aaa gat ttt        977
Arg Thr Leu Pro Arg Val Gln Glu Val Ile Asn Gln Ile Lys Asp Phe
 40                  45                  50                  55 tac aac aaa tca ggc cgt gta gag gat ttg gaa ata gac ttt gat tat       1025
Tyr Asn Lys Ser Gly Arg Val Glu Asp Leu Glu Ile Asp Phe Asp Tyr
                 60                  65                  70 ctg ttg gtg gac ttc acc aac atg gtg agt gtc ttg aac gca tat tac       1073
Leu Leu Val Asp Phe Thr Asn Met Val Ser Val Leu Asn Ala Tyr Tyr
             75                  80                  85 gac atc aac aaa aag tac agg gcg ata aac tac ctt ttc gtg aat gct       1121
Asp Ile Asn Lys Lys Tyr Arg Ala Ile Asn Tyr Leu Phe Val Asn Ala
         90                  95                 100 gcg caa ggt atc ttt gac ggt ata gat tgg atc gga gcg gtc aag gag       1169
Ala Gln Gly Ile Phe Asp Gly Ile Asp Trp Ile Gly Ala Val Lys Glu
    105                 110                 115 gtt ttc acc aat cca ttg gag gca gtg aca aat ccg aca tac aag ata       1217
Val Phe Thr Asn Pro Leu Glu Ala Val Thr Asn Pro Thr Tyr Lys Ile
120                 125                 130                 135 caa ctg gtg ggc gtc aag tct aaa gat gac atg ggg ctt att ttc cag       1265
Gln Leu Val Gly Val Lys Ser Lys Asp Asp Met Gly Leu Ile Phe Gln
                140                 145                 150 gcc aat gtg ttt ggt ccg tac tac ttt atc agt aaa att ctg cct caa       1313
Ala Asn Val Phe Gly Pro Tyr Tyr Phe Ile Ser Lys Ile Leu Pro Gln
            155                 160                 165 ttg acc agg gga aag gct tat att gtt tgg att tcg agt att atg tcc       1361
Leu Thr Arg Gly Lys Ala Tyr Ile Val Trp Ile Ser Ser Ile Met Ser
        170                 175                 180 gat cct aag tat ctt tcg ttg aac gat att gaa cta cta aag aca aat       1409
Asp Pro Lys Tyr Leu Ser Leu Asn Asp Ile Glu Leu Leu Lys Thr Asn
    185                 190                 195 gcc tct tat gag ggc tcc aag cgt tta gtt gat tta ctg cat ttg gcc       1457
Ala Ser Tyr Glu Gly Ser Lys Arg Leu Val Asp Leu Leu His Leu Ala
200                 205                 210                 215 acc tac aaa gac ttg aaa aag ctg ggc ata aat cag tat gta gtt caa       1505
Thr Tyr Lys Asp Leu Lys Lys Leu Gly Ile Asn Gln Tyr Val Val Gln
                220                 225                 230 ccg ggc ata ttt aca agc cat tcc ttc tcc gaa tat ttg aat ttt ttc       1553
Pro Gly Ile Phe Thr Ser His Ser Phe Ser Glu Tyr Leu Asn Phe Phe
            235                 240                 245 acc tat ttc ggc atg cta tgc ttg ttc tat ttg gcc agg ctg ttg ggg       1601
Thr Tyr Phe Gly Met Leu Cys Leu Phe Tyr Leu Ala Arg Leu Leu Gly
        250                 255                 260
```

-continued

```
tct cca tgg cac aat att gat ggt tat aaa gct gcc aat gcc cca gta      1649
Ser Pro Trp His Asn Ile Asp Gly Tyr Lys Ala Ala Asn Ala Pro Val
    265                 270                 275 tac gta act aga ttg gcc aat cca aac ttt gag aaa caa gac gta aaa      1697
Tyr Val Thr Arg Leu Ala Asn Pro Asn Phe Glu Lys Gln Asp Val Lys
280                 285                 290                 295 tac ggt tct gct acc tct agg gat ggt atg cca tat atc aag acg cag      1745
Tyr Gly Ser Ala Thr Ser Arg Asp Gly Met Pro Tyr Ile Lys Thr Gln
                300                 305                 310 gaa ata gac cct act gga atg tct gat gtc ttc gct tat ata cag aag      1793
Glu Ile Asp Pro Thr Gly Met Ser Asp Val Phe Ala Tyr Ile Gln Lys
            315                 320                 325 aag aaa ctg gaa tgg gac gag aaa ctg aaa gat caa att gtt gaa act      1841
Lys Lys Leu Glu Trp Asp Glu Lys Leu Lys Asp Gln Ile Val Glu Thr
        330                 335                 340 aga acc ccc att taatatatct ctgcgtacat atgtatatat atatatgtgt          1893
Arg Thr Pro Ile
        345 gtatata                                                              1900

<210> SEQ ID NO 23
<211> LENGTH: 347
<212> TYPE: PRT
<213> ORGANISM: Saccharomyces cerevisiae

<400> SEQUENCE: 23

Met Asn Arg Lys Val Ala Ile Val Thr Gly Thr Asn Ser Asn Leu Gly
  1               5                  10                  15

Leu Asn Ile Val Phe Arg Leu Ile Glu Thr Glu Asp Thr Asn Val Arg
             20                  25                  30

Leu Thr Ile Val Val Thr Ser Arg Thr Leu Pro Arg Val Gln Glu Val
         35                  40                  45

Ile Asn Gln Ile Lys Asp Phe Tyr Asn Lys Ser Gly Arg Val Glu Asp
     50                  55                  60

Leu Glu Ile Asp Phe Asp Tyr Leu Leu Val Asp Phe Thr Asn Met Val
 65                  70                  75                  80

Ser Val Leu Asn Ala Tyr Tyr Asp Ile Asn Lys Lys Tyr Arg Ala Ile
                 85                  90                  95

Asn Tyr Leu Phe Val Asn Ala Ala Gln Gly Ile Phe Asp Gly Ile Asp
            100                 105                 110

Trp Ile Gly Ala Val Lys Glu Val Phe Thr Asn Pro Leu Glu Ala Val
        115                 120                 125

Thr Asn Pro Thr Tyr Lys Ile Gln Leu Val Gly Val Lys Ser Lys Asp
    130                 135                 140

Asp Met Gly Leu Ile Phe Gln Ala Asn Val Phe Gly Pro Tyr Tyr Phe
145                 150                 155                 160

Ile Ser Lys Ile Leu Pro Gln Leu Thr Arg Gly Lys Ala Tyr Ile Val
                165                 170                 175

Trp Ile Ser Ser Ile Met Ser Asp Pro Lys Tyr Leu Ser Leu Asn Asp
            180                 185                 190

Ile Glu Leu Leu Lys Thr Asn Ala Ser Tyr Glu Gly Ser Lys Arg Leu
        195                 200                 205

Val Asp Leu Leu His Leu Ala Thr Tyr Lys Asp Leu Lys Lys Leu Gly
    210                 215                 220

Ile Asn Gln Tyr Val Val Gln Pro Gly Ile Phe Thr Ser His Ser Phe
225                 230                 235                 240
```

-continued

```
Ser Glu Tyr Leu Asn Phe Phe Thr Tyr Phe Gly Met Leu Cys Leu Phe
            245                 250                 255

Tyr Leu Ala Arg Leu Leu Gly Ser Pro Trp His Asn Ile Asp Gly Tyr
            260                 265                 270

Lys Ala Ala Asn Ala Pro Val Tyr Val Thr Arg Leu Ala Asn Pro Asn
            275                 280                 285

Phe Glu Lys Gln Asp Val Lys Tyr Gly Ser Ala Thr Ser Arg Asp Gly
            290                 295                 300

Met Pro Tyr Ile Lys Thr Gln Glu Ile Asp Pro Thr Gly Met Ser Asp
305                 310                 315                 320

Val Phe Ala Tyr Ile Gln Lys Lys Leu Glu Trp Asp Glu Lys Leu
                325                 330                 335

Lys Asp Gln Ile Val Glu Thr Arg Thr Pro Ile
            340                 345
```

<210> SEQ ID NO 24
<211> LENGTH: 1900
<212> TYPE: DNA
<213> ORGANISM: Saccharomyces cerevisiae

<400> SEQUENCE: 24

| | | |
|---|---|---|
| tatatacaca catatatata tatacatatg tacgcagaga tatattaaat ggggggttcta | 60 |
| gtttcaacaa tttgatcttt cagtttctcg tcccattcca gtttcttctt ctgtatataa | 120 |
| gcgaagacat cagacattcc agtagggtct atttcctgcg tcttgatata tggcatacca | 180 |
| tccctagagg tagcagaacc gtattttacg tcttgtttct caaagtttgg attggccaat | 240 |
| tagttacgt atactggggc attggcagct ttataaccat caatattgtg ccatggagac | 300 |
| ccaacagcc tggccaaata gaacaagcat agcatgccga aataggtgaa aaaattcaaa | 360 |
| attcggaga aggaatggct tgtaaatatg cccggttgaa ctacatactg atttatgccc | 420 |
| gctttttca agtctttgta ggtggccaaa tgcagtaaat caactaaacg cttggagccc | 480 |
| cataagagg catttgtctt tagtagttca atatcgttca acgaaagata cttaggatcg | 540 |
| acataaatac tcgaaatcca aacaatataa gcctttcccc tggtcaattg aggcagaatt | 600 |
| tactgataa agtagtacgg accaaacaca ttggcctgga aaataagccc catgtcatct | 660 |
| tagacttga cgcccaccag ttgtatcttg tatgtcggat ttgtcactgc ctccaatgga | 720 |
| tggtgaaaa cctccttgac cgctccgatc caatctatac cgtcaaagat accttgcgca | 780 |
| cattcacga aaaggtagtt tatcgccctg tacttttttgt tgatgtcgta atatgcgttc | 840 |
| agacactca ccatgttggt gaagtccacc aacagataat caaagtctat ttccaaatcc | 900 |
| ctacacggc ctgatttgtt gtaaaaatct ttaatctggt taatcaccte ctgcactcga | 960 |
| gaagcgttc tagaagtcac cacaatggtc aatctgacat tggtgtcctc agtttcaatc | 1020 |
| gacggaaca caatgttcag accaagatta ctattagtac ccgttacgat agctactttc | 1080 |
| tgttcatcc tatcctccta ctttttctct ttgctacttt ttttcgacac agatcatgtg | 1140 |
| ttgtttctc gtccatatctt ttaaataccct gctcaattca agatgccgtt ctttcgttaa | 1200 |
| cgaccataa ataaaggccc acgtactatc ggagataaaa caacgggtgt gcgaaaagtg | 1260 |
| catttatct gttataactg ctatatgcgg atacataaac aacaaacact tatacaaagt | 1320 |
| ttcaatgaa cctactccat agagtcttgg ccattctcct acctatatac ttgcccagca | 1380 |
| gggcagcag gacccagttg agcagcttgt tcaactgttg cagcgactct tccccattgac | 1440 |
| ctgtgcatc tgcgagctcg ttgctgagtg acgtgtcctc gtcgctgagg taaccatctt | 1500 |

-continued

```
ttccaggcc ctccacgctg ttgattgtgt cgatgccctg caggatcaca gaggtatcct    1560 gctatctgc catgttctag ttattgttgc tcgtgcagtg atgtgctgtg gtgctgggga    1620 tggtttgct ctgccgatct tgcttgtaac ggccggccgt taaatgggcc ttcggggtcc    1680 aacgaggcg cggtttcgtg aatcttgctt ggctgttttt ggcttgttaa tcccaatttg    1740 gatagttta cgtttccacg gggcactgct caacgggttt agttccgtgg agcagatgtg    1800 tgcagatac tagttgatat ttatgttgat gttgatcatt cttgtggcac aaaagtataa    1860 taaagcagc gtgctctttt ttgtacgtgg agtagtagaa                           1900
```

<210> SEQ ID NO 25
<211> LENGTH: 59
<212> TYPE: DNA
<213> ORGANISM: Artificial Sequence
<220> FEATURE:
<223> OTHER INFORMATION: primer for PCR

<400> SEQUENCE: 25

```
aggaaagtag ctatcgtaac gggtactaat agtaatcttg gtctcttggc ctcctctag      59
```

<210> SEQ ID NO 26
<211> LENGTH: 59
<212> TYPE: DNA
<213> ORGANISM: Artificial Sequence
<220> FEATURE:
<223> OTHER INFORMATION: primer for PCR

<400> SEQUENCE: 26

```
tacgcagaga tatattaaat gggggttcta gtttcaacaa tttcgttcag aatgacacg      59
```

<210> SEQ ID NO 27
<211> LENGTH: 62
<212> TYPE: DNA
<213> ORGANISM: Artificial Sequence
<220> FEATURE:
<223> OTHER INFORMATION: primer for PCR

<400> SEQUENCE: 27

```
ttaacagccg cgcccatcat gcaagatcct gatggtattg acattctctt ggcctcctct      60
ag                                                                      62
```

<210> SEQ ID NO 28
<211> LENGTH: 59
<212> TYPE: DNA
<213> ORGANISM: Artificial Sequence
<220> FEATURE:
<223> OTHER INFORMATION: primer for PCR

<400> SEQUENCE: 28

```
gcatatcaat tttaacagac ctcgctgaaa gactctgaat cctcgttcag aatgacacg      59
```

<210> SEQ ID NO 29
<211> LENGTH: 429
<212> TYPE: PRT
<213> ORGANISM: Aspergillus nidulans

<400> SEQUENCE: 29

```
Thr Leu Ala Glu Glu Asn Met Thr Leu Phe Ile His Cys Tyr Ser Lys
 1               5                  10                  15

Gly His Glu Asn Leu Gln Val Thr Ala Ile His Ile Leu Cys Asp Met
            20                  25                  30

Leu Ile Ser His Pro Ser Leu Val Ala Pro Val Thr Gln Ala Asp Lys
```

-continued

```
                35                  40                  45
Glu Thr Val Ala Pro Pro Ala Phe Gln Lys Pro Leu Leu Lys Val Phe
         50                  55                  60

Ser Arg Ala Leu Lys Pro Asn Ser Pro Ala Ser Val Gln Thr Ala Ala
 65                  70                  75                  80

Ala Thr Ala Leu Ser Lys Leu Leu Leu Thr Gly Val Phe Thr Pro Ser
                 85                  90                  95

Ala Ala Asn Ile Pro Asp Ala Ile Gln Glu Phe Asn Gln His Ala Ile
            100                 105                 110

Glu Thr Leu Leu Gln Ser Leu Val Val Ser Phe Phe His Pro Arg Thr
            115                 120                 125

Arg Glu Asn Pro Ala Leu Arg Gln Ala Leu Ala Tyr Phe Phe Pro Val
        130                 135                 140

Tyr Cys His Ser Arg Pro Asp Asn Thr Gln His Met Arg Lys Ile Thr
145                 150                 155                 160

Val Pro Val Ile Arg Thr Ile Leu Asn Ser Ala Glu Glu Tyr Tyr Ser
                165                 170                 175

Leu Glu Ala Glu Glu Asp Ser Asp Gly Asp Ile Asp Glu Ser Val Gly
            180                 185                 190

Glu Lys Glu Leu Lys Ala Leu Met Ser Gly Val Leu Gly Met Leu Ala
        195                 200                 205

Glu Trp Thr Asp Glu Arg Arg Val Ile Gly Leu Gly Gly Glu Arg Val
    210                 215                 220

Leu Ala Gly Gly Leu Ala Ser Ser Asn Val Cys Gly Ile Ile His Leu
225                 230                 235                 240

Gln Leu Ile Lys Asp Ile Leu Glu Arg Val Leu Gly Ile Ser Glu Gly
                245                 250                 255

Ser Asn Arg Cys Ser Lys Gln Gln Arg Lys Leu Leu Phe Ser Leu Met
            260                 265                 270

Ser Lys Leu Tyr Ile Ala Pro Pro Thr Ala Leu Ser Arg Ser Ala Ser
        275                 280                 285

Gln Ala Pro Glu Asp Asp Ser Phe Arg Ser Ser Val Arg Ser Ser His
    290                 295                 300

Gly Glu Leu Asn Pro Glu Asn Leu Ala Leu Ala Gln Glu Val Lys Glu
305                 310                 315                 320

Leu Leu Asp Gln Thr Ile Glu Glu Gly Val Ala Ala Asp Ala Ala Ser
                325                 330                 335

Arg Asn Ala Leu Val Lys Val Lys Asn Val Val Leu Lys Leu Leu Ala
            340                 345                 350

Ala Pro Met Arg Pro Ser Ser Ala Arg Gly Arg Glu Ser Ser Val Glu
        355                 360                 365

Ser Asp Ile Gly Ser Val Arg Ser Ser Arg Ser Val Arg Pro Ser Val
    370                 375                 380

Glu Pro Gly Phe Gly Arg Arg Gly Val Ser Val Glu Pro Ser Ile Met
385                 390                 395                 400

Glu Glu Asp Glu Asn Glu Asp Ser Arg Ala Thr Leu Asp Ser Arg Met
                405                 410                 415

Thr Val Ile Lys Glu Glu Asp Ala Asp Ala Met Glu Glu
            420                 425

<210> SEQ ID NO 30
<211> LENGTH: 147
<212> TYPE: PRT
<213> ORGANISM: Aspergillus nidulans
```

```
<400> SEQUENCE: 30

Leu Leu Ser Pro Pro Leu Val Arg Ala Thr Val Ile Phe Pro Ser Ser
 1               5                  10                  15

Ser Ser Cys Arg Ser Arg Leu Lys Tyr Ser Val Ser Cys Ser Asp Leu
             20                  25                  30

Gln Leu Leu Arg Ala Asp Thr Leu His Ile Ser Ala Ile Met Thr Glu
         35                  40                  45

Ser Thr Gln Glu Gln Gly Asn Asp Gly Gln Arg Met Pro Pro Ala Pro
     50                  55                  60

Ala Thr Pro Val Glu Asp Tyr Val Phe Pro Glu Tyr Arg Leu Lys Arg
 65                  70                  75                  80

Val Met Asp Asp Pro Glu Lys Thr Pro Leu Leu Ile Ala Cys Gly
                 85                  90                  95

Ser Phe Ser Pro Ile Thr Phe Leu His Leu Arg Met Phe Glu Met Ala
             100                 105                 110

Ala Asp Tyr Val Lys Leu Ser Thr Asp Phe Glu Ile Ile Gly Gly Tyr
         115                 120                 125

Leu Ser Pro Val Ser Asp Ala Tyr Arg Lys Ala Gly Leu Ala Ser Ala
     130                 135                 140

Asn His Arg
145

<210> SEQ ID NO 31
<211> LENGTH: 91
<212> TYPE: PRT
<213> ORGANISM: Aspergillus nidulans

<400> SEQUENCE: 31

Ile Ala Met Cys Gln Arg Ala Val Asp Gln Thr Ser Asp Trp Met Met
 1               5                  10                  15

Val Asp Thr Trp Glu Pro Met His Lys Glu Tyr Gln Pro Thr Ala Ile
             20                  25                  30

Val Leu Asp His Phe Asp Tyr Glu Ile Asn Thr Val Arg Lys Gly Ile
         35                  40                  45

Asp Thr Gly Lys Gly Thr Arg Lys Arg Val Gln Val Val Leu Leu Ala
     50                  55                  60

Gly Ala Asp Leu Val His Thr Met Ser Thr Pro Gly Val Trp Ser Glu
 65                  70                  75                  80

Lys Asp Leu Asp His Ile Leu Gly Gln Tyr Gly
             85                  90

<210> SEQ ID NO 32
<211> LENGTH: 92
<212> TYPE: PRT
<213> ORGANISM: Aspergillus nidulans

<400> SEQUENCE: 32

Thr Phe Ile Val Glu Arg Ser Gly Thr Asp Ile Asp Glu Ala Leu Ala
 1               5                  10                  15

Ala Leu Gln Pro Trp Lys Lys Asn Ile His Val Ile Gln Gln Leu Ile
             20                  25                  30

Gln Asn Asp Val Ser Ser Thr Lys Ile Arg Leu Phe Leu Arg Arg Asp
         35                  40                  45

Met Ser Val Arg Tyr Leu Ile Pro Asp Pro Val Ile Glu Tyr Ile Tyr
     50                  55                  60
```

-continued

```
Glu Asn Asn Leu Tyr Met Asp Asp Gly Thr Thr Gln Pro Thr Ala Asp
 65                  70                  75                  80

Lys Gly Lys Thr Arg Glu Glu Pro Ala Pro Ser Asn
                 85                  90

<210> SEQ ID NO 33
<211> LENGTH: 68
<212> TYPE: PRT
<213> ORGANISM: Aspergillus nidulans

<400> SEQUENCE: 33

Ala Lys Ala Ala Leu Arg Arg Lys Lys Val His Glu Lys Asn Leu Glu
  1               5                  10                  15

Gln Thr Gln Ala Gln Ile Val Gln Leu Glu Gln Gln Ile Tyr Ser Ile
                 20                  25                  30

Glu Ala Ala Asn Ile Asn His Glu Thr Leu Ala Ala Met Lys Ala Ala
             35                  40                  45

Gly Ala Ala Met Glu Lys Ile His Asn Gly Met Thr Val Glu Gln Val
         50                  55                  60

Asp Glu Thr Met
 65

<210> SEQ ID NO 34
<211> LENGTH: 70
<212> TYPE: PRT
<213> ORGANISM: Aspergillus nidulans

<400> SEQUENCE: 34

Asp Lys Leu Arg Glu Gln Gln Ala Ile Asn Asp Glu Ile Ala Ile Ala
  1               5                  10                  15

Ile Thr Asn Pro Gly Phe Gly Glu Gln Val Asp Glu Asp Leu Glu
                 20                  25                  30

Ala Glu Leu Glu Gly Met Glu Gln Ala Met Asp Glu Arg Met Leu
             35                  40                  45

His Thr Gly Thr Val Pro Val Ala Asp Gln Leu Asn Arg Leu Pro Ala
         50                  55                  60

Pro Ala Asn Ala Glu Pro
 65              70

<210> SEQ ID NO 35
<211> LENGTH: 25
<212> TYPE: PRT
<213> ORGANISM: Aspergillus nidulans

<400> SEQUENCE: 35

Ala Lys Ala Lys Gln Lys Ala Glu Glu Glu Asp Glu Glu Ala Glu Leu
  1               5                  10                  15

Glu Lys Leu Arg Ala Glu Met Ala Met
                 20                  25
```

What is claimed is:

1. An isolated nucleic acid encoding an AN17 polypeptide comprising the amino acid sequence set forth as SEQ ID NO:11, 33, 34, or 35, as depicted in FIGS. 4A to 4D.

2. An isolated nucleic acid consisting essentially of a sequence selected from the group consisting of:

(a) SEQ ID NO:10, as depicted in FIGS. 4A to 4D, or degenerate variants thereof that encode the same amino acid sequence as SEQ ID NO:10 encodes;

(b) SEQ ID NO:10, as depicted in FIGS. 4A to 4D, or degenerate variants thereof that encode the same amino acid sequence as SEQ ID NO:10 encodes, wherein T is replaced by U;

(c) SEQ ID NO:12; and (d) SEQ ID NO:12, wherein T is replaced by U.

3. An isolated nucleic acid from Aspergillus consisting essentially of the nucleic acid sequence set forth as SEQ ID NO:10, and encoding an AN17 polypeptide.

4. An isolated nucleic acid molecule, said molecule comprising the cDNA sequence contained within American Type Culture Collection (ATCC) accession number 209472.

5. A vector comprising the nucleic acid of claim 1.

6. A vector comprising the nucleic acid of claim 2.

7. An expression vector comprising the nucleic acid of claim 1 operably linked to a nucleotide sequence regulatory element that controls expression of said nucleic acid.

8. An expression vector comprising the nucleic acid of claim 2 operably linked to a nucleotide sequence regulatory element that controls expression of said nucleic acid.

9. A genetically engineered host cell comprising the nucleic acid of claim 1.

10. A genetically engineered host cell comprising the nucleic acid of claim 2.

11. The host cell of claim 9, wherein the cell is a yeast or bacterium.

12. The host cell of claim 10, wherein the cell is a yeast or bacterium.

13. A genetically engineered host cell comprising the nucleic acid of claim 1 operably linked to a nucleotide sequence regulatory element that controls expression of the nucleic acid in the host cell.

14. The host cell of claim 13, wherein the cell is a yeast or bacterium.

15. A genetically engineered host cell comprising the nucleic acid of claim 2 operably linked to a nucleotide sequence regulatory element that controls expression of the nucleic acid in the host cell.

16. The host cell of claim 15, wherein the cell is a yeast or bacterium.

17. A method for identifying an antifungal agent, the method comprising:
   (a) contacting a nucleic acid encoding an AN17 polypeptide with a test compound, wherein the AN17 polypeptide has the amino acid sequence set forth as SEQ ID NOs:11, 33, 34, or 35;
   (b) detecting binding of the test compound to the nucleic acid; and
   (c) determining whether a test compound that binds to the nucleic acid inhibits growth of fungi, relative to growth of fungi cultured in the absence of the test compound that binds to the nucleic acid, wherein inhibition of growth is an indication that the test compound is an antifungal agent.

18. The method of claim 17, wherein the test compound is selected from the group consisting of polypeptides, small molecules, ribonucleic acids, and deoxyribonucleic acids.

19. The method of claim 17, wherein the test compound is an antisense oligonucleotide.

20. The method of claim 17, wherein the test compound is a ribozyme.

21. A method for identifying an antifungal agent, the method comprising:
   (a) contacting the nucleic acid of claim 2 with a test compound;
   (b) detecting binding of the test compound to the nucleic acid; and
   (c) determining whether a test compound that binds to the nucleic acid inhibits growth of fungi, relative to growth of fungi cultured in the absence of the test compound that binds to the nucleic acid, wherein inhibition of growth indicates that the test compound is an antifungal agent.

22. The method of claim 21, wherein the test compound is selected from the group consisting of polypeptides, small molecules, ribonucleic acids, and deoxyribonucleic acids.

23. The method of claim 21, wherein the test compound is an antisense molecule.

24. The method of claim 21, wherein the test compound is a ribozyme.

* * * * *